(12) United States Patent
Blumwald et al.

(10) Patent No.: US 7,442,852 B2
(45) Date of Patent: *Oct. 28, 2008

(54) HIGH SALT PLANTS AND USES FOR BIOREMEDIATION

(76) Inventors: Eduardo Blumwald, 612 Jerome St., Davis, CA (US) 95616; Maris Apse, 2217 Amar Court, Davis, CA (US) 95616; Wayne Snedden, 208 Poplar Plains, Toronto, Ontario (CA) M4V 2N4; Gil Aharon, 219 Fort York Blvd., Toronto, ON (CA) M5V 1B1

( * ) Notice: Subject to any disclaimer, the term of this patent is extended or adjusted under 35 U.S.C. 154(b) by 736 days.

This patent is subject to a terminal disclaimer.

(21) Appl. No.: 10/620,061

(22) Filed: Jul. 14, 2003

(65) Prior Publication Data

US 2006/0195948 A1  Aug. 31, 2006

Related U.S. Application Data

(63) Continuation-in-part of application No. 10/155,535, filed on May 24, 2002, now Pat. No. 6,936,750, which is a continuation-in-part of application No. 09/271,584, filed on Mar. 18, 1999, now Pat. No. 7,041,875.

(60) Provisional application No. 60/078,474, filed on Mar. 18, 1998, provisional application No. 60/395,637, filed on Jul. 12, 2002, provisional application No. 60/395,700, filed on Jul. 12, 2002.

(51) Int. Cl.
*C12N 15/82* (2006.01)
(52) U.S. Cl. .................................................. 800/289
(58) Field of Classification Search ..................... None
See application file for complete search history.

(56) References Cited

U.S. PATENT DOCUMENTS

| | | | |
|---|---|---|---|
| 4,616,100 A | 10/1986 | McHughen et al. | |
| 5,272,085 A | 12/1993 | Young et al. | |
| 5,346,815 A | 9/1994 | Krulwich et al. | |
| 5,441,875 A | 8/1995 | Hediger | |
| 5,563,246 A | 10/1996 | Krulwich et al. | |
| 5,563,324 A | 10/1996 | Tarczynski et al. | |
| 5,639,950 A | 6/1997 | Verma et al. | |
| 5,689,039 A | 11/1997 | Becker et al. | |
| 5,750,848 A | 5/1998 | Kruger et al. | |
| 5,780,709 A | 7/1998 | Adams et al. | |
| 5,859,337 A | 1/1999 | Gasser et al. | |
| 6,861,574 B2 | 3/2005 | Fukuda et al. | |
| 6,936,750 B2 * | 8/2005 | Blumwald et al. | 800/298 |
| 7,041,875 B1 * | 5/2006 | Blumwald et al. | 800/298 |
| 2002/0023282 A1 * | 2/2002 | Gaxiola | 800/289 |
| 2003/0046729 A1 | 3/2003 | Blumwald et al. | |
| 2005/0028235 A1 | 2/2005 | Zhang et al. | |
| 2005/0032112 A1 | 2/2005 | Fukuda et al. | |
| 2005/0034191 A1 | 2/2005 | Blumwald | |

FOREIGN PATENT DOCUMENTS

| | | |
|---|---|---|
| EP | 1143002 A1 | 10/2001 |
| WO | WO 91/06651 | 5/1991 |
| WO | WO 96/39020 | 12/1996 |
| WO | WO 97/13843 | 4/1997 |
| WO | WO 99/47679 | 9/1999 |
| WO | WO 00/37644 | 6/2000 |

OTHER PUBLICATIONS

U.S. Appl. No. 11/067,558, filed Feb. 24, 2005, Blumwald et al.
U.S. Appl. No. 11/067,456, filed Feb. 24, 2005, Blumwald et al.
U.S. Appl. No. 11/065,977, filed Feb. 24, 2005, Blumwald et al.
Al-Karaki, Ghazi N. (2000) "Growth, Water Use Efficiency, and Sodium and Potassium Acquisition by Tomato Cultivars Grown Under Salt Stress," Journal of Plant Nutrition, 23(1):1-8.
Apse et al. (2002) "Engineering salt tolerance in plants" Current Opinion in Biotechnology 13: pp. 146-150.
Apse et al. (1999) "Salt tolerance conferred by overexpression of a vauolar Na+/H+ antiport in Arabidopsis" Science 285 (5431): pp. 1256-1258.
Apse et al. (1998) "Cloning and Characterization of Plant Sodium/Proton Antiports" 11 International Workshop on Plant Membrane Biology, Aug. 1998, Cambridge, U.K. (Abstract).
Apse et al. (1998) "Identification of two putative sodium/proton antiports in Arabidoposis" Plant Membrane Biology Workshop Aug. 1998, Cambridge, U.K. (Poster).
Barkla et al. (1995) "Tonoplast Na+/H+ antiport activity and its energization by the vacoular H+ −ATPase in the halophytic plant Mesembryanthemum crystallinum L" Plant Physiol. 109: pp. 549-556.
Barkla et al. (1994) "The plant vacuolar Na+/H+ antiport" Symp. Soc. Exp. Biol. 48: pp. 141-153.
Blumwald (2000) "Sodium transport and salt tolerance in plants" Current Opinion in Cell Biology 12: pp. 431-434.
Blumwald et al. (Dec. 1998) "Cloning of plant sodium/proton antiports in *Arabidopsis*" Eastern Regional Meeting of the Canadian Society of Plant Physiologists, Toronto.
Blumwald et al. (Jun. 1998) "Cloning and characterization of a plant sodium/proton antiport" Annual Meeting of the American Society of Plant Physiologists, Madison, USA.
Blumwald et al. (Aug. 1998) "Cloning and characterization of a plant sodium/proton antiports" 11 International Workshop on Plant Membrane Biology, Aug. 1998, Cambridge, U.K.
Blumwald et al. (Aug. 1998) "Cloning and characterization of a plant sodium/proton antiports" Gordon Conference on Drought and Salinity Stress in Plants, Oxford, UK.

(Continued)

*Primary Examiner*—Anne R Kubelik
(74) *Attorney, Agent, or Firm*—Morrison & Foerster LLP

(57) ABSTRACT

The subject invention includes non-naturally occurring salt tolerant plants that accumulate sodium in their tissues substantially in the vacuole. The present invention also includes methods of making such non-naturally occurring plants. One preferred method is generating a transgenic plant that has an ectopically expressed NHX related gene product.

8 Claims, 9 Drawing Sheets

OTHER PUBLICATIONS

Bohnert et al. (1996) "Strategies for engineering water-stress tolerance in plants" Trends in Biotechnology 14(3): pp. 89-97.

Borgese et al. (1992) "Cloning and expression of a cAMP-activated Na+/H+ exchanger: evidence that the cytoplasmic domain mediates hormonal regulation" PNAS USA 89: pp. 6765-6769.

Bork (2000) "Powers and Pitfalls in Sequence Analysis: the 70% Hurdle" Genome Research, vol. 10: pp. 398-400.

Bowie et al. (1990) "Deciphering the Message in Protein Sequences: Tolerance to Amino Acid Substitutions" Science, vol. 247, pp. 1306-1310.

Brant et al. (1997) Human Na+/H+ exchanger isoform NHE3 composite cDNA: GenBank Accession No. T51330.

Broun et al. (1998) "Catalytic Plasticity of Fatty Acid Modification Enyzmes Underlying Chemical Diversity of Plant Lipids" Science, vol. 282: pp. 1315-1317.

Counillon et al. (May 1993) "A Point Mutation of the Na+/H+ Exchanger Gene (NHE1) and Amplification of the Mutated Allele Confer Amiloride Resistance Upon Chronic Acidosis" Proc. Natl. Acad. Sci. USA 90(10): pp. 4508-4512.

Covitz et al. (Nov. 1997) Expressed sequence tags from a root hair-enriched *Medicago truncatula* cDNA library: GenBank Accession No. AA660573.

Dante et al. (1997) "AC 004655": *Arabidopsis thaliana* BAC TM021B04: EMBL Database Accession No. AC 004655.

Darley et al. (1998) "ANA1 a Na+/H+ Antiporter From *Arabidopsis*?" 11th International Workshop on Plant Membrane Biology, Aug. 1998, Cambridge, U.K.

Dietrich et al. (1997) Sequence of *S. cerevisiae* lambda 3641 and cosmids 9461, 9831, and 9410: GenBank Accession No. 927695.

Fukuda et al. (Aug. 1999) "AB021878" *Oryza sativa (Japonica* cultivar-group) OsNHX1 mRNA: EMBL Database Accession No. AB021878.

Fukuda et al. (1999) "Molecular Cloning and Expression of the Na+/H+ Exchanger Gene in *Oryza sativa*" Biochim. Biophys. Acta. 1446 (1-2): pp. 149-155.

Fukuda et al. (1998) "Na+/H+ Antiporter in Tonoplast Vesicles from Rice Roots" Plant Cell Physiol. 39: pp. 196-201.

Fukuda et al. (Mar. 2001) "The Functional analysis of the rice Na+/H+ antiporter gene" Plant Cell Physiol. 42 (Supp.): p. s210.

Gaxiola et al. (1996) "The *Arabidopsis thaliana* proton transporters, AtNhx1 and Avp1, can function in cation detoxification in yeast" PNAS USA 96 (4): pp. 1480-1485.

Gisbert, Carmina et al. (May 2000) "The Yest HAL1 Gene Improves Salt Tolerance of Transgenic Tomato," Plant Physiology, 123:393-402.

Gordon-Kamm et al. (1990) "Transformation of Maize Cells and Regneration of Fertile Transgenic Plants" Plant Cell 2: 603-618.

Guo, Haiwei H. et al. (Jun. 22, 2004) "Protein Tolerance to Random Amino Acid Change," PNAS, 101(25):9205-9210.

Hahnnenberger et al. (1996) "Functional expression of the *Schizosaccharomyces pombe* Na+/H+ antiporter gene, sod2, in *Saccharomyces cerevisiae*" PNAS USA 93: pp. 5031-5036.

Hiei et al. (1994) "Efficient Transformation of rice mediated by *Agrobacterium* and sequence analysis of the boundary of the T-DNA" Plant J. 6: pp. 271-282.

Hill et al. (1998) "Functional Analysis of Conserved Histidines in ADP-Glucose Pyrophosporylase from *Escherichia coli*" Biochem. Biophys. Res. Comm. 244: pp. 573-577.

Ichida et al. (1996) "Increased Resistance to Extracellular Cation Block by Mutation of the Pore Domain of the *Arabidopsis* Inward-rectifying K+ Channel KAT1" J. Membrane Biol. 151: pp. 53-62.

Jacoby (Aug. 23, 1999) "Botanists design plants with a taste for salt" Chemical Engineering News: p. 9.

Kadyrzhanova et al. (1995) Sequences for STS primer sets: GenBank Accession No. L44032.

Kaufman (Jul. 31, 2001) "A New Strain of Tomatoes, And Don't Hold the Salt" Washington Post: p. A03.

Kinclova et al. (2001) "Functional study of the *Saccharomyces cerevisiae* Nha1p C-terminus" Mol. Microbiol. 40 (3): pp. 656-668.

Lazar et al. (1988) "Transforming Growth Factor a: Mutation of Aspartic Acid 47 and Leucine 48 Results in Different Biological Activities" Molecular and Cellular Biology 8: pp. 1247-1252.

Liu et al. (2000) "Partial Deletion of a Loop Region in the High Affinity K+ Transporter HKT1 Changes Ionic Permeability Leading to Increased Salt Tolerance" J. Biol. Chem. 275 (36): pp. 27924-27932.

Murphy, L. et al. (Nov. 4, 1998) "Direct Submission Schizosaccharomyces Pombe Chromosome I Sequencing Project," GenBank Accession No. 3850064.

Nass and Rao (Aug. 1998) "Novel Localization of a Na+/H+ Exchanger in a late Endosomal Compartment of Yeast" J. Biol. Chem. 273 (33): pp. 21054-21060.

Nass et al. (Oct. 1997) "Intracellular Sequestration of Sodium by a Novel Na+/H+ Exchanger in Yeast Is Enhanced by Mutations in the Plasma Membrane H+ – ATPase" J. Biol. Chem. 272 (42): pp. 26145-26152.

Newman et al. (1998) "AC T75860": *Arabidopsis* cDNA clone of Lambda-PRL2: EMBL Database Accession No. AC T75860.

Numata et al. (Mar. 1998) "Identification of a Mitochondrial Na+/H+ Exchanger" J. Biol. Chem. 273 (12): pp. 6951-6959.

O'Connor (Aug. 2001) "Altered Tomato Thrives in Salty Soil" New York Times.

Ohki et al. (1995) "AC D49589": EMBL Database Accession No. AC D49589.

Ohki et al. (1995) "Preference of recombination sites involved in the formation of extrachromosomal copies of the human alphoid Sau3A repeat family" Nucleic Acids Res. 23: pp. 4986-4991.

Ohta, Masaru et al. (2002) "Introduction of a Na+/H+ Antiporter Gene from *Atriplex Gmelini* Confers Salt Tolerance to Rice," FEBS Letters 26785:1-4.

Orlowski and Grinstein (Sep. 1997) "Minireview: Na+/H+ Exchangers of Mammalian Cells" J. Biol. Chem. 272 (36): pp. 22373-22376.

Plantsp (2002) "PlantsP: Functional Genomics of Plant Phosphorylation-PlantsP Protein 27103" Retrieved Feb. 5, 2005, from http://plantsp.sdsc.edu/cgi-bin/detail.cgi?db=plantsp&plantsp_id=27103.

Rausch et al. (1996) "Salt stress responses of higher plants: The role of proton pumps and Na=/H+ –antiporters" Journal of Plant Physiology 148 (3-4): pp. 425-433.

Rhoads et al. (1998) "Regulation of the cyanide-resistant alternative oxidase of plant mitochondria" J. Biol. Chem. 273 (46): pp. 30750-30756.

Rubio et al. (1999) "Genetic Selection of Mutations in the High Affinity K+ Transporter HKT1 That Define Functions of a Loop Site for Reduced Na+ Permeability and Increase Na+ Tolerance" J. Biol. Chem. 274 (11): pp. 6839-6847.

Rus, A.M. et al. (2001) "Expressing the Yeast HAL1 Gene in Tomato Increases Fruit Yield and Enhances K+/Na+ Selectivity Under Salt Stress," Plant, Cell and Environment, 24:875-880.

Sasaki et al. (Apr. 1998) Rice cDNA from panicle C91832: Genbank Accession No. C91832.

Sasaki et al. (Apr. 1998) Rice cDNA from panicle C91861: GenBank Accession No. C91861.

Schachtman et al. (1997) "Molecular and functional characteraization of a novel low-affinity cation transporter (LCT1) in higher plants" PNAS USA 94: pp. 11079-11084.

Seki et al. (2002) RAFL6 *Arabidopsis thaliana* cDNA clone: GenBank Accession Nos. AV785096 and AV798305.

Strathmann et al. (1989) "Diversity of the G-protein family: sequences from five additional alpha subunits in the mouse" Natl. Acad. Sci. USA 86: pp. 7407-7409.

Travis, J. (Aug. 4, 2001) "Gene Makes Tomatoes Tolerate Salt," Science News, 60:68.

West, D.W. et al. (1984) "Response of Six Grape Cultivars to the Combined Effects of High Salinity and Rootzone Waterlogging," J. Amer. Soc. Hort. Sci. 109(6):844-851.

Waditee et al. (2001) "Halotolerant Cyanobacterium Aphanothece Halophytica Contains an Na+/H+ Antiporter, Homologous to Eukaryotic Ones, with Novel Ion Specificity Affected by C-terminal Tail" J. Biol. Chem. 276 (40): pp. 36931-36938.

Wood et al. (Nov. 1998) Direct submission *Schizosaccharomyces pombe* chromosome I sequencing project: GenBank Accession No. CAB10103.

Yamamoto et al. (Oct. 1998) Rice cDNA from green shoot: GenBank Accession No. AU032544.

Yokoi et al. (2002) *Arabidopsis thaliana* Na+/H+ exchanger 5 (NHX5) mRNA: GenBank Accession No. AF490589.

Zandonella (Jul. 2001) "Gene modified tomato revels in salty soils" New Scientist. Retrieved Feb. 23, 2002, from <http://www.newscientist.com/channel/health/gm-food/dn1092>.

Zhang et al. (2001) "Engineering salt-tolerant *Brassica* plants: Characterization of yeld and seed oil quality in transgenic plants with increased vacuolar sodium accumulation" PNAS USA 98 (22): pp. 12832-12836.

Zhang et al. (2001) "Transgenic salt-tolerant tomato plants accumulate salt in foliage but not in fruit" Nature Biotechnology 19: pp. 765-768.

Cuartero, Jesús et al. (1999) "Tomato and salinity." *Scientia Horticulture*, 78:83-125.

Dierig, D.A. et al. (2001) "Registration of WCL-SL1 Salt Tolerant *Lesquerella fendleri* Germplasm." *Crop. Sci.*, 41:604-605.

Francois, L.E. et al. (1964) "Salt Tolerance of Safflower." *Agronomy Journal*, 58:38-40.

Mäser, Pascal et al. (Aug. 2001) "Phylogenetic Relationships within Cation Transporter Families of *Arabidopsis*." *Plant Physiology*, 126:1646-1667.

Nakamura, Yasukazu et al. (1998) "Structural Analysis of *Arabidopsis thaliana* Chromosome 5. VII. Sequence Features of the Regions of 1,013,767 bp Covered by Sixteen Physically assigned P1 and TAC Clones." *DNA Research*, 5:297-308.

Santa-Maria, Guillermo E. et al. (Dec. 1997) "The HAK1 Gene of Barley Is a Member of a Large Gene Family and Encodes a High-Affinity Potassium Transporter." *The Plant Cell*, 9:2281-2289.

Venema, K. et al. (Jun. 20, 2003) "A Novel Intracellular $K^+/H^+$ Antiporter Related to $Na^+/H^+$ Antiporters Is Important for $K^+$ Ion Homeostasis in Plants." *The Journal of Biological Chemistry*, 278(25):22453-22459.

Yermanos, D. M. et al. (1964) "Soil Salinity Effects on the Chemical Composition of the Oil and the Oil Content of Safflower Seed." *Agronomy Journal*, 54:35-37

Yokoi et al. (2002) "Differential expression and function of *Arabidopsis thaliana* NHX Na+/H+ antiporters in the salt stress response." *The Plant Journal*, 30(5):529-539.

GenBank Accession No. 3850064, Nov. 4, 1998, Source: Fission Yeast; Reference 1 Authors: Murphy L. and Harris, D.; Reference 2 Authors: Wood, V., Barrell, B.G., and Rajandream, M.A.; 2 pgs.

GenBank Accession No. AF106324, Mar. 3, 1999, located at <http://www.ncbi.nlm.nih.gov/entrez/viewer.fcgi?db=nucleotide &val=4324 596>, visited on Jan. 26, 2005, 2 pgs.

Chandler et al. (2003) "When negative is positive in functional genomics" *Trends in Plant Science*, 8: 279-285.

Gorman, (Aug. 4, 2001) "Researchers take an element off the table" *Science News*, 160(5): 68.

Tse, C.M. et al. (May 5, 1992) "Cloning and Sequencing of a rabbit CDNA encoding an intestinal and kidney-specific Na(+)/H/(+) exchanger isoform (NHE-3)" *J. Biol. Chem.* 267:9340-9346.

Nakamura, Yasukazu et al. (Sep. 25, 1998) "Structured Analysis of *Arabidopsis thaliana* Chromosome 5. VII. Sequence Features of the Regions of 1,013,767 bp covered by Sixteen Physically assigned P1 and TAC Clones," *DNA Research*, 5:297-308.

\* cited by examiner

HIGH SALT PLANTS AND USES FOR BIOREMEDIATION

RELATED APPLICATIONS

This application is a continuation-in-part application of U.S. application Ser. No. 10/155,535, filed May 24, 2002, which is a continuation-in-part of application Ser. No. 09/271,584, filed Mar. 18, 1999, which claims the benefit of U.S. Provisional Application No. 60/078,474, filed Mar. 18, 1998, which are all incorporated by reference herein in their entirety. This application further claims the benefit of U.S. Provisional Applications No. 60/395,637 and No. 60/395,700, both filed Jul. 12, 2002, which are all incorporated by reference herein in their entirety.

FIELD OF THE INVENTION

This invention is in the field of agricultural biotechnology. In particular, this invention relates to plants with elevated levels of salt stored in vacuoles and use of such plants for bioremediation with salt tolerant plants.

BACKGROUND OF THE INVENTION

Environmental stress due to salinity is one of the most serious factors limiting the productivity of agricultural crops, which are predominantly sensitive to the presence of high concentrations of salts in the soil. Large terrestrial areas of the world are affected by levels of salt inimical to plant growth. It is estimated that 35-45% of the 279 million hectares of land under irrigation is presently affected by salinity. This is exclusive of the regions classified as arid and desert lands, (which comprises 25% of the total land of our planet). Salinity has been an important factor in human history and in the life spans of agricultural systems. Salt impinging on agricultural soils has created instability and has frequently destroyed ancient and recent agrarian societies. The Sumerian culture faded as a power in the ancient world due to salt accumulation in the valleys of the Euphrates and Tigris rivers. Large areas of the Indian subcontinent have been rendered unproductive through salt accumulation and poor irrigation practices. In this century, other areas, including vast regions of Australia, Europe, southwest USA, the Canadian prairies and others have seen considerable declines in crop productivity.

Although there is engineering technology available to combat this problem, though drainage and supply of high quality water, these measures are extremely costly. In most of the cases, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, an application of water is also an application of salt that compounds the salinity problem.

Increasing emphasis is being given to modify plants to fit the restrictive growing conditions imposed by salinity and even bioremediate the soil through extraction of the salt. If economically important crops could be manipulated and made salt resistant, this land could be farmed resulting in greater sales of seed and greater yield of useful crops. Conventional breeding for salt tolerance has been attempted for a long time. These breeding practices have been based mainly on the following strategies: a) the use of wide crosses between crop plants and their more salt-tolerant wild relatives, b) screening and selecting for variation within a particular phenotype, c) designing new phenotypes through recurrent selection. (Rush, et al. (1981); Norlyn (1980) and Tal (1985) The lack of success in generating tolerant varieties (given the low number of varieties released and their limited salt tolerance) would suggest that conventional breeding practices are not enough and that in order to succeed a breeding program should include the engineering of transgenic crops. (Flowers, et al. (1995) and Bonhert, et al. (1996))

Several biochemical pathways associated with stress tolerance have been characterized in different plants and a few of the genes involved in these processes have been identified and in some cases the possible role of proteins has been investigated in transgenic/overexpression experiments. Several compatible solutes have been proposed to play a role in osmoregulation under stress. Such compatible solutes, including carbohydrates, amino acids and quaternary N-compounds have been shown to increase osmoregulation under stress. (Tarcynski, et al. (1995); Kishor (1995) and Ishitani (1995)) Also, proteins that are normally expressed during seed maturation (LEAs, Late Embryogenesis Abundant proteins) have been suggested to play a role in water retention and in the protection of other proteins during stress. The overexpression of LEA in rice provided a moderate benefit to the plants during water stress. (Xu, et al. (1996) and Wu, et al. PCT # WO/9713843) A single gene (sod2) coding for a Na+/H+ antiport has been shown to confer sodium tolerance in fission yeast. (Jia, et al. (1992) and Young, et al., PCT # WO/0106651) One of the main disadvantages of using this gene for transformation of plants is associated with the typical problems encountered in heterologous gene expression, i.e. incorrect folding of the gene product, targeting of the protein to the target membrane and regulation of the protein function.

Plants that tolerate and grow in saline environments have high intracellular salt levels. A major component of the osmotic adjustment in these cells is accomplished by ion uptake. The utilization of inorganic ions for osmotic adjustment suggests that salt-tolerant plants must be able to tolerate high levels of salts within their cells. However, enzymes extracted from these plants show high sensitivity to salt. The sensitivity of the cytosolic enzymes to salt would suggest that the maintenance of low cytosolic sodium concentration, either by compartmentation in cell organelles or by exclusion through the plasma membrane, must be necessary if the enzymes in the cell are to be protected from the inimical effects of salt.

Plant cells are structurally well suited to the compartmentation of ions. Large membrane-bound vacuoles are the site for a considerable amount of sequestration of ions and other osmotically active substances. A comparison of ion distribution in cells and tissues of various plant species indicates that a primary characteristic of salt tolerant plants is their ability to exclude sodium out of the cell and to take up sodium and to sequester it in the cell vacuoles. Transport mechanisms could actively move ions into the vacuole, removing the potentially harmful ions from the cytosol. These ions, in turn, could act as an osmoticum within the vacuole, which would then be responsible for maintaining water flow into the cell. Thus, at the cellular level both specific transport systems for sodium accumulation in the vacuole and sodium extrusion out of the cell are correlated with salt tolerance. It would be a particular advantage to use plants that accumulate salt in the vacuole in response to high salt in the soil. Such plants would accumulate the salt in the leaves and roots, which can be removed, removing a portion of the salt.

Furthermore, profits in the cattle industry are affected by the high cost of labor; thus, management procedures which reduce labor requirements are important. One management tool frequently used is regulating feed intake with salt. Self-feeding supplements tend to allow timid, slow-eating cows to get their share and it is an easy method of providing Vitamin A, phosphorus and other feed additives. Because there are practical limits to the amount of salt cattle eat, salt can also be used to restrict the consumption of highly palatable feeds such as grain and supplement. Salt is also added to feed grain because with high grain rations, urinary calculi (phosphatic type) are a problem. This problem is controlled by feeding salt to flush out the stones. This is particularly true with milo and cottonseed meal based finishing programs. Salt supplements are added directly to the feed directly in the proportions desired. The addition and mixing requires labor which reduces profits. Thus there is a need for feed plants that already contain salt.

There is a long felt need in the art for the in situ remediation of soils damaged by accumulation of salts. The present invention enables phytoremediation and/or revegetation of contaminated environments via salt tolerant plants. The plants of the present invention may be grown in high salt soil and will accumulate salt in the leaves and roots. Such salt containing plant materials may be used as forage for cattle with the additional advantage that extra salt need not be added to the feed.

SUMMARY OF THE INVENTION

In order to meet these needs, the present invention is directed to transgenic plants that are able to grow and bioremediate soil in the presence of elevated salt concentrations. In particular, the transgenic plants remove salt from the soil and accumulate it in leaves and roots. The plants may then be harvested and fed to cattle as salt containing feed or simply removed. In a preferred embodiment of the present invention, sodium does not accumulate in the plant fruit, so the fruit is suitable for commercial sale. In particular, we show that transgenic Brassica napus plants overexpressing a vacuolar $Na^+/H^+$ antiport were able to grow, flower and produce seeds in the presence of 200 mM NaCl. Brassica napus, commonly known as canola or rapeseed, represents one of the most important oilseed crops that is being cultivated worldwide. The sustained growth of the transgenic plants, the seed yields and the quality of the seed oil demonstrate the potential use of these transgenic plants for bioremediation of contaminated soils. This technology finds use in the bioremediation of soils using salt tolerant forage crops, trees and oil seed crops.

One aspect of the present invention is directed to a non-naturally occurring non-halophyte plant comprising a tissue with an elevated level of sodium substantially in the vacuole when cultivated in high salt. In one variation, the elevated salt level in the vacuole is two fold higher, three fold higher, four fold higher, five fold higher, ten fold higher, or twenty fold higher compared to the level in a comparable naturally occurring plant. In another variation, the tissue is leaf or root tissue. In yet another variation, the high salt is two fold higher, three fold higher, four fold higher, five fold higher, ten fold higher, fifteen fold higher, twenty fold higher, twenty five fold higher, or thirty fold higher than the optimal salt levels for the comparable naturally occurring plant variety. In another variation, the high salt is at or above the salt level in which the naturally occurring plant variety cannot survive. In still another variation, the plant is tomato or canola. In another variation, the cultivation in high salt conditions may be cultivation where the high salt conditions persist through the entire life cycle of the plant, the germination stage, the vegetative growth stage, the flowering stage, the seed embryogenesis stage, the stage of seed ripening, and any combination of the foregoing stages. In another variation, the plant has increase salt tolerance due to sequestering sodium in the vacuole.

Another aspect of the present invention is directed to a non-naturally occurring non-halophyte plant comprising a tissue with an enhanced level of sodium substantially in the vacuole when cultivated in high salt. In one variation, the enhanced salt level in the vacuole is two fold higher, three fold higher, four fold higher, five fold higher, ten fold higher, or twenty fold higher compared to the level in the same plant grown at low to moderate salt conditions. In another variation, the tissue is leaf or root tissue. In still another variation, the plant is tomato or canola. In another variation, the cultivation in high salt conditions may be cultivation where the high salt conditions persist through the entire life cycle of the plant, the germination stage, the vegetative growth stage, the flowering stage, the seed embryogenesis stage, the stage of seed ripening, and any combination of the foregoing stages. In another variation, the plant has increase salt tolerance due to sequestering sodium in the vacuole.

In another aspect of the present invention, the plant comprises a transgene. In one variation, the transgene comprises a first nucleic acid sequence encoding a vacuolar targeted Na+/H+ transporter or a plant derived vacuolar Na+/H+ transporter. In another variation, the transgene comprises a first nucleic acid selected from the following group: a nucleic acid molecule of the coding strand shown in SEQ ID NO:1, or a complement thereof; a nucleic acid molecule encoding the amino acid sequence shown in SEQ ID NO:2; a nucleic acid molecule that hybridizes to the sequence set forth in SEQ ID NO:1 or the complement of the sequence set forth in SEQ ID NO:1 under highly stringent conditions that include at least one wash in 0.1×SSC, 0.1% SDS, at 65° C. for thirty minutes; and a nucleic acid molecule encoding a plant NHX transporter polypeptide that hybridizes to the sequence set forth in SEQ ID NO:1 or the complement of the sequence set forth in SEQ ID NO:1 under moderately stringent conditions that includes at least one wash in 0.1×SSC, 0.1% SDS, at 50° C. for thirty minutes. In still another variation, the transgene further comprises a promoter sequence operably linked to the first nucleic acid sequence. In yet another variation, the promoter is a constitutive promoter or an inducible promoter. In certain variations, the promoter may be selected from the group consisting of the 35 S promoter and the CaMV promoter.

Yet another aspect of the present invention is directed to a non-naturally occurring non-halophyte plant comprising a plant with increased salt tolerance due to the ability to sequester sodium in the vacuole. Other variations exist similar to the variations discussed above.

An additional aspect of the present invention is a seed produced from any of the foregoing plants and variations thereof.

The present invention also includes methods of generating the foregoing. One variation includes transfecting a plant with a transcriptional regulatory element and identifying plants comprising seeds with normal or near normal fatty acid distribution when cultivated in high salt. In another variation, plants are transfected with a transcriptional regulatory element and identifying a plant wherein said transcriptional regulatory element has integrated operably linked to a Na+/H+ transporter. In yet another variation, the transcriptional regulatory element is a promoter, an enhancer element, a repressor element or a boundary element. In one variation, plants are transfected with a transgene comprising a Na+/H+ transporter and a plant comprising seeds with normal or near normal fatty acid distribution when cultivated in high salt is identified. In one variation, the Na+/H+ transporter gene is selected from the group consisting of a nucleic acid molecule of the coding strand shown in SEQ ID NO:1, or a complement thereof; a nucleic acid molecule encoding the amino acid sequence shown in SEQ ID NO:2; a nucleic acid molecule that hybridizes to the sequence set forth in SEQ ID NO:1 or the complement of the sequence set forth in SEQ ID NO:1 under highly stringent conditions that include at least one wash in 0.1×SSC, 0.1% SDS, at 65° C. for thirty minutes; and a nucleic acid molecule encoding a plant NHX transporter polypeptide that hybridizes to the sequence set forth in SEQ ID NO:1 or the complement of the sequence set forth in SEQ ID NO:1 under moderately stringent conditions that includes at least one wash in 0.1×SSC, 0.1% SDS, at 50° C. for thirty minutes.

Another aspect of present invention is a method of lowering the salt content of soil comprising cultivating of any of the foregoing plant variations in the soil, harvesting the plant and removing the plant or the tissue with an elevated level of sodium or an enhanced level of sodium. In one variation, the electrical conductivity of the soil is at least 15 dS/m, at least 20 dS/m, at least 25 dS/m, at least 30 dS/m, at least 40 dS/m, or at least 50 dS/m. In another variation, the harvesting step is omitted from the method.

Bar=25 cm.

Figure 2:
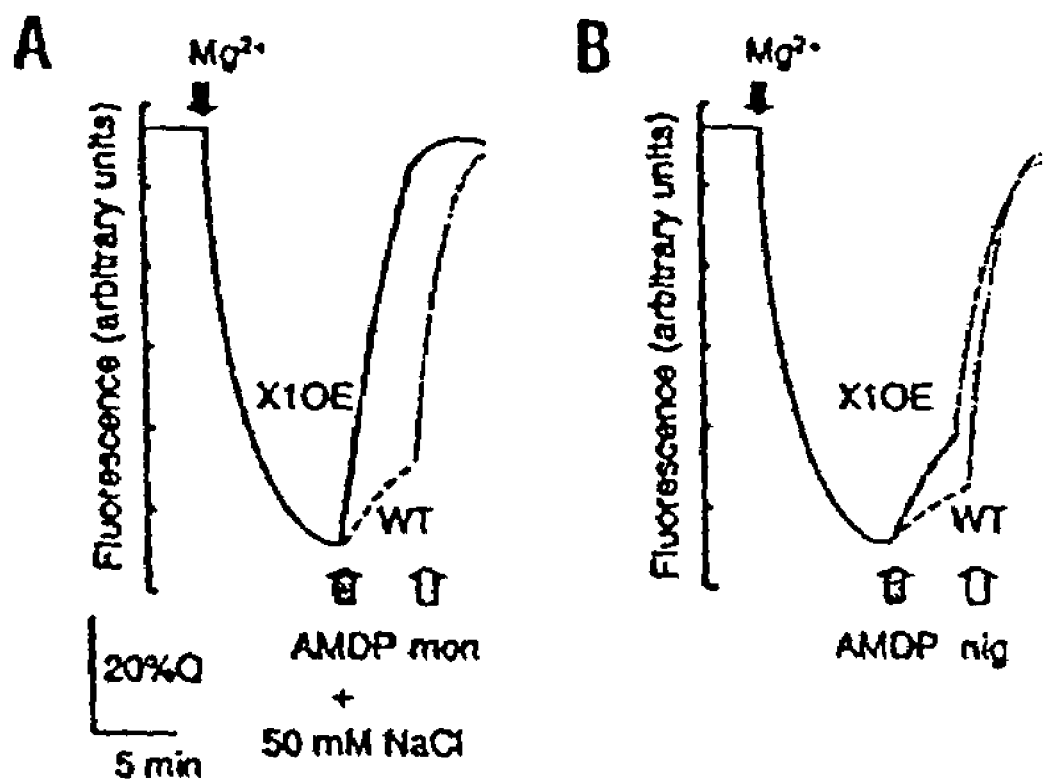

FIG. 2 shows Na+/H+ exchange activity in leaf tonoplast vesicles Membrane fractions were purified from leaves using the method described5 with the modifications described4. At the indicated times, the vacuolar H+-PPiase was activated by the addition of Mg2+. When a steady-state pH gradient (acidic inside) was formed, the PPi-dependent H+ transport activity was stopped by the addition of AMDP and the rates of cation/H+ exchange were determined in vesicles isolated from wild-type plants (WT) and transgenic plants overexpressing AtNHX1 (X1OE). (A) Na+-dependent H+ exchange, (B) K+-dependent H+ exchange. The addition of monensin (mon), an artificial Na+/H+ antiport, or nigericin (nig), an artificial K+/H+ antiport, abolished the pH gradient and the fluorescence was fully recovered. The figure shows a typical recording.

Figure 3:
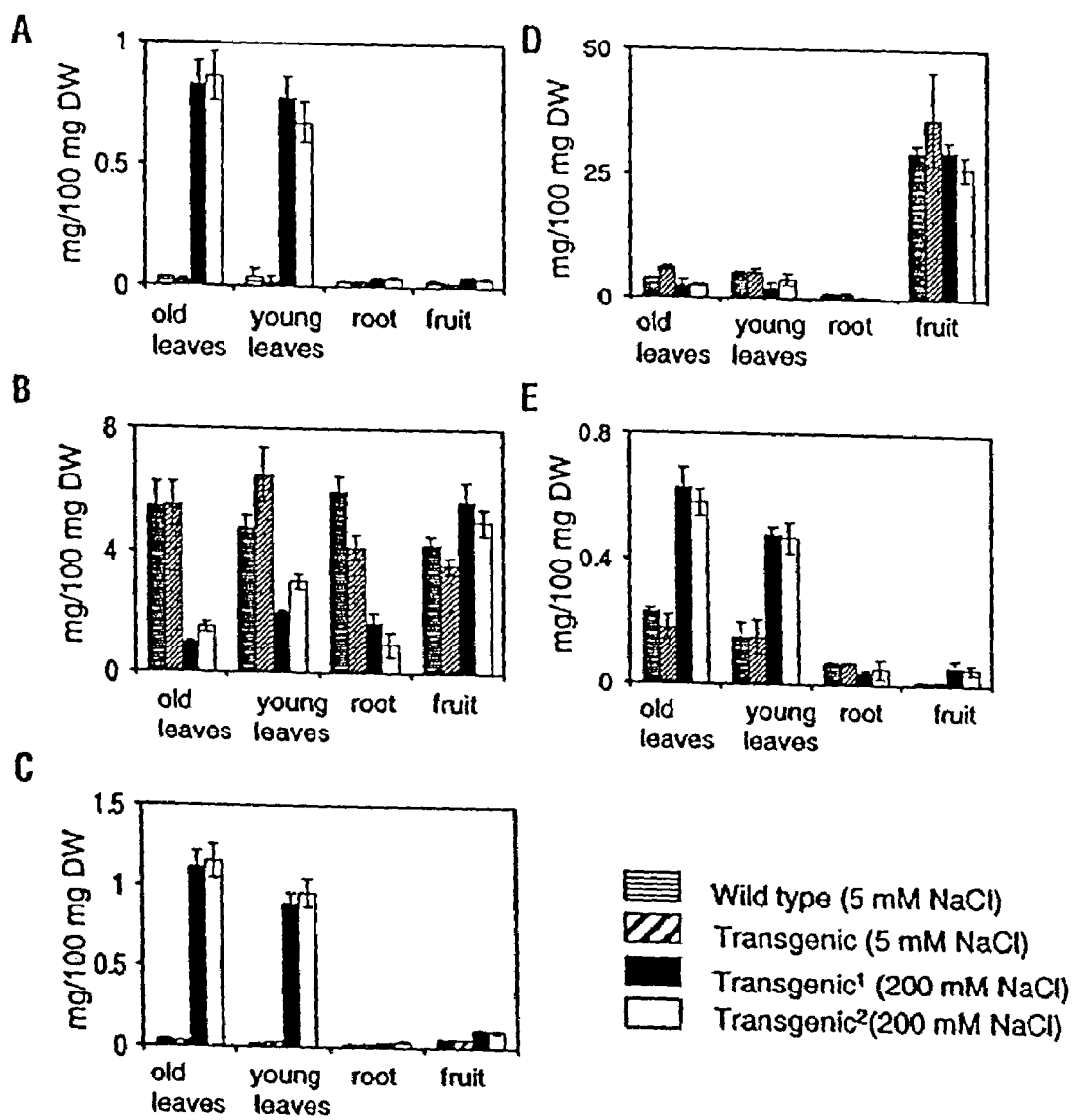

FIG. 3 shows ion, sugar, and proline contents of wild-type and transgenic plants grown at different salt concentrations. Wild-type (hatched line bars) and transgenic plants (crosshatched line bars) grown in the presence of 5 mM NaCl. Two independent transgenic lines (black and white bars) grown in the presence of 200 mM NaCl. (A) Na+ contents; (B) K+ contents; (C) Cl—contents; (D) soluble sugar contents; (E) proline contents. For each determination, leaves, roots and fruits from ten plants were collected from each hydroponic tank and pooled. Values are the Mean Δ S.D. from material collected from three hydroponic tanks (n=3).

Figure 4:
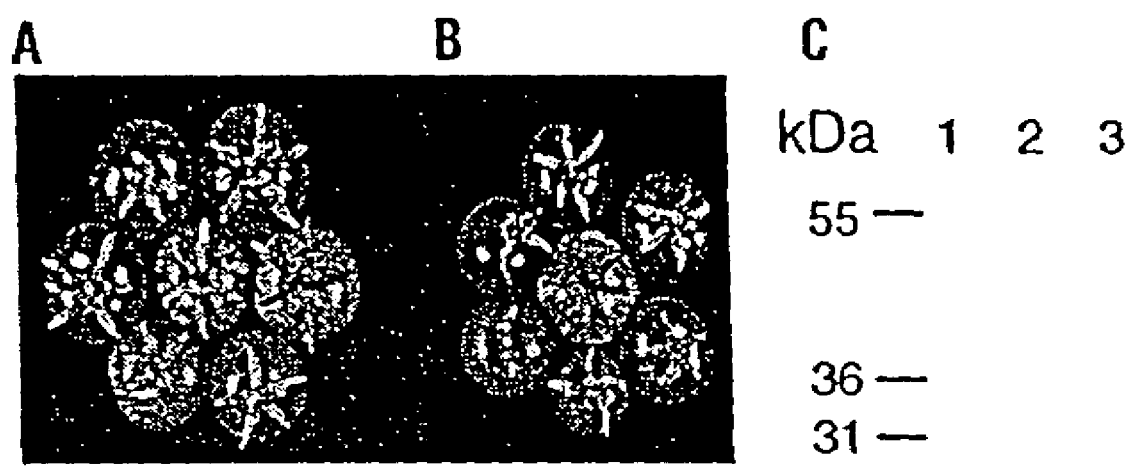

FIG. 4 shows fruits from wild-type and transgenic plants. (A) tomato fruits from wild-type plants; (B) tomato fruits from transgenic plants. (C) Western blots from fruit tonoplast proteins (5 μg) tested with antibodies raised against AtNHX1; Wild-type plants grown in the presence of 5 mM NaCl (lane 1). Two independent transgenic lines grown in the presence of 200 mM NaCl (lanes 2 and 3).

Figure 5:

FIG. 5 shows salt tolerance of wild-type plants and transgenic *Brassica* plants overexpressing AtNHX1 grown in the presence of 200 mM NaCl. Wild-type (wt) and homozygous plants showing high ($X1OE_1$), medium ($X1OE_2$) and low ($X1OE_3$) levels of expression were grown in the presence of 200 mM NaCl. Plants shown after 10 weeks of growth. Inset: Western blots of leaf tonoplast-enriched membrane fractions isolated from wild-type and transgenic plants with low, medium and high levels of expression of AtNHX1. Blots were probed with antibodies raised against the C-terminus of AtNHX1. Equal amounts of protein (20 μg) were loaded in each lane. Relative molecular masses are indicated on the left.

Figure 6:
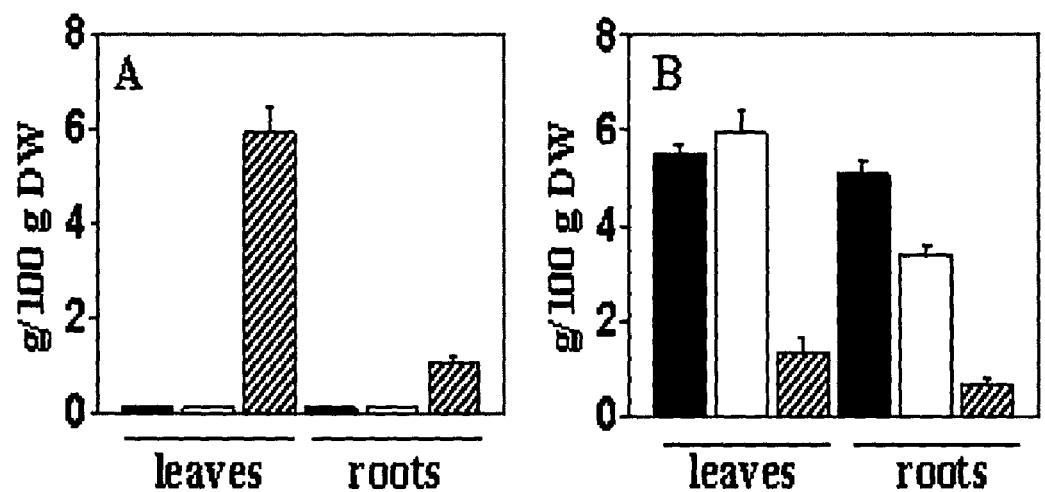

FIG. 6 shows $Na^+$ and $K^+$ contents of leaves and roots from wild-type plants grown at 10 mM NaCl (black bars) and transgenic plants (X1OE1) grown at 10 mM NaCl (white bars) and 200 mM NaCl (hatched line bars). (A) $Na^+$ content; (B) $K^+$ content. Leaves and roots were collected from fifteen plants from each treatment, the material pooled in three groups and ion contents measured as described in Materials and Methods. Values are the Mean±S.D (n=3).

Figure 7:
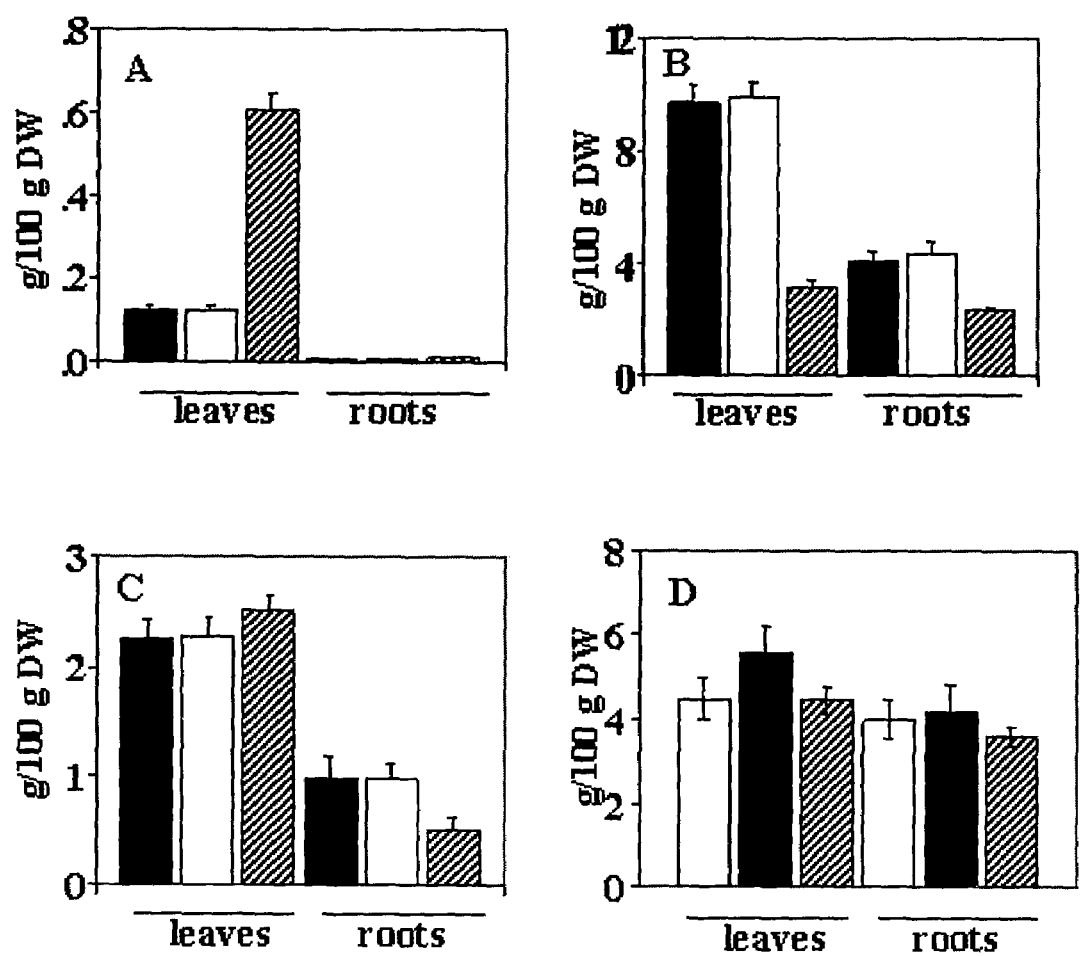

FIG. 7 shows proline, soluble sugars, protein and total nitrogen contents of leaves and roots from wild-type plants grown at 10 mM NaCl (black bars); and transgenic plants ($X1OE_1$) grown at 10 mM NaCl (white bars) and 200 mM NaCl (hatched line bars). (A) Proline content; (B) soluble sugar content; (C) total protein content; (D) total nitrogen content. Leaves and roots were collected from fifteen plants from each treatment, the material pooled in three groups and contents measured as described in Materials and Methods. Values are the Mean±S.D (n=3).

Figure 8:
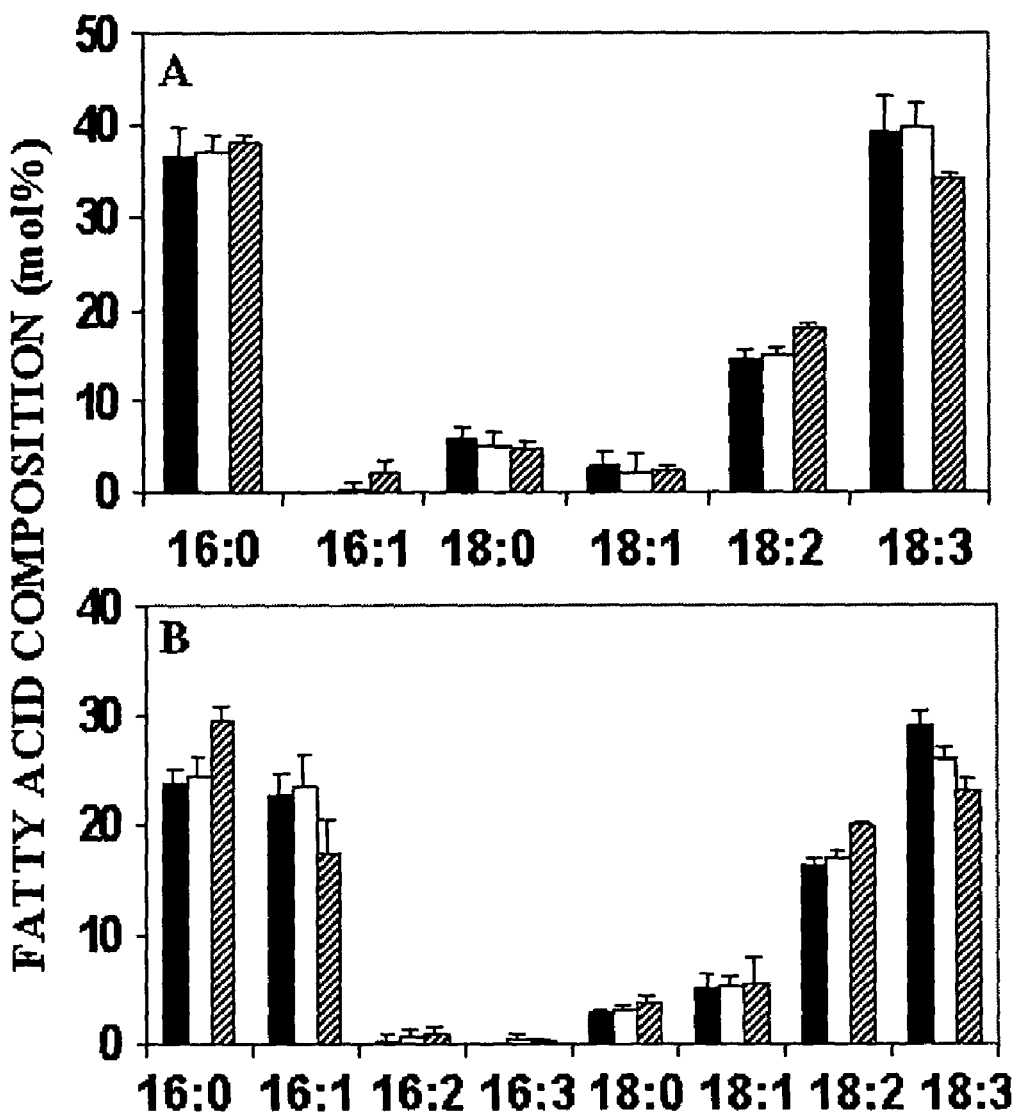

FIG. 8 shows fatty acid composition of the minor chloroplastic lipids from wild-type plants grown at 10 mM NaCl (black bars); and transgenic plants grown ($X1OE_1$) at 10 mM NaCl (white bars) and 200 mM NaCl (hatched line bars). (A) Sulfoquinovosyldiacylglycerol; (B) Phosphatidylglycerol. Leaves were collected as leaf discs from 15 plants from each treatment, the material pooled in to 3 groups of 2 g each and contents purified and measured as described in Material and Methods. Values are the Mean±S.D (n=5).

Figure 9:
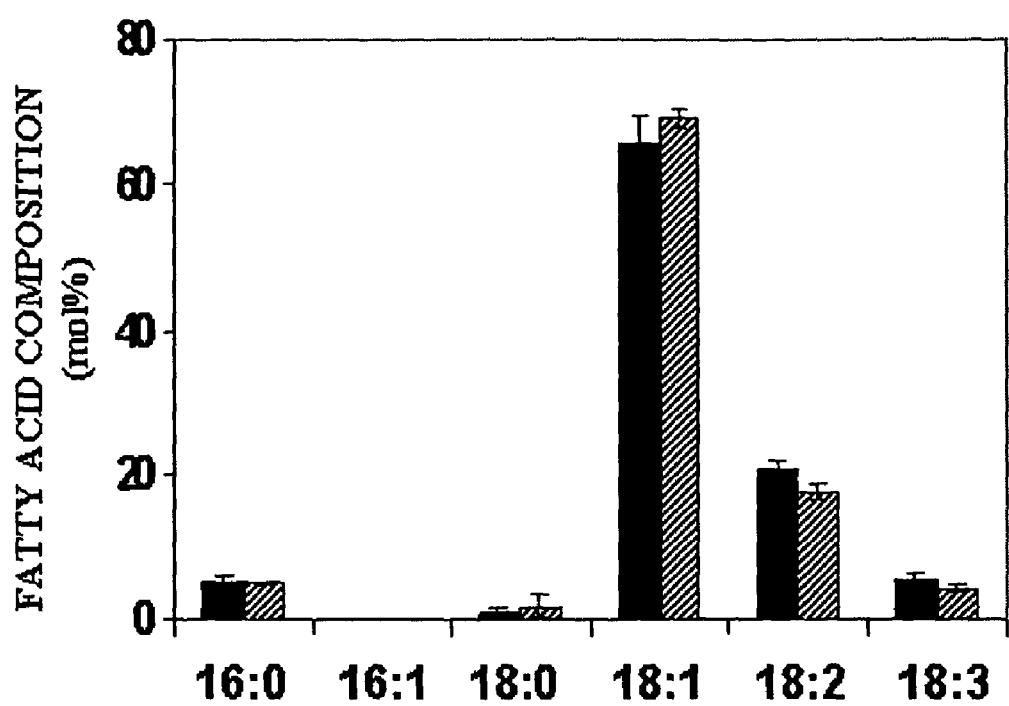

FIG. 9 shows fatty acid composition of seeds from wild-type plants grown in 10 mM NaCl (black bars) and transgenic plants ($X1OE_1$) grown in the presence of 200 mM NaCl (hatched line bars). Seeds were collected from individual plants and batches of 3 seeds per plant were used for each measurement. Values are the Mean±S.D (n=5).

BRIEF DESCRIPTION OF THE TABLES

Table I shows a comparison of the yield of a non-naturally occurring salt tolerant oil crop in the presence of 10 mM NaCl and 200 mM NaCl and the yield of the naturally occurring oil crop of the same variety grown in the presence of 10 mM NaCl.

Table II shows the a comparison of the lipid content of leaves and roots of a non-naturally occurring salt tolerant oil crop grown in the presence of 10 mM and 200 mM NaCl and a naturally occurring oil crop of the same variety grown in the presence of 10 mM NaCl.

Table III shows a representative list of NXH related gene products.

Table IV shows the plant and fruit yield of a non-naturally occurring non-halophyte tomato plant grown in the presence of 5 mM and 200 mM NaCl and a naturally occurring non-halophyte tomato plant of the same variety grown in the presence of 5 mM NaCl.

Table V shows the salinity levels that lead to a 25% relative decrease in yield and a 50% relative decrease in yield for various crop plants, including soybean, an oil crop plant.

DETAILED DESCRIPTION OF THE INVENTION

The present invention provides a non-naturally occurring plant that is characterized by increased salt tolerance due to sequestering salt in the vacuole. A preferred method of generating such plants is by ectopic expression of a nucleic acid molecule encoding an NHX related gene product that finds use in bioremediation. The NHX related gene product can have, for example, substantially the amino acid sequence of an NHX ortholog such as those described in Table III.

In one embodiment, the invention provides a transgenic plant characterized by increased salt tolerance due to ectopic expression of an exogenous nucleic acid molecule encoding an NHX-related gene product. The nucleic acid molecule encoding the NHX-related gene product can be operatively linked to an exogenous regulatory element such as a constitutive regulatory element or crop-selective regulatory element.

The present invention is directed to the surprising discovery that the NHX increases salt tolerance in plants. As disclosed herein, transgenic Brassica plants overexpressing AtNHX1 were able to grow, flower and produce seeds in the presence of 200 mM NaCl. Furthermore, as disclosed in Example 2, Lycopersicon esculentum plants overexpressing AtNHX1 were also able to grow, flower and produce fruit in the presence of 200 mM NaCl. The fruit produced had near normal levels of sodium and was thus suitable for commercial sale.

As further disclosed herein, overexpression of AtNHX1 in Brassica plants results in increased salt tolerance as compared to the salt tolerance of naturally occurring Brassica plants. As set forth in the Examples, constitutive expression of NHX1 under control of a 35 S promoter resulted in plants having increased salt tolerance as compared to the salt tolerance of naturally occurring plants. In view of the presence and expression of the NHX ortholog, as detailed in Table III, the skilled artisan will recognize that an NHX-related gene product, such as an ortholog of NHX, can be used in the methods of the present invention, for example, to produce transgenic plants having the characteristics disclosed herein. Thus, the invention provides a non-naturally occurring plant such as a transgenic Brassica plant, characterized by increased salt tolerance due to ectopic expression of a nucleic acid molecule encoding an NHX related gene product.

As used herein, the term "non-naturally occurring," when used in reference to a plant, means a plant that has been genetically modified by human intervention. A transgenic plant of the invention, for example, is a non-naturally occurring plant that contains an exogenous nucleic acid molecule, such as a nucleic acid molecule encoding an NHX-related gene product and, therefore, has been genetically modified by human intervention. In addition, a plant that contains, for example, a mutation in an endogenous NHX-related gene product regulatory element or coding sequence as a result of calculated exposure to a mutagenic agent, such as a chemical mutagen, or an "insertional mutagen," such as a transposon, also is considered a non-naturally occurring plant, since it has been genetically modified by human intervention. Furthermore, a plant generated by cross breeding different strains and varieties are also considered a "non-naturally occurring plant," because the selection and breeding is performed by human intervention. In contrast, a plant containing only spontaneous or naturally occurring mutations is not a "non-naturally occurring plant" as defined herein and, therefore, is not encompassed within the invention. Wild type plants are examples of naturally occurring plants. One skilled in the art understands that, while a non-naturally occurring plant typically has a nucleotide sequence that is altered as compared to a similar naturally occurring plant, a non-naturally occurring plant also can be genetically modified by human intervention without altering its nucleotide sequence, for example, by modifying its methylation pattern.

The term "ectopically," as used herein in reference to expression of a nucleic acid molecule, refers to an expression pattern in a non-naturally occurring plant that is distinct from the expression pattern in a comparable naturally occurring plant. Thus, one skilled in the art understands that ectopic expression of a nucleic acid molecule encoding an NHX-related gene product can refer to expression in a cell type other than a cell type in which the nucleic acid molecule normally is expressed, or at a time other than a time at which the nucleic acid molecule normally is expressed, or at a level other than the level at which the nucleic acid molecule normally is expressed. For example, under control of a constitutive promoter such as the cauliflower mosaic virus 35S promoter, NHX is expressed is expressed at higher than normal levels in plants and, thus, is ectopically expressed.

The term "increased salt tolerance," as used herein in reference to a non-naturally occurring plant variety of the invention, means a significantly increased salt tolerance as compared to the salt tolerance of a corresponding plant variety lacking a genetic modification introduced by human intervention such as an ectopically expressed nucleic acid molecule encoding an NHX-related gene product. As disclosed herein in the Examples, transgenic Brassica napus plants and transgenic tomato plants ectopically expressing NHX-1 (both examples of non-naturally occurring plants) have an increased salt tolerance as compared to naturally occurring Brassica plants and naturally occurring tomato plants, respectively.

It is recognized that there can be natural variation in the salt tolerance of a particular plant species or variety. However, the salt tolerance of a plant using a method of the invention readily can be identified by sampling a population of the plant and determining that the normal distribution of salt tolerance is higher, on average, than the normal distribution of a plant lacking an ectopically expressed nucleic acid molecule encoding an NHX-related gene product. Thus, production of non-naturally occurring plant varieties of the invention provides a means to skew the normal distribution of salt tolerance of a plant, such that the salt tolerance is, on average, at least about 5% greater, 10% greater, 20% greater, 30% greater, 50% greater, 75% greater, 100% greater, 200% greater, 300% greater, 400% greater or 500% greater than in the corresponding naturally plant variety.

The term "elevated level of sodium" in vacuoles within a plant tissue, as used herein in reference to a non-naturally occurring plant variety of the invention, means an increased concentration of sodium in the vacuole and not the cytoplasm as compared to the salt concentration of a corresponding plant variety under the same salinity and lacking a genetic modification introduced by human intervention such as an ectopically expressed nucleic acid molecule encoding an NHX-related gene product. As disclosed herein in the Examples, transgenic *Brassica napus* plants and transgenic tomato plants ectopically expressing NHX-1 sequester sodium in the vacuoles of their root and leaf tissue and thus have elevated levels of sodium as compared to naturally occurring *Brassica* plants and naturally occurring tomato plants, respectively.

It is recognized that there can be natural variation in the salt levels of a particular plant species or variety in the cytoplasm and vacuole. However, the relative salt concentrations within a plant using a method of the invention can be identified by sampling a population of the plant and determining that the ratio of salt in the vacuole as compared to the cytoplasm is higher, on average, than the ratio in a naturally occurring plant of the same variety. See for example Carden et al. (2001) and Carden et al. (2003). Thus, production of non-naturally occurring plant varieties of the invention provides a means to skew the normal distribution of salt between the vacuole and the cytoplasm when grown under increased salt conditions, such that the ratio of sodium in the vacuole to sodium in the cytoplasm is, on average, at least about 5% greater, 10% greater, 20% greater, 30% greater, 50% greater, 75% greater, 100% greater, 200% greater, 300% greater, 400% greater or 500% greater than in the corresponding naturally occurring plant variety.

The term "enhanced sodium levels" in vacuoles within a plant tissue, as used herein in reference to a non-naturally occurring plant variety of the invention, means an increased concentration of sodium in the vacuole and not the cytoplasm as compared to the salt concentration of the same plant variety grown in low to moderate salinity. As disclosed herein in the Examples, transgenic *Brassica napus* plants and transgenic tomato plants ectopically expressing NHX-1 sequester sodium in the vacuoles of their root and leaf tissue and thus have enhanced levels of sodium when grown at 200 mM NaCl as compared to the same transgenic plants grown at 10 mM NaCl.

It is recognized that there can be natural variation in the salt levels of a particular plant species or variety in the cytoplasm and vacuole. However, the relative salt concentrations within a plant using a method of the invention can be identified by sampling a population of the plant and determining that the ratio of salt in the vacuole as compared to the cytoplasm is higher, on average, than the ratio in a naturally occurring plant of the same variety. See for example Carden et al. (2001) and Carden et al. (2003). Thus, production of non-naturally occurring plant varieties of the invention provides a means to skew the normal distribution of salt between the vacuole and the cytoplasm when grown under increased salt conditions, such that the ratio of sodium in the vacuole to sodium in the cytoplasm is, on average, at least about 5% greater, 10% greater, 20% greater, 30% greater, 50% greater, 75% greater, 100% greater, 200% greater, 300% greater, 400% greater or 500% greater than in the same plant grown under low to moderate salt conditions.

The term "non-halophyte," as used herein means a plant that is not naturally morphologically and/or physiologically adapted to grow in salt rich soils or salt laden air. A non-halophyte is a plant variety that has a relative yield decrease of 50% or more at 200 mM NaCl (the equivalent of about 20 dS/m) when compared to the plant variety grown at optimal salinity levels which are below 200 mM NaCl. For the avoidance of doubt, a non-naturally occurring non-halophyte may have a relative yield decrease of less than 50% in the presence of 200 mM NaCl due to the human introduced genetic modification of the plant. The essential part of the definition is that the plant does not naturally tolerate salinity well. The invention is suitable for even more salt sensitive naturally occurring plant varieties which have a relative yield decrease of 50% or more at 180 mM NaCl, 160 mM NaCl, 140 mM NaCl, 120 mM NaCl, 100 mM NaCl or 80 mM NaCl. Table IV lists the relative yield decrease for various non-halophyte crop plants.

The term "saline-intolerant plants" as used herein means a plant variety that cannot complete its life cycle in growth media containing a salinity level above 200 mM NaCl. The invention is suitable for even more highly saline-intolerant plant varieties that cannot complete their life cycle in growth media containing a salinity level above 180 mM NaCl, 160 mM NaCl, 140 mM NaCl, 120 mM NaCl, 100 mM NaCl and even 7 mM NaCl.

Methods of Making the Plants

The following methods are illustrative of some of the methods that may be used to make the plants of the present invention. With the Examples herein, one of skill in the art will now recognize that many methods may be used to generate the non-naturally occurring plants of the present invention based upon dealing with salt accumulation in the cytosol by sequestering the salt in the plant's vacuole. A preferred method is generating a plant ectopically expressing an NHX-related gene product targeted to the plant's vacuole. From this disclosure, it will now be apparent that any sodium transporter may be used by the addition of targeting sequences that result in localization to the vacuolar membrane.

As used herein, the term "NHX-related gene product" means a gene product that has the same or similar function as At NHX such that, when ectopically expressed in a plant, normal salt tolerance is altered such that plants with increased salt tolerance are produced. *Arabidopsis* NHX-1 is an example of an NHX-related gene product as defined herein.

An NHX-related gene product generally is characterized, in part, as containing a putative cation binding domain and an amiloride binding domain. An NHX-related gene product also generally is characterized by having an amino acid sequence that has at least about 40% amino acid identity with the amino acid sequence of *Arabidopsis* NHX-1. An NHX-related gene product can have, for example, an amino acid sequence with greater than about 45% amino acid sequence identity with *Arabidopsis* NHX-1, preferably greater than about 50% amino acid identity with *Arabidopsis* NHX-1, more preferably greater than about 55% amino acid sequence identity with *Arabidopsis* NHX-1, preferably greater than about 60% amino acid identity with *Arabidopsis* NHX-NX-1, preferably greater than about 65% amino acid sequence identity with *Arabidopsis* NHX-1, preferably greater than about 75% amino acid identity with *Arabidopsis* NHX-1, more preferably greater than about 85% amino acid identity with *Arabidopsis* NHX-1, and can be a sequence having greater than about 90%, 95% or 97% amino acid identity with *Arabidopsis* NHX-1.

Preferably, an NHX-related gene product is orthologous to the plant species in which it is ectopically expressed. A nucleic acid molecule encoding *Brassica* NHX, for example, can be ectopically expressed in a *Brassica* plant to produce a non-naturally occurring *Brassica* variety characterized by an increased salt tolerance. Similarly, a nucleic acid molecule encoding oil plant NHX, for example, can be ectopically expressed in a plant to produce a non-naturally occurring plant characterized by producing salt tolerant plants.

A nucleic acid molecule encoding an NHX-related gene product also can be ectopically expressed in a heterologous plant to produce a non-naturally occurring plant characterized by an increased salt tolerance. NHX proteins have been cloned from a number of plant species (including monocots such as *Arabidopsis*, tomato, sugar beets, petunia, as well as monocots such as rice (see e.g. U.S. application Ser. No. 09/888,035, filed Jun. 22, 2001, herein incorporated by reference), etc.) indicating that they are widely conserved throughout the plant species. NHX-related gene products such as NHX orthologs also can be conserved and can function across species boundaries to result in an increased salt tolerance. Thus, ectopic expression of a nucleic acid molecule encoding NHX in a heterologous plant can alter the salt tolerance of the plant. Furthermore, a nucleic acid molecule encoding a vacuole targeted NHX-related gene product, for example, can be ectopically expressed in more distantly related heterologous plants, including plants, and, upon ectopic expression, can alter salt tolerance.

As used herein, the term "NHX-related gene product" encompasses an active segment of an NHX-related gene product, which is a polypeptide portion of an NHX-related gene product that, when ectopically expressed, increases salt tolerance. An active segment can be, for example, an amino terminal, internal or carboxy terminal fragment of NHX-1 that, when ectopically expressed in a plant, results in an increased salt tolerance. The skilled artisan will recognize that a nucleic acid molecule encoding an active segment of an NHX-related gene product can be used to generate a plant of the invention characterized by an increased salt tolerance and in the related methods and kits of the invention described further below.

An active segment of an NHX-related gene product can be identified using the methods described in The Example or using other routine methodology. Briefly, a plant such as *Brassica napus* can be transformed with a nucleic acid molecule under control of a constitutive regulatory element such as a tandem CaMV 35S promoter. Biochemical analysis of the plant and plant growth observations reveals whether a plant ectopically expressing a particular polypeptide portion has an increased salt tolerance. For analysis of a large number of polypeptide portions of an NHX-related gene product, nucleic acid molecules encoding the polypeptide portions can be assayed in pools, and active pools subsequently subdivided to identify the active nucleic acid molecule.

In one embodiment, the invention provides a non-naturally occurring plant that is characterized by an increased salt tolerance due to ectopic expression of a nucleic acid molecule encoding an NHX-related gene product having substantially the amino acid sequence of an NHX ortholog. As used herein, the term "NHX ortholog" means an ortholog of *Arabidopsis* NHX-1 and refers to an NHX-related gene product that, in a particular plant variety, has the highest percentage homology at the amino acid level to *Arabidopsis* NHX-1. An NHX-1 ortholog can be, for example the NHX-1 orthologs described in Table III. Novel NHX ortholog cDNAs can be isolated from additional plant species using a nucleotide sequence as a probe and methods well known in the art of molecular biology (Glick and Thompson (eds.), Methods in Plant Molecular Biology and Biotechnology, Boca Raton, Fla.: CRC Press (1993); Sambrook et al. (eds.), Molecular Cloning: A Laboratory Manual (Second Edition), Plainview, N.Y.: Cold Spring Harbor Laboratory Press (1989), each of which is incorporated herein by reference).

As used herein, the term "substantially the amino acid sequence," when used in reference to an NHX ortholog, is intended to mean a polypeptide or polypeptide segment having an identical amino acid sequence, or a polypeptide or polypeptide segment having a similar, non-identical sequence that is considered by those skilled in the art to be a functionally equivalent amino acid sequence. For example, an NHX-related gene product having substantially the amino acid sequence of *Arabidopsis* NHX-1 can have an amino acid sequence identical to the sequence of *Arabidopsis* NHX-1, or a similar, non-identical sequence that is functionally equivalent. In particular, a gene product that has "substantially the amino acid sequence" of an NHX ortholog can have one or more modifications such as amino acid additions, deletions or substitutions, including conservative or non-conservation substitutions, relative to the NHX-1 amino acid sequence, for example, provided that the modified polypeptide retains substantially the ability to increase salt tolerance when the nucleic acid molecule is ectopically expressed in the plant. Comparison of sequences for substantial similarity can be performed between two sequences of any length and usually is performed with sequences between about 6 and 1200 residues, preferably between about 10 and 100 residues and more preferably between about 25 and 35 residues. Such comparisons for substantial similarity are performed using methodology routine in the art.

The preferred percentage of sequence similarity for sequences of NHX orthologs includes nucleotide sequences having at least about: 48% similarity to SEQ ID NO:1. The similarity may also be at least about: 60% similarity, 75% similarity, 80% similarity, 90% similarity, 95% similarity, 97% similarity, 98% similarity, 99% similarity, or more preferably at least about 99.5%/o similarity, wherein the polypeptide has Na+/H+ transporter activity. The invention also includes salt tolerant plants made by transgenic expression of nucleic acid molecules encoding polypeptides, with the polypeptides having at least about: at least about: 48% similarity to SEQ ID NO:2. The similarity may also be at least about: 60% similarity, 75% similarity, 80% similarity, 90% similarity, 95% similarity, 97% similarity, 98% similarity, 99% similarity, or more preferably at least about 99.5% similarity, wherein the polypeptide $Na^+/H+$ has transporter activity, to SEQ ID NO:2 (or a partial sequence thereof) considering conservative amino acid changes, wherein the polypeptide has Na+/H+ transporter activity. Sequence similarity is preferably calculated as the number of similar amino acids in a pairwise alignment expressed as a percentage of the shorter of the two sequences in the alignment. The pairwise alignment is preferably constructed using the Clustal W program, using the following parameter settings: fixed gap penalty=10, floating gap penalty=10, protein weight matrix=BLOSUM62. Similar amino acids in a pairwise alignment are those pairs of amino acids which have positive alignment scores defined in the preferred protein weight matrix (BLOSUM62). The protein weight matrix BLOSUM62 is considered appropriate for the comparisons described here by those skilled in the art of bioinformatics. (The reference for the clustal w program (algorithm) is Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680; and the reference for BLOSUM62 scoring matrix is Henikoff, S. and Henikoff, J. G. (1993) Performance evaluation of amino acid substitution matrices. Proteins, 7:49-61.)

It is understood that minor modifications of primary amino acid sequence can result in an NHX-related gene product that has substantially equivalent or enhanced function as compared to the NHX ortholog from which it was derived. Further, various molecules can be attached to an NHX ortholog or active segment thereof, for example, other polypeptides, antigenic or other peptide tags, carbohydrates, lipids, or chemical moieties. Such modifications are included within the term NHX ortholog as defined herein.

One or more point mutations can be introduced into a nucleic acid molecule encoding an NHX ortholog to yield a modified nucleic acid molecule using, for example, site-directed mutagenesis (see Wu (Ed.), Meth. In Enzymol. Vol. 217, San Diego: Academic Press (1993); Higuchi, "Recombinant PCR" in Innis et al. (Ed.), PCR Protocols, San Diego: Academic Press, Inc. (1990), each of which is incorporated herein by reference). Such mutagenesis can be used to introduce a specific, desired amino acid insertion, deletion or substitution; alternatively, a nucleic acid sequence can be synthesized having random nucleotides at one or more predetermined positions to generate random amino acid substitutions. Scanning mutagenesis also can be useful in generating a modified nucleic acid molecule encoding substantially the amino acid sequence of an NHX ortholog.

Modified nucleic acid molecules can be routinely assayed for the ability to alter normal plant development such that salt tolerance is increased. For example, a nucleic acid molecule encoding substantially the amino acid sequence of an NHX ortholog can be ectopically expressed, for example, using a constitutive regulatory element such as the CaMV 35S promoter or using a tissue-specific regulatory element such as a seed-selective regulatory element as described further below. If such ectopic expression results in a seed plant in which seeds of increased size are produced, the modified polypeptide or segment is an "NHX ortholog" as defined herein.

Other functional equivalent forms of the NHX-related gene product encoding nucleic acids can be identified using conventional DNA-DNA or DNA-RNA hybridization techniques. These nucleic acid molecules and the AtNHX sequences can be modified without significantly affecting their activity.

The plants of the present invention may therefore also be made by generating transgenic plants containing nucleic acid molecules that hybridize to one SEQ ID NO:1 or their complementary sequences, and that encode expression for peptides or polypeptides exhibiting substantially equivalent activity as that of an AtNHX polypeptide produced by SEQ ID NO:1 or their variants. Such nucleic acid molecules preferably hybridize to the sequences under low, moderate (intermediate), or high stringency conditions. (see Sambrook et al. (Most recent edition) Molecular Cloning: A Laboratory Manual, Cold Spring Harbor Laboratory Press, Cold Spring Harbor, N.Y.).

As used herein, the phrase "low stringency hybridization conditions" refers the following conditions and equivalents thereto: hybridization at 5×SSC, 2% SDS, and 100 µg/ml single stranded DNA at 40° C. for 8 hours, followed by at least one wash in 2×SSC, 0.2% SDS, at 40° C. for thirty minutes.

As used herein, the phrase "moderate stringency hybridization conditions" refers the following conditions and equivalents thereto: hybridization at 5×SSC, 2% SDS, and 100 µg/ml single stranded DNA at 50° C. for 8 hours, followed by at least one wash in 0.1×SSC, 0.1% SDS, at 50° C. for thirty minutes.

As used herein, the phrase "high stringency hybridization conditions" refers the following conditions and equivalents thereto: hybridization at 5×SSC, 2% SDS, and 100 µg/ml single stranded DNA at 65° C. for 8 hours, followed by at least one wash in 0.1×SSC, 0.1% SDS, at 65° C. for thirty minutes.

The invention also provides a transgenic plant that is characterized by increased salt tolerance resulting from ectopic expression of an exogenous nucleic acid molecule encoding an NHX-related gene product targeted to plant vacuoles. In a transgenic plant of the invention, the ectopically expressed exogenous nucleic acid molecule encoding an NHX-related gene product can be operatively linked to an exogenous regulatory element. In one embodiment, the invention provides a transgenic plant characterized by increased salt tolerance having an ectopically expressed exogenous nucleic acid molecule encoding an NHX-related gene product that is operatively linked to a constitutive regulatory element. The invention provides, for example, a transgenic plant that is characterized by an increased salt tolerance due to ectopic expression of an exogenous nucleic acid molecule encoding substantially the amino acid sequence of an NHX ortholog operatively linked to a cauliflower mosaic virus 35S promoter.

In another embodiment, an exogenous constitutive or inducible regulatory element may be introduced to the plant such that the exogenous regulatory element is operably linked to an endogenous gene and alters the expression pattern of the gene in a manner that provides salt tolerance due to sequestering salt in the vacuole. One example of this would be to transfect a plant with the cauliflower mosaic virus 35S promoter such that the promoter integrates in a way that it is operably linked to one of the plant's endogenous NHX-related genes.

In yet another embodiment, an exogenous NHX-related gene may be introduced to the plant such that the exogenous NHX-related gene is operably linked to an endogenous regulatory element which directs the expression of the gene in a manner that provides salt tolerance due to sequestering salt in the vacuole. One example of this would be to transfect a plant with the atNHX1 gene such that the gene integrates in a way that it is operably linked to one of the plant's endogenous strong promoters.

As used herein, the term "transgenic" refers to a plant that contains an exogenous nucleic acid molecule, which can be derived from the same plant species or from a heterologous plant species.

The term "exogenous," as used herein in reference to a nucleic acid molecule and a transgenic plant, means a nucleic acid molecule originating from outside the plant. An exogenous nucleic acid molecule can have a naturally occurring or non-naturally occurring nucleotide sequence. One skilled in the art understands that an exogenous nucleic acid molecule can be a heterologous nucleic acid molecule derived from a different plant species than the plant into which the nucleic acid molecule is introduced or can be a nucleic acid molecule derived from the same plant species as the plant into which it is introduced.

The term "operatively linked," as used in reference to a regulatory element and a nucleic acid molecule, such as a nucleic acid molecule encoding an NHX-related gene product, means that the regulatory element confers regulated expression upon the operatively linked nucleic acid molecule. Thus, the term "operatively linked," as used in reference to an exogenous regulatory element such as a constitutive regulatory element and a nucleic acid molecule encoding an NHX-related gene product, means that the constitutive regulatory element is linked to the nucleic acid molecule encoding an NHX-related gene product such that the expression pattern of the constitutive regulatory element is conferred upon the nucleic acid molecule encoding the NHX-related gene product. It is recognized that a regulatory element and a nucleic acid molecule that are operatively linked have, at a minimum, all elements essential for transcription, including, for example, a TATA box.

As used herein, the term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types.

A variety of constitutive regulatory elements useful for ectopic expression in a transgenic plant of the invention are well known in the art. The cauliflower mosaic virus 35S (CaMV 35S) promoter, for example, is a well-characterized constitutive regulatory element that produces a high level of expression in all plant tissues (Odell et al., Nature 313:810-812 (1985)). The CaMV 35S promoter can be particularly useful due to its activity in numerous diverse plant species (Benfey and Chua, Science 250:959-966 (1990); Futterer et al., Physiol. Plant 79:154 (1990); Odell et al., supra, 1985). A tandem 35S promoter, in which the intrinsic promoter element has been duplicated, confers higher expression levels in comparison to the unmodified 35S promoter (Kay et al., Science 236:1299 (1987)). Other constitutive regulatory elements useful for ectopically expressing a nucleic acid molecule encoding an NHX-related gene product in a transgenic plant of the invention include, for example, the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

Additional constitutive regulatory elements including those for efficient ectopic expression in monocots also are known in the art, for example, the pEmu promoter and promoters based on the rice Actin-1 5' region (Last et al., Theor. Appl. Genet. 81:581 (1991); Mcelroy et al., Mol. Gen. Genet. 231:150 (1991); Mcelroy et al., Plant Cell 2:163 (1990)). Chimeric regulatory elements, which combine elements from different genes, also can be useful for ectopically expressing a nucleic acid molecule encoding an NHX-related gene product (Comai et al., Plant Mol. Biol. 15:373 (1990)). One skilled in the art understands that a particular constitutive regulatory element is chosen based, in part, on the plant species in which a nucleic acid molecule encoding an NHX-related gene product is to be ectopically expressed and on the desired level of expression.

An exogenous regulatory element useful in a transgenic plant of the invention also can be an inducible regulatory element, which is a regulatory element that confers conditional expression upon an operatively linked nucleic acid molecule, where expression of the operatively linked nucleic acid molecule is increased in the presence of a particular inducing agent or stimulus as compared to expression of the nucleic acid molecule in the absence of the inducing agent or stimulus. Particularly useful inducible regulatory elements include copper-inducible regulatory elements (Mett et al., Proc. Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Roder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible regulatory elements (Takahashi et al., Plant Physiol. 99:383-390 (1992); Yabe et al., Plant Cell Physiol. 35:1207-1219 (1994); Ueda et al., Mol. Gen. Genet. 250:533-539 (1996)); and lac operon elements, which are used in combination with a constitutively expressed lac repressor to confer, for example, IPTG-inducible expression (Wilde et al., EMBO J. 11:1251-1259 (1992)).

An inducible regulatory element useful in the transgenic plants of the invention also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)). Additional inducible regulatory elements include salicylic acid inducible regulatory elements (Uknes et al., Plant Cell 5:159-169 (1993); Bi et al., Plant J. 8:235-245 (1995)); plant hormone-inducible regulatory elements (Yamaguchi-Shinozaki et al., Plant Mol. Biol. 15:905 (1990); Kares et al., Plant Mol. Biol. 15:225 (1990)); and human hormone-inducible regulatory elements such as the human glucocorticoid response element (Schena et al., Proc. Natl. Acad. Sci. USA 88:10421 (1991)).

It should be recognized that a non-naturally occurring plant of the invention, which contains an ectopically expressed nucleic acid molecule encoding an NHX-related gene product, also can contain one or more additional modifications, including naturally and non-naturally occurring mutations that can, for example, increase salt tolerance.

The invention further provides a method of producing a non-naturally occurring plant characterized by an increased salt tolerance. The method is practiced by ectopically expressing a nucleic acid molecule encoding an NHX-related gene product in the plant, whereby salt tolerance is increased due to ectopic expression of the nucleic acid molecule. In one embodiment, the method is practiced by introducing an exogenous nucleic acid molecule encoding an NHX-related gene product into the plant.

As discussed above, the term "ectopically" refers to expression of a nucleic acid molecule encoding an NHX-related gene product in a cell type other than a cell type in which the nucleic acid molecule is normally expressed, at a time other than a time at which the nucleic acid molecule is normally expressed or at an expression level other than the level at which the nucleic acid molecule normally is expressed.

Actual ectopic expression of an NHX-related gene product is dependent on various factors. The ectopic expression can be widespread expression throughout most or all plant tissues or can be expression restricted to a small number of plant tissues, and can be achieved by a variety of routine techniques. Mutagenesis, including seed or pollen mutagenesis, can be used to generate a non-naturally occurring plant, in which a nucleic acid molecule encoding an NHX-related gene product is ectopically expressed. Ethylmethane sulfonate (EMS) mutagenesis, transposon mediated mutagenesis or T-DNA mediated mutagenesis also can be useful in ectopically expressing an NHX-related gene product to produce a seed plant that produces seeds of increased size (see, generally, Glick and Thompson, supra, 1993). While not wishing to be bound by any particular mechanism, ectopic expression in a mutagenized plant can result from inactivation of one or more negative regulators of NHX, for example.

Ectopic expression of an NHX-related gene product also can be achieved by expression of a nucleic acid molecule encoding an NHX-related gene product from a heterologous regulatory element or from a modified variant of its own promoter. Heterologous regulatory elements include constitutive regulatory elements, which result in expression of the NHX-related gene product in a limited number of plant tissues.

Ectopic expression of a nucleic acid molecule encoding an NHX-related gene product can be achieved using an endogenous or exogenous nucleic acid molecule encoding an NHX-related gene product. A recombinant exogenous nucleic acid molecule can contain a heterologous regulatory element that is operatively linked to a nucleic acid sequence encoding an NHX-related gene product. Methods for producing the desired recombinant nucleic acid molecule under control of a heterologous regulatory element and for producing a non-naturally occurring plant of the invention are well known in the art (see, generally, Sambrook et al., supra, 1989; Glick and Thompson, supra, 1993).

An exogenous nucleic acid molecule can be introduced into a plant for ectopic expression using a variety of transformation methodologies including *Agrobacterium*-mediated transformation and direct gene transfer methods such as electroporation and microprojectile-mediated transformation (see, generally, Wang et al. (eds), Transformation of Plants and Soil Microorganisms, Cambridge, UK: University Press (1995), which is incorporated herein by reference). Transformation methods based upon the soil bacterium *Agrobacterium tumefaciens* are particularly useful for introducing an exogenous nucleic acid molecule into a plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or, preferably, binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art (Glick and Thompson, supra, 1993). Wounded cells within the plant tissue that have been infected by *Agrobacterium* can develop organs de novo when cultured under the appropriate conditions; the resulting transgenic shoots eventually give rise to transgenic plants that ectopically express a nucleic acid molecule encoding an NHX-related gene product. *Agrobacterium* also can be used for transformation of plants as described in Bechtold et al., C.R. Acad. Sci. Paris. Life Sci. 316:1194-1199 (1993), which is incorporated herein by reference). *Agrobacterium*-mediated transformation is useful for producing a variety of transgenic plants (Wang et al., supra, 1995) including transgenic plants of the Brassicaceae family, such as rapeseed and flax.

Microprojectile-mediated transformation also can be used to produce a transgenic plant that ectopically expresses an NHX-related gene product. This method, first described by Klein et al. (Nature 327:70-73 (1987), which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform plants that are difficult to transform or regenerate using other methods. Microprojectile-mediated transformation has been used, for example, to generate a variety of transgenic plant species, including cotton, tobacco, corn, hybrid poplar and papaya (see Glick and Thompson, supra, 1993) as well as cereal crops such as wheat, oat, barley, sorghum and rice (Duan et al., Nature Biotech. 14:494-498 (1996); Shimamoto, Curr. Opin. Biotech. 5:158-162 (1994), each of which is incorporated herein by reference). In view of the above, the skilled artisan will recognize that *Agrobacterium*-mediated or microprojectile-mediated transformation, as disclosed herein, or other methods known in the art can be used to produce a transgenic plant of the invention.

If desired, a kit of the invention also can contain a plant expression vector. As used herein, the term "plant expression vector" means a self-replicating nucleic acid molecule that provides a means to transfer an exogenous nucleic acid molecule into a plant host cell and to express the molecule therein. Plant expression vectors encompass vectors suitable for *Agrobacterium*-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for *Agrobacterium*-mediated transformation.

In addition to containing a nucleic acid molecule encoding an NHX-related gene product operatively linked to a seed-selective regulatory element, a plant expression vector of the invention can contain, if desired, additional elements. A binary vector for *Agrobacterium*-mediated transformation contains one or both T-DNA border repeats and can also contain, for example, one or more of the following: a broad host range replicon, an ori T for efficient transfer from *E. coli* to *Agrobacterium*, a bacterial selectable marker such as ampicillin and a polylinker containing multiple cloning sites.

A plant expression vector for physical transformation can have, if desired, a plant selectable marker and can be based on a vector such as pBR322, pUC, pGEM and M13, which are commercially available, for example, from Pharmacia (Piscataway, N.J.) or Promega (Madison, Wis.). In plant expression vectors for physical transformation of a plant, the T-DNA borders or the ori T region can optionally be included but provide no advantage.

The invention will be better understood by reference to the following non-limiting examples.

EXAMPLE 1

Materials and Methods

Plant Material.

Seeds of *Brassica napus* cv. Westar were rinsed with running water for two days, surface-sterilized with a solution of 10% commercial bleach (0.525% sodium hypochlorite) and 0.1% SDS for 5 min and washed three times with sterile distilled water. Seeds were germinated on Murashige and Skoog medium (MS). Cotyledon explants were excised from 7 day-old seedlings. The binary Ti vector pBI121 was used for transformation. (Jefferson, et al. (1987)) The GUS gene of the binary vector was replaced with the AtNHX1 gene to gain the new expression construct pHZX1. The new construct was electroporated into *Agrobacterium tumefaciens* strain LBA4404. For co-cultivation, 1 ml of pHZX1 containing LBA4404 *Agrobacterium* was inoculated into 15 ml LB medium containing 50 mg.l-1 kanamycin, 50 mg.l-1 rifampicin and 200 µM acetone-syringone. The culture was incubated one day at room temperature under constant shaking (250 rpm) and then diluted one time with liquid MS medium. The cotyledon explants were submerged in the *Agrobacterium* solution for 3 min, blotted on sterile paper towels and returned to the feeder plates for 2 days of co-cultivation. After co-cultivation, the explants were transferred to a selective regeneration medium. (Moloney, et al. (1989)) Regenerated shoots were transferred to fresh medium bi-weekly. When the green shoots were 1-2 cm tall, they were separated from the calli and transferred onto rooting medium which contained modified MS medium supplemented with 3.7 mM KNO3, 4.1 mM NH4NO3, 0.5 mM MgSO4, 75 mg/l Kanamycin, 200 mg/l Ampicillin and 1 mg/l indole butyric acid. Under these conditions, about 98% shoots formed roots in two weeks. Rooted shoots were transplanted to soil, plants were grown and seeds (T1) collected. T1 seeds were grown on MS medium plates containing 15 mg/l kanamycin, plants were grown and homozygous seeds (T2) selected. For salt tolerance experiments, wild type and transgenic seeds (T2) overexpressing the vacuolar Na+/H+ antiport were germinated in 250 ml pots containing pro-mix BX peat moss, perlite and vermiculite medium (Premier Brands, New Rochelle, N.Y.) and grown in the greenhouse. Two weeks after germination the plants were watered bi-weekly with a nutrient solution with low (10 mM) or high (200 mM) concentrations of NaCl. Sixty of each wild-type and transgenic plants were distributed in two groups of thirty plants each, and each group was watered with a solution with low or high salinity. The nutrient solution was obtained by mixing 1.2 g per liter of stock fertilizer (6-11-31, Plant-Prod, Brampton, Ontario) and 1 g per liter of Ca(NO3)2. The final nutrient solution contained (in mM) 15 N, 2 P, 6.5 K, 4 Ca, 2 Mg, 9.5 S, micronutrients and was supplemented with 5 mM or 200 mM NaCl. Day temperature was maintained at 28±2° C. and night temperature was 20±2° C. Relative humidity was maintained at 50±10%. Plants were grown under a 14 h/10 h light/dark photoperiod. Supplemental lighting consisted of eight high-pressure sodium lamps, and resulted in a total flux (sunlight and supplemental light) of approximately 1,450 µmol m$^{-2}$s$^{-1}$.

Membrane Isolation and Western Blots.

Tonoplast-enriched membrane fractions were isolated from leaves of 10-week-old plants as described. (Zhang, et al. (2001)) Western blots were performed as described.

Leaf, Root and Seed Chemical and Lipid Analysis.

Roots were rinsed with distilled water and leaves and roots were collected from fifteen plants from each treatment, pooled in three groups, dried at 70° C. for 24 h and the material was ground to a fine powder. Seeds were collected from the rest of the plants 3 weeks later. For the determination of soluble sugars and proline contents, 100 mg of each pool was resuspended in 2 ml of water, sonicated and centrifuged for 10 min at 2,500×g. Soluble sugar, proline and protein contents were determined in the supernatant as described. (Blumwald, et al. (1985)); Dubois, et al. (1956) and Bates, et al. (1973)) Ion contents were determined by atomic absorption spectrophotometry. Lipids were extracted from 2 g of mature leaf tissue or 3 g of root tissue with chloroform/methanol (2; 1, v/v) and purified as previously described. (Williams, et al, (1970)) Lipid classes were separated by thin-layer chromatography (TLC) on silica gel G plates containing ammonium sulfate using acetone/benzene/water (91: 30:8, v/v). (Khan, et al. (1977)) The lipids were scraped from the plate and trans-esterified with 1 mL 1.5 M HCl in dry methanol in a microwave oven as previously described and the fatty acid methyl esters (FAME) were extracted from the methanolic HCl with hexane. (Khan, et al, (1993)) Seed oil fatty acid compositions were determined by direct trans-esterification of whole seeds using the microwave technique. The FAME were analyzed by gas-liquid chromatography using a Hewlett-Packard model 5890 gas-liquid chromatograph (Hewlett-Packard, Mississauga, Ontario, Canada) with a 30 m×0.25 mm ID DB-23 capillary column (J & W Scientific, Folsom, Calif.) programmed from 160° C. to 210° C. at 3° C. min$^{-1}$. The FAME were estimated quantitatively using methylpentadecanoate as an internal standard.

Results

A construct containing the AtNHX1 was introduced into the genome of *Brassica napus* cv Westar. Sixty-four transgenic plants were obtained and nine homozygous lines from these transgenic plants were obtained in the T2 generation (data not shown). In order to assess whether the enhanced expression of the vacuolar Na$^+$/H$^+$ antiport would allow plants to grow in high salt conditions, wild-type and three lines of transgenic plants (with relatively low, medium and high levels of transgene expression) were grown in the presence of 200 mM NaCl (FIG. 5), a concentration that inhibits the growth of almost all crop plants. The overexpression of the vacuolar Na$^+$/H$^+$ antiport did not affect the growth of the transgenic plants since similar growth was observed when the wild-type and the transgenic plants were grown in the presence of 10 mM NaCl (Table I). The growth of the wild-type plants was severely affected by the presence of 200 mM NaCl in the growth solution, plant growth was inhibited and the plants were severely stunted (FIG. 5). On the other hand, the transgenic plants grew, flowered and produced seeds (FIG. 5, Table I). The growth of the transgenic plants in 200 mM NaCl was correlated with the increased levels of AtNHX1 protein (FIG. 5). Immunoblots of membrane fractions isolated from wild-type and transgenic plants only detected AtNHX1 in the tonoplast-enriched fractions from transgenic plants indicating the proper targeting of the Na$^+$/H$^+$ antiport to the tonoplast (FIG. 5).

We determined the Na$^+$, K$^+$, soluble sugars, proline, total protein, nitrogen and phosphorus contents of wild-type and transgenic plants grown at low (10 mM) NaCl and transgenic plants grown at high (200 mM) NaCl (FIGS. 6 and 7). At low salinity, no significant differences were seen in the leaf and root Na$^+$ content from wild-type and transgenic plants (FIG. 6). Dramatic changes were seen in transgenic plants grown at high salinity. A 70- and 9-fold increase in Na$^+$ content was seen in the leaves and roots of these plants, respectively. The K$^+$ content of leaves and roots of transgenic plants growing at high salinity decreased by 75% and 82%, respectively. While the leaf soluble sugars content declined during growth at high salinity (FIG. 7), a 6-fold increase in proline content was seen in high-salt grown leaves. There were no significant differences in N (FIG. 7) or total P content (data not shown). It should be noted that a comparison with wild-type plants grown at high salinity was not possible since all of the wild-type plants grown in these conditions were dead.

The major root and leaf lipids from wild-type grown at low salinity and transgenic plants grown at low and high salinity were analyzed (Table II). No significant differences in the major chloroplastic and extraplastidic lipids were found. The fatty acid composition of the two major extraplastidic lipids, phosphatidylcholine (PC) and phosphatidylethanolamine (PE) did not differ in either the 16/18 C ratio or the degree of unsaturation (not shown). Similarly, no differences were observed in the fatty acid compositions of the chloroplastic lipids digalactosyldiacylglycerol (DGDG) and mongalactosyldi acyl glycerol (MGDG). Neither DGDG (synthesized predominantly through the eukaryotic pathway) nor MGDG (synthesized predominantly through the prokaryotic pathway) showed any significant difference in the 16/18 C ratio or degree of unsaturation (results not shown). Some differences, however, were seen in the minor chloroplastic lipids, sulfoquinovosyldiacylglycerol (SQDG) and phosphatidylglycerol (PG) (FIG. 8).

Although the 16/18 C ratios were the same, there were differences in the degree of unsaturation of the 18 C fatty acids in both SQDG and PG from transgenic plants grown in 200 mM NaCl. The ratio of palmitic acid (16:0)/trans-$\Delta^3$-hexadecenoic acid (trans16:1) in PG from transgenic plants grown in 200 mM NaCl was significantly higher than in plants grown in 10 mM NaCl.

In roots, the predominant lipids are the extraplastidic phospholipids. Although the levels of MGDG, synthesized predominantly through the eukaryotic pathway in roots, are similar to those in leaves, the other plastidic lipids are found in very low quantities in roots. There were no significant differences in the fatty acid compositions of PC, PE and MGDG from wild type and transgenic plants grown at 10 mM NaCl or 200 mM NaCl (results not shown). Total fatty acid analyses of the seed oil did not differ significantly in seeds from wild-type plants grown in 10 mM NaCl and transgenic plants grown in 200 mM NaCl (FIG. 9). Quantitatively and qualitatively the seed oil from the transgenic plants is identical with seed oil from the wild-type plants.

Discussion

Taken together, our results demonstrate the ability of the transgenic plants to utilize salty water for growth. In spite of the high $Na^+$ content in the leaves of the transgenic plants grown at 200 mM NaCl, these plants were able to grow, flower and set seed. These results clearly demonstrate that the enhanced accumulation of $Na^+$, mediated by the vacuolar $Na^+/H^+$ antiport, allowed the transgenic plants to mitigate the toxic effects of $Na^+$. (Apse, et al. (1999) and Zhang, et al (2001)) Notably, transgenic plants grown at 200 mM NaCl produced numbers of seeds similar to those of wild-type plants grown at low salinity. Moreover, qualitative and quantitative analyses of the oil content showed no significant differences between seeds from wild-type grown at low salinity and transgenic plants grown at high salinity. It should be noted that although our experiments were carried out in the greenhouse, our results were obtained under growth conditions with a relatively low humidity and high light intensity. The leaf and root $K^+$ contents of the transgenic plants grown in 200 mM NaCl were lower than those from plants grown in low salinity. Adaptation of plants to saline environments not only depends on their ability to ameliorate the toxic effects of $Na^+$ per se, but also on their ability to overcome salt-induced impaired nutrient acquisition. (Marschner (1995)) This is of particular importance with regards to $K^+$ uptake and $K^+$ homeostasis. Potassium concentrations in plant cells are kept under homeostatic control with cytosolic $K^+$ concentrations in the order of 100-200 mM. (Wyn Jones, et al. (1983)) When exposed to relatively low NaCl concentrations, $Na^+$ ions can promote growth of many plants, in particular at low $K^+$ concentrations in the growth medium. (Elzam, et al. (1969)) Under high salinity conditions, $Na^+$ ions may displace $K^+$ from its carrier binding sites and this competition results in impaired $K^+$ uptake and lower $K^+$ cytosolic concentrations. Nevertheless, the growth of the transgenic plants was not significantly affected by high salinity, suggesting that $K^+$ nutrition was not compromised in our experiments. It should be noted that we have used a high level of $K^+$ (6.5 mM) in our solutions. Transgenic plants grown in 200 mM NaCl displayed a six-fold increase in proline content compared to plants grown in low salinity. This accumulation of proline in response to high salinity is well documented. Proline contributes to osmotic adjustment, the protection of macromolecules during dehydration, and as a hydroxyl radical scavenger. (LeRudulier, et al. (1984); Yancey, et al. (1982) and Smirnoff, et al. (1989)) Evidence supporting the role of proline during salt stress was obtained on the basis of salt tolerance in transgenic tobacco plants with enhanced levels of proline biosynthesis and salt tolerance of *Arabidopsis* with suppressed levels of proline degradation. (Kishor, et al. (1995) and Nanjo, et al. (1999)) Moreover, a similar increase in proline content was observed in transgenic tomato plants overexpressing AtNHX1 growing at high salinity. (Zhang, et al. (2001))

In all plant cells there are two major sites of lipid synthesis and desaturation of fatty acids. Glycerolipids derived from diacylglycerols synthesized in the extraplastidic compartments of the cell are synthesized by the eukaryotic pathway, whereas lipids derived from diacylglycerol synthesized in plastids are produced by a prokaryotic pathway. (Browse, et al. (1991) and Williams, et al. (2000)) Each compartment possesses different isoforms of glycerol-3-phosphate acyltransferase (GPAT) and lysophosphatidic acid acyltransferase (LPAT) that show differing specificity toward the fatty acid esterified to the two sn positions of the diacylglycerol. In addition, the desaturases of these diacylglycerol are specific to the specific compartment. Thus, through analyses of fatty acid composition it is possible to determine any specific effect of stress on lipid synthesis in the cell compartments. Our data suggest that the major structural lipids of the extraplastidic compartments (PC and PE) and of the chloroplasts (DGDG and MGDG) were unaffected by the overexpression of AtNHX1 and by the growth of the transgenic plants at high salinity. Only minor changes in the chloroplast lipids, SQDG and PG, were seen in transgenic plants grown in 200 mM NaCl. Little differences in the quantity of lipid or fatty acids were detected in the structural lipids of the cell. The 16/18 C ratio remained similar, suggesting little effect on GPAT or LPAT activities. Further, the levels of unsaturation remained constant, indicating little or no effect on the desaturase activity. Only in the minor chloroplast lipids were changes in desaturation seen, the major difference being the 16:0/trans16:1 ratio in PG (1.7 and 1.0 in transgenic plants grown in 200 mM NaCl and plants grown in low salinity, respectively). Previous work has shown that this difference reflects a change in the light-harvesting complexes of the thylakoid membranes during the acclimation of plants to stress. (Huner, et al. (1987)) Our results would suggest that the transgenic plants displayed little signs of stress or acclimation to high NaCl conditions. Analyses of the seed oil show no significant difference between seeds from wild-type and transgenic plants grown at low or high salinity.

Worldwide, more than 60 million hectares of irrigated land (representing 25% of the total irrigated acreage in the world) have been damaged by salt. (Ghassemi, et al. (1995)) Twenty years ago, Epstein argued for the development of salt tolerant crops with truly halophytic responses to salinity, i.e., accumulation of salt, in which the consumable part is botanically a fruit, such as grain or berries or pomes. (Epstein (1983)) In these plants, Na$^+$ ions would accumulate mainly in their leaves, and since the water transport to the fruits and seeds is mainly symplastic much of the salt from these organs would be screened. (Ehret, et al. (1986); Lee (1986) and Davies, et al. (2000)) Our results clearly support Epstein's argument. (Epstein (1983)) These results together with the data presented here clearly demonstrate the feasibility of generating salt tolerant crops for agricultural use. Much of the effort towards breeding crop cultivars with improved salt tolerance assumed that salt tolerance will be achieved only after pyramiding several characteristics in a single genotype. (Yeo, et al. and Cuartero, et al. (1999)) However, the modification of a single trait (vacuolar Na$^+$ accumulation) significantly improved the salinity tolerance of *Brassica* plants. These results strongly suggest that with a combination of breeding and transgenic plants it could be possible to produce salt tolerant crops with far fewer introduced traits than had been anticipated.

EXAMPLE 2

Experimental Protocol

Plant Material and Transgenic Plants.

*Lycopersicon esculentum* (cv Moneymaker) seeds were germinated on Murashige and Skoog medium (MS). Cotyledon explants were excised from 7 day-old seedlings, cut in half and cultured overnight on a one day-old feeder layer consisting of 3 ml of a 7 day-old sugar beet suspension culture plated and overlaid with a sterile Whatman filter paper. The binary Ti vector pBI121 was used for transformation. The GUS gene of the binary vector was replaced with the AtNHX1 gene to gain the new expression construct pHZX1. pHZX1 was electroporated into *Agrobacterium tumefaciens* strain LBA4404. For co-cultivation, 1 ml of pHZX1 containing *Agrobacterium* were inoculated into 15 ml LB medium containing 50 mg/l kanamycin, 50 mg/l rifampicin and 200 μM acetone-syringone. After two days of co-cultivation with *Agrobacterium*, the explants were transferred to selective regeneration medium. (Thomas, et al. (1981)) Regenerated shoots were transferred to fresh medium bi-weekly. When the green shoots were 1-2 cm tall, they were separated from the calli and transferred onto rooting medium containing modified MS salts. About 98% shoots can form roots in two weeks. Rooted shoots were transplanted to soil and plants regenerated. T1 seeds were grown on plates containing MS medium and 100 mg/l kanamycin and homozygous seeds selected.

For salt tolerance experiments, wild type and two independent lines (T2) of transgenic plants were grown hydroponically. Seeds were germinated in agar plates containing MS medium under continuous light at 25° C. Two weeks after germination, sixty of each wild-type and transgenic seedlings were transferred to six hydroponic tanks, containing 20 seedlings each tank, and grown in the greenhouse. Day temperature was maintained at 26±2° C. and night temperature was 22±2° C. Relative humidity was maintained at 50±10%. Plants were grown under a 14 h/10 h light/dark photoperiod. Supplemental lighting consisted of eight high-pressure sodium lamps, and resulted in a total (sunlight and supplemental light) of approximately 1,250 μmol/m2s. The nutrient solution was obtained by mixing 1.2 g per liter of stock fertilizer (tomato fertilizer, Plant-Prod, Brampton, Ontario) and 1 g per liter of CaNO3. The final nutrient solution contained (in mg/l) 200 N, 54 P, 256 K, 147 Ca, 42 Mg, micronutrients and was supplemented with 5 mM or 200 mM NaCl. The nutrient solution was replaced every 6 days and the roots were kept under constant aeration.

Membrane Isolation and Western Blots.

Membrane fractions were isolated from shoots of 4-week-old plants or tomato fruits from mature plants as described. (Blumwald, et al (1985)) Western blots of the different membrane fractions were performed as described. (Apse, et al. (1999))

Transport Assays.

The cation/H$^+$ exchange activity was measured by following the pH dependent fluorescence quenching of acridine orange. An acidic-inside pH gradient across the tonoplast vesicles was obtained by activation of the vacuolar H$^+$-PP$_i$-ase. Twenty μg of tonoplast vesicles were added to 0.8 ml buffer containing 0.25 M Mannitol, 5 mM Tris/MES (pH 8.0), 2 mM dithiotreitol, 25 mM KCl, 0.8 mM Tris-PPi and 5 μM acridine orange. Proton translocation was initiated by the addition of 1 mM Mg$^{2+}$ and the change in fluorescence was monitored as described. (Blumwald, et al. (1985)) When a steady-state pH gradient (acidic inside) was formed, PPi-dependent H$^+$-transport activity was stopped by the addition of AMDP and the changes in rate of fluorescence recovery were determined in the presence and absence of 50 mM NaCl.

Leaf and Fruit Chemical Analysis.

Chemical analysis from 3-month old plants was performed. Fully-expanded mature leaves from the six most lower basal nodes (old leaves), developing leaves from the six most upper apical nodes (young leaves), roots and fruits were collected and dried at 70° C. for 24 h and the material ground to a fine powder. Tomatoes were collected at the mature green/red ripe stage and were allowed one week of further maturation at the bench at room temperature (22° C.) before analysis. For the determination of soluble sugars, 100 mg of each sample was resuspended in 2 ml of water, sonicated and centrifuged for 10 min at 2,500×g. Soluble sugar and proline contents were determined in the supernatant as described. (Dubois, et al. (1956) and Bates, et al. (1973)) Ion contents were determined by atomic absorption spectrophotometry and chloride content by titration. Water content was calculated as (FW-DW)/FW, where FW and DW are the fresh and dry weight, respectively. Dry weight was obtained by placing the material at 70° C. until a constant weight was obtained. For the determination of soluble solid contents, the tomatoes were strained through a 20 μm mesh and Brix readings of the juice were obtained by refractometry. Brix readings (°Brix) represent the concentrations of soluble solids as a percentage of total fresh weight.

Results and Discussion

Figure 1:
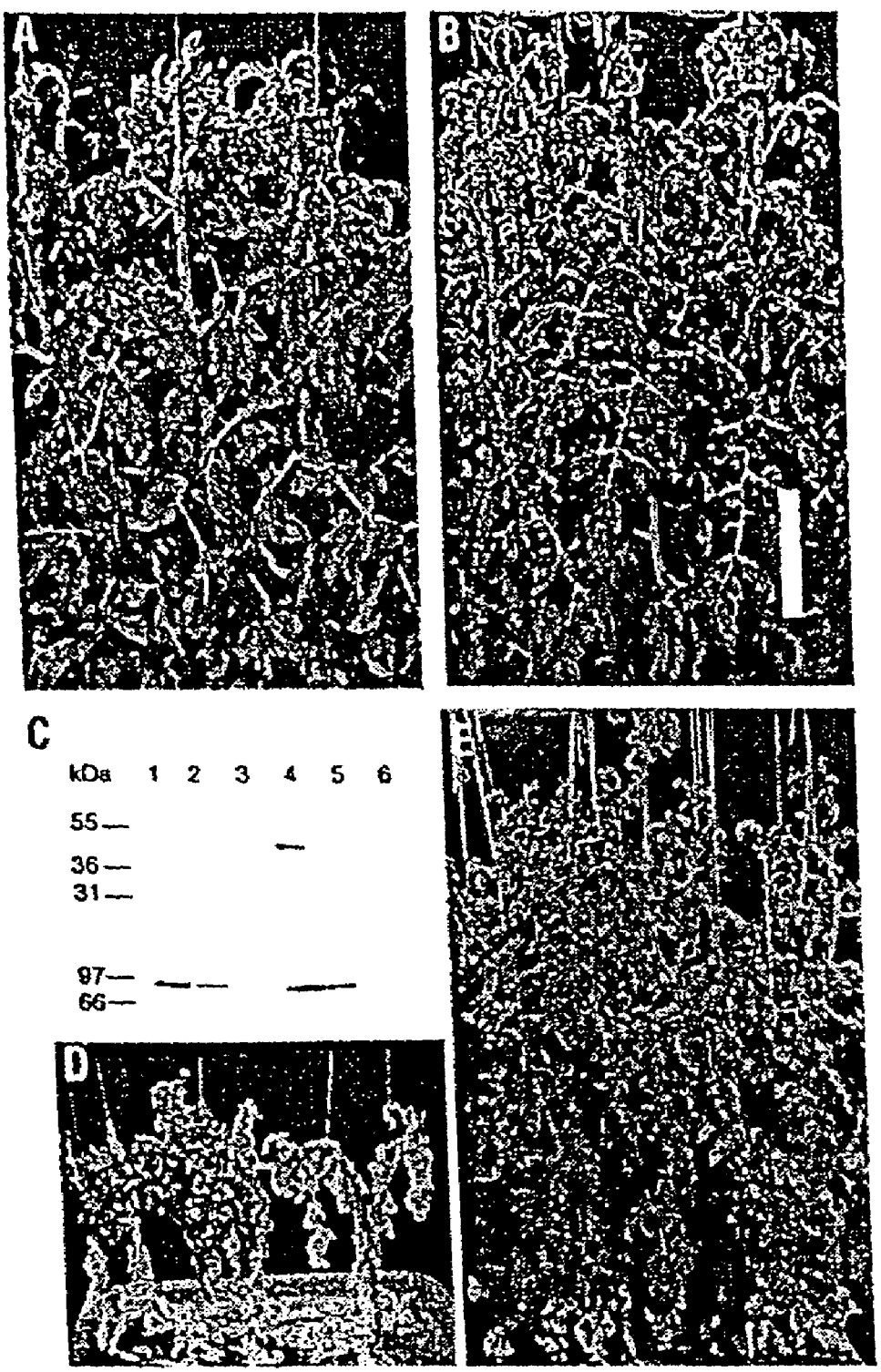
FIG. 1 shows salt tolerance of wild-type tomato plants and transgenic plants overexpressing AtNHX1 grown in the presence of 200 mM NaCl. (A) wild-type plants grown in the presence of 5 mM NaCl. (B) transgenic plants overexpressing AtNHX1, grown in the presence of 5 mM NaCl. (C) Western blots from leaf membrane proteins (5 μg) tested with antibodies raised against AtNHX1. Upper panel: Lanes 1 and 4, tonoplast-enriched fraction; lanes 2 and 5, Golgi/ER-enriched fractions; 3 and 6, plasma membrane fraction. Lanes 1, 2, 3 correspond to membranes from wild-type plants while lanes 4, 5, 6 correspond to membranes from transgenic plants. Relative molecular masses are indicated on the left; lower panel: Enrichment of the fractions with tonoplast membranes was assessed with antibodies raised against the vacuolar H+-PPiase. (D) wild-type plants grown in the presence of 200 mM NaCl. (E)) transgenic plants overexpressing AtNHX1, grown in the presence of 200 mM NaCl. Plants shown after 11 weeks of growth.

A construct containing the *Arabidopsis thaliana* AtNHX1, coding for a vacuolar Na$^+$/H$^+$ antiport, was introduced into the genome of *Lycopersicon esculentum* cv Moneymaker. Forty-seven transgenic plants were obtained and six homozygous lines from these transgenic plants were obtained in the T2 generation (data not shown). Two of these homozygous lines were used in our experiments. These two lines were chosen because they grew more vigorously in high salinity. The overexpression of the vacuolar Na$^+$/H$^+$ antiport did not affect the growth of the transgenic plants (only one line of transgenic plants is shown) since similar growth was observed when the wild-type and the transgenic plants were grown in the presence of 5 mM NaCl (FIGS. 1A,B). Immunoblots of membrane fractions isolated from wild-type and transgenic plants only detected AtNHX1 in the tonoplast-enriched fractions from transgenic plants (FIG. 1C), indicating the proper targeting of the Na$^+$/H$^+$ antiport to the vacuoles. In order to assess whether the enhanced expression of the vacuolar $Na^+/H^+$ antiport would allow plants to grow in high salt conditions, wild-type and transgenic plants were grown in the presence of 200 mM NaCl, a concentration that inhibits the growth of almost all crop plants. The growth of the wild-type plants was severely affected by the presence of 200 mM NaCl in the growth solution, plant growth was inhibited, most of the plants died or were severely stunted (FIG. 1D). On the other hand, the transgenic plants grew, flowered and produced fruit (FIG. 1E).

To confirm that the presence of the $Na^+/H^+$ antiport protein resulted in increased $Na^+/H^+$ exchange, we monitored $H^+$-dependent $Na^+$ movements in tonoplast vesicles isolated from leaves. The vesicular lumen was acidified by the activation of the vacuolar $H^+$-$PP_i$ase in the presence of $K^+$ ions, since the $H^+$-$PP_i$ase activity is $K^+$ dependent. Once the pH gradient was established, the $H^+$-pump activity was stopped by the addition of AMDP (amino-methylene-diphosphonate), NaCl was added and the rates of $Na^+/H^+$ exchange measured (FIG. 2A). Tonoplast vesicles isolated from transgenic plants displayed $Na^+/H^+$ exchange rates 7-fold higher than those from vesicles isolated from wild-type plants. Interestingly, $K^+/H^+$ exchange was also observed in the tonoplast vesicles after the addition of AMDP, in the absence of external $Na^+$, (FIG. 2B) and the rates of $K^+/H^+$ exchange were significantly higher in vesicles isolated from the transgenic plants. These results indicate that the vacuolar $Na^+/H^+$ antiport was also able to mediate $K^+/H^+$ exchange, albeit with a lower specificity for $K^+$ than for $Na^+$. $K^+$ ions are involved in a wide number of physiological processes and vacuolar pools generate the turgor needed to drive cell expansion. (Marschner (1995)) Under $K^+$ deficient growth conditions, vacuolar $K^+$ concentrations decline while the cytosolic $K^+$ concentrations remain relatively constant. (Walker, et al. (1996)) Cytosolic $K^+$ concentrations decline only when the vacuolar $K^+$ concentrations decrease to values around 20 mM. (Leigh, et al. (1984)) The decrease in cytosolic $K^+$ concentrations with the concomitant increase in cytosolic $Na^+/K^+$ ratio is the basis of cytosolic $Na^+$ toxicity. (Maathuis, et al. (1999)) Given the cytosol-negative electrical potential difference at the tonoplast, an active $K^+$ translocation mechanism into the vacuole has to be considered. Evidence of a $K^+/H^+$ antiport was found in tonoplast-enriched fractions from different plants. (Blumwald, et al. (1997)) Although the Arabidopsis sequencing project is completed, only putative $K^+/H^+$ antiports with similarity to the glutathione-regulated potassium-efflux system of E. coli have been sequenced (Accession numbers AAF78418, AAD10158, CCAB80872). (Munro, et al. (1991)) Although their putative function has not yet been characterized in plants, in bacteria and yeast these transporters function as plasma membrane-bound potassium exchangers. (Munro, et al. (1991) and Ramirez, et al. (1998) Although the role of vacuolar $Na^+/H^+$ antiports in glycophytes has yet to be established, its ubiquity in plants (Blumwald, in preparation) and its ability to mediate $K^+$ transport would suggest that the vacuolar $Na^+/H^+$ antiport could also play a role in cellular $K^+$ homeostasis.

We determined the ion, sugar, and proline contents of wild-type and transgenic plants grown at low (5 mM) NaCl and two independent transgenic lines grown at high (200 mM) NaCl (FIG. 3). It should be noted that a comparison with wild-type plants grown at high salinity was not possible since all of the wild-type plants grown in these conditions were dead. At low salinity, no significant differences were seen in the content of $Na^+$ (FIG. 3A), $K^+$ (FIG. 3B), $Cl^-$ (FIG. 3C) soluble sugars (FIG. 3D) or proline (FIG. 3D) of all tissues. Dramatic changes were seen in transgenic plants grown at high salinity. A 28- and 20-fold increase in $Na^+$ content was seen in fully developed mature (old) and developing (young) leaves, respectively (FIG. 3A), and a similar increase in $Cl^-$ content was also observed (FIG. 3C). The $K^+$ content of old leaves, young leaves and roots decreased a 5-, 2- and 4-fold, respectively (FIG. 3B). While no significant difference in soluble sugars was observed during growth in high salinity (FIG. 3D), a 3- and 5-fold increase in proline content was seen in leaves and fruits, respectively (FIG. 3E). The accumulation of proline in response to high salinity is well documented. Many prokaryotic and eukaryotic organisms accumulate proline during osmotic and salt stress. (Csonka, et al. (1991) and Schobert (1977)) Proline contributes to osmotic adjustment, the protection of macromolecules during dehydration, and as a hydroxyl radical scavenger. (LeRudulier, et al.; LeRudulier, et al. (1984) and Yancey, et al. (1982)) Evidence supporting the role of proline during salt stress was obtained based on salt tolerance in transgenic tobacco plants with enhanced levels of proline biosynthesis and salt tolerance of Arabidopsis with suppressed levels of proline degradation. (Kishor, et al. (1995) and Nanjo, et al. (1999))

Taken together, our results demonstrate the ability of the transgenic plants to utilize salty water for growth. In spite of the high $Na^+$ and $Cl^-$ content in the leaves of the transgenic plants grown at 200 mM NaCl, only a marginal increase in the $Na^+$ and $Cl^-$ content of the fruits was observed. The $K^+$ content of the leaves from transgenic plants grown in salt decreased while the $K^+$ content of the transgenic fruits was higher than the $K^+$ content of the fruits from plants grown at low salinity. These results clearly demonstrate that the enhanced accumulation of $Na^+$, mediated by the vacuolar $Na^+/H^+$ antiport, allowed the transgenic plants to ameliorate the toxic effects of $Na^+$ and the transgenic plants overcame salt-induced impaired nutrient acquisition. (Rea, et al. (1987)) Notably, transgenic plants grown in the presence of 200 mM NaCl produced fruits (FIGS. 4A, B and Table IV). While the transgenic leaves accumulated $Na^+$ to almost 1% of their dry weight, the fruits displayed only a marginal increase in $Na^+$ content and a 25% increase in $K^+$ content. The number of fruits per plant was similar, and although the fruits from the transgenic plants grown in 200 mM NaCl were somewhat smaller, no significant difference was observed in their water content or total soluble solids content (Table IV). The low $Na^+$ content of the transgenic fruits cannot be due to the lack of vacuolar $Na^+/H^+$ antiport since the protein was present in the fruit tissue (FIG. 4C). It has been demonstrated that in expanding fruit of many plant species, including tomato, more than 90% of the water transported into the fruit occurs through the phloem. (Ehret, et al. (1986); Lee (1986) and Davies, et al. (2000) Thus the ability to maintain a high cytosolic $K^+/Na^+$ concentration ratio along the symplastic pathway was most probably responsible for the low $Na^+$ content of the fruits.

Worldwide, more than 60 million hectares of irrigated land (representing 25% of the total irrigated acreage in the world) have been damaged by salt. Our findings suggests the feasibility of producing salt tolerant transgenic plants that will produce edible crops.

EXAMPLE 3

Expression of NHX-Related Gene Products in Saccharomyces cerevisiae.

Expression of NHX-related gene products in yeast is useful to assess and characterize the biochemical properties of the recombinant and native polypeptides. Expression in yeast also facilitates the study of interactions between different NHX-related gene products. Once function has been verified in yeast, the targeting to vacuoles may be verified in plants. We have made conditional expression constructs by ligating the coding region of the AtNHX1 cDNA into two vectors, pYES2 (Invitrogen) and pYEP434. Both constructs provide galactose-inducible expression, but pYES2 has a URA3 selectable marker while pYEP434 has LEU2 as a selectable marker. Transformation by lithium acetate, 1994), is followed by selection on solid media containing amino acids appropriate for the selection of cells containing the transformation vector. For integrative transformation, the YXplac series of vectors for integrative transformation are used.

The patent or application file contains at least one drawing executed in color. Copies of this patent or patent application publication with color drawing(s) will be provided by the Office upon request and payment of the necessary fee.

REFERENCES

The following references are hereby incorporated by reference.

Rush, P W and Epstein, E (1981). J. Amer. Soc. Hort. Sci. 106, 699-704.

Norlyn, J D (1980). In: Genetic Engineering of Osmoregulation (Eds. D W Rains, R C Valentine and A Hollaender) pp. 293-309. Plenum Press: New York.

Tal, M (1985). Plant & Soil 89, 199-226.

Flowers, T J and Yeo, A R (1995). Aust. J. Plant Physiol. 22, 875-884.

Bonhert, H J and Jensen, R G (1996). Aust J. Plant Physiol. 23, 661-667.

Tarcynski, M C, Jensen, R G & Bonhert, H J (1995) Science 259, 508-510.

Kishor et al. (1995). Plant Physiol. 108, 1387-1394.

Ishitani, M, et al., (1995). Plant Mol. Biol. 27, 307-317

Xu, et al. (1996) Plant Physiol. 110, 249-257.

Wu, R and Ho, T H D. Patent # WO9713843.

Jia, Z P, et al., (1992). EMBO J. 11, 1631-1640.

Young, P G & Zheng, P. J. Patent #WO9106651.

Maathuis, F J M. & Amtmann, A. (1999) Ann. Bot. 84, 123-133.

Flowers, T J, Troke, P F & Yeo, A R (1977) Annu. Rev. Plant Physiol. 28, 89-21.

Glenn, E., Brown, J. J. & Blumwald, E. (1999) Crit. Rev. Plant Sci. 18, 227-255.

Blumwald, E., Aharon, G. S. & Apse, P. (2000) Biochim. Biophys. Acta 1465, 140-151.

Shi, H., Ishitani, M., Kim, C. & Zhu, J-K. (2000). Proc. Natl. Acad. Sci. USA 97, 6896-6901.

Blumwald, E.& Poole, R. J. (1985) Plant Physiol. 78, 163-167.

Apse, M. P., Aharon, G. S., Snedden, W. S. & Blumwald, E. (1999) Science 285, 1256-1258.

Ben Raïs, L., Alpha, M.-J., Bahl, J., Guillot-Salomon, T. & Dubacq, J.-P. (1993) Plant. Physiol. Biochem. 31, 547-557

Wu, J., Seliskar, D. M. & Gallagher, J. L. (1998) Physiol. Plant. 102, 307-317

Yu, B., Gong, H. & Lui, Y. (1998) J. Plant Nutrition 21, 1589-1600

Smaoui, A. & Cherif, A. (2000) Biochem. Soc. Trans. 28, 902-905

Zhang, H-X & Blumwald, E. (2001) Nature Biotechnol. 19, 765-768

Jefferson, R. A., Kavanagh, T. A. & Bevan, M. W. (1987) EMBO J. 6, 3901-3907.

Moloney, M. M., Walker, J. M., & Sharma, K. K. (1989). Plant Cell Rep. 8, 238-242

Dubois, M., Gilles, R A., Hamilton, J K., Roberts, P A. & Smith, F. (1956) Anal. Chem. 28, 350-356.

Bates, L. S., Waldren, R. P. & Teare, I. D. (1973) Plant & Soil 39, 205-207.

Williams, J. P. & P. A. Merrilees. (1970) Lipids 5, 367-370.

Khan, M. & J. P. Williams. (1977) J. Chromatog. 140, 79-185

Khan, M. U. & J. P. Williams (1993) Lipids 28, 953-955

Marschner, H. (1995). Mineral nutrition of higher plants. (Academic Press, New York)

Wyn Jones, R G and Pollard, A (1983). in Encyclopedia of Plant Physiology, New Series Vol 15B, eds, Lauchli, A.& Bieleski, R. L (Springer-Verlag, Berlin), pp. 528-562, Elzam, O E. & Epstein, E. (1969). Agrochim. 13, 187-195.

LeRudulier, D., Strom, A. R., Dandekar, A. M., Smith, L. T. & Valentine, R. C. (1984) Science 224, 1064-1068.

Yancey, P., Clark, M., Hand, S., Bowlus, R. & Somero, G. (1982) Science 217, 1214-1222.

Smirnoff, N. & Cumbes, Q. J. (1989). Phytochemistry 28, 1057-1060.

Kishor, P. B. K, Hong, Z., Miao, G-H., Hu, C-A. A. & Verma, D P S. (1995). Plant Physiol. 108, 1387-1394.

Nanjo, T., Kobayashi, M., Yoshiba, Y., Kakubari, Y., Yamaguchi-Shinozaki, K. & Shinozaki, K. (1999) FEBS Lett. 461, 205-210.

Browse, J. A. and Somerville, C. R. (1991) Annu. Rev. Plant Physiol. Plant Mol. Biol. 42, 467-506.

Williams, J. P., V. Imperial, M. U. Khan & J. N. Hodson (2000). Biochem. J. 349, 127-133

Huner, N. P. A., M. Krol, J. P. Williams, E. Maissan, P. S. Low, D. Roberts & J. E. Thompson. (1987). Plant Physiol. 84, 12-18.

Ghassemi, F., Jakeman, A. & Nix, H. (1995) Salinization of land and water resources: Human causes, extent, management and case studies. (University of South Wales Press, Sydney).

Epstein, E. (1983) in Better Crops for Food, Ciba Foundation Symposium, eds Nugent, J. & O'Connor, M. (Pitman, London), pp. 97, 61-82.

Ehret, D. L. & Ho, L. C. (1986) J. Exp. Bot. 37, 1294-1302).

Lee, D R. A (1986) Can J. Bot. 67, 1898-1902.

Davies, W. J., Bacon, M. A., Thompson, D. S., Sobeih, W. & Rodriguez, L. G. (2000) J. Exp. Bot. 51, 1617-1626.

Yeo, A. R., Yeo, M. E., Flowers, S. A. & Flowers, T. J. Teor. Appl. Genet. 79, 377-384.

Cuartero, J. & Fernandez-Muñoz, R. (1999) Sci. Hort. 78, 83-125.

Jefferson, R. A., Kavanagh, T. A. & Bevan, M. W. GUS fusions: beta-glucoronidase as a sensitive and versatile gene fusion marker in higher plants. EMBO J. 6, 3901-3907 (1987).

Thomas, B. R. & Pratt, D. Efficient hybridization between Lycopersicon esculentum and L. peruvianum via embryo callus. Theor. Appl. Genet. 59, 215-219 (1981).

Walker, D J., Leigh, R A. & Miller, A J. Potassium homeostasis in vacuolate plant cells. Proc. Natl. Acad. Sci. USA 93, 10510-10514 (1996).

Leigh, R A. & Wynn Jones, R G. A hypothesis relating critical potassium concentrations for growth and distribution and functions of this ion in the plant cell. *New Phytol.* 97, 1-13. (1984).

Blumwald, E. & Gelli, A. Secondary inorganic ion transport in plant vacuoles. *Adv. Bot. Res.* 25, 401-407 (1997).

Munro, A W., Ritchi, G Y., Lamb, R M., Douglas, R M., & Booth, I R. The cloning and DNA sequence of the gene for the glutathion-regulated potassium-efflux system KefC of *Escherichia coli*. *Mol. Microbiol.* 5, 607-616 (1991).

Ramirez, J., Ramirez, O., Saldana, C., Coria, R., & Pena, Antonio. A *Saccharomyces cerevisiae* mutant lacking a $K^+/H^+$ exchanger. *J. Bacteriol.* 180, 5860-5865 (1998).

Czonka, L. N. & Hanson, A. D. Prokaryotic osmoregulation: genetics and physiology. *Annu Rev. Microbiol.* 45, 569-606 (1991).

Schobert, B. Is there an osmotic regulatory mechanism in algae and higher plants? *J. Theor. Biol.* 68, 17-26 (1977).

LeRudulier, D., Strom, A. R., Dandekar, A. M., Smith, L. T. & Valentine, R. C. Molecular biology of osmoregulation. *Science* 224, 1064-1068.

Rea, P. A. & Sanders, D. Tonoplast energyzation: two $H^+$-pumps, one membrane. *Physiol. Plant.* 71, 131-141 (1987).

Carden, D. E., Diamond, D., and Miller, A. J. (2001) An improved $Na^+$-selective microelectrode for intracellular measurements in plant cells. Journal of Experimental Botany 52: 1353-1359.

Carden, D. E., Walker, D. J., Flowers, T. J., and Miller, A. J. (2003) Single-cell measurements of the contributions of cytosolic Na+ and K+ to salt tolerance. Plant Physiology 131: 676-683

TABLE I

Plant and seed yield of wild-type (WT) plants grown in the presence of 10 mM NaCl and transgenic plants overexpressing AtNHX1 ($X1OE_1$) grown in the presence of 10 mM and 200 mM NaCl. Each value is the Mean ± SD (n = 15).

|  | WT | $X1OE_1$ | |
|---|---|---|---|
|  | (10 mM NaCl) | (10 mM NaCl) | (200 mM NaCl) |
| Height (cm) | 210 ± 15 | 218 ± 13 | 183 ± 17 |
| Fresh Weight (g) | 1,750 ± 103 | 1,790 ± 110 | 1,630 ± 134 |
| Seeds per plant | 470 ± 39 | 481 ± 43 | 463 ± 35 |

TABLE II

Total lipid content of leaves and roots from wild-type (WT) plants grown in the presence of 10 mM NaCl and transgenic plants overexpressing AtNHX1 ($X1OE_1$) grown in the presence of 10 mM and 200 mM NaCl. Each value is the Mean ± SD (n = 5).

| TISSUE | LIPID (nmole/gFW) | WT (10 mM NaCl) | $X1OE_1$ (10 mM NaCl) | $X1OE_1$ (200 mM NaCl) |
|---|---|---|---|---|
| LEAVES | PC | 1,120 ± 538 | 1,343 ± 375 | 1,160 ± 287 |
|  | PE | 670 ± 255 | 814 ± 274 | 590 ± 214 |
|  | SQDG | 403 ± 103 | 532 ± 109 | 591 ± 72 |
|  | PG | 899 ± 70 | 830 ± 181 | 776 ± 158 |
|  | DGDG | 1,640 ± 360 | 1,776 ± 289 | 1,817 ± 329 |
|  | MGDG | 4,411 ± 532 | 4,316 ± 786 | 3,658 ± 749 |
| ROOTS | PC | 844 ± 106 | 688 ± 60 | 826 ± 88 |
|  | PE | 690 ± 110 | 629 ± 60 | 660 ± 56 |
|  | MQDG | 394 ± 92 | 563 ± 83 | 633 ± 50 |

TABLE III

| SEQ ID No | PROTEIN NUMBER (GI) | PROTEIN ACCESSION | PROTEIN DESCRIPTION (SPECIES) | SEQUENCE | | | | | |
|---|---|---|---|---|---|---|---|---|---|
| 2 | NHX1 4324597 | AAD16946 | NHX1 Na+/H+ exchanger *Arabidopsis thaliana* | 1 MLDSLVSKLP | SLSTSDHASV | VALNLFVALL | CACIVLGHLL | EENRWMNESI | TALLIGLGTG |
| | | | | 61 VTILLISKGK | SSHLLVFSED | LFFIYLLPPI | IFNAGFQVKK | KQFFRNFVTI | MLFGAVGTII |
| | | | | 121 SCTIISLGVT | QFFKKLDIGT | FDLGDYLAIG | AIFAATDSVC | TLQVLNQDET | PLLYSLVFGE |
| | | | | 181 GVVNDATSVV | VFNAIQSFDL | THLNHEAAFH | LLGNPLYLFL | LSTLLGAATG | LISAYVIKKL |
| | | | | 241 YFGRHSTDRE | VALMMLMAYL | SYMLAELFDL | SGILTVFFCG | IVMSHYTWHN | VTESSRITTK |
| | | | | 301 HTFATLSFLA | ETFIFLYVGM | DALDIDKWRS | VSDTPGTSIA | VSSILMGLVM | VGRAAFVFPL |
| | | | | 361 SFLSNLAKKN | QSEKINFNMQ | VVIWWSGLMR | GAVSMALAYN | KFTRAGHTDV | RGNAIMITST |
| | | | | 421 ITVCLFSTVV | FGMLTKPLIS | YLLPHQNATT | SMLSDDNTPK | SIHIPLLDQD | SFIEPSGNHN |
| | | | | 481 VPRPDSIRGF | LTRPTRTVHY | YWRQFDDSFM | RPVFGGRGFV | PFVPGSPTER | NPPDLSKA |
| 3 | 10716129 | BAB16380 | Na+/H+ exchanger *Ipomoea nil* | 1 MAFGLSSLLQ | NSDLFTSDHA | SVVSMNLFVA | LLCACIVLGH | LLEENRWVNE | SITALIIGLC |
| | | | | 61 TGVVILLLSG | GKSSHLLVFS | EDLFFIYLLP | PIIFNAGFQV | KKKQFFVNFM | TIMLFGAIGT |
| | | | | 121 LISCSIISFG | AVKIFKHLDI | DFLDFGDYLA | IGAIFAATDS | VCTLQVLSQD | ETPLLYSLVF |
| | | | | 181 GEGVVNDATS | VVLFNAIQSF | DMTSFDPKIG | LHFIGNFLYL | FLSSTFLGVG | IGLLCAYIIK |
| | | | | 241 KLYFGRHSTD | REVALMMLMS | YLSYIMAELF | YLSGILTVFF | CGIVMSHYTW | HNVTESSRVT |
| | | | | 301 TRHSFATLSF | VAETFIFLYV | GMDALDIEKW | KFVKNSQGLS | VAVSSILVGL | ILVGRAAFVF |
| | | | | 361 PLSFLSNLAK | KNSSDKISFR | QQIIWWAGL | MRGAVSIALA | YNKFTTSGHT | SLHENAIMIT |
| | | | | 421 STVTVVLFST | VVFGLMTKPL | INLLLPPHKQ | MPSGHSSMTT | SEPSSPKHFT | VPLLDNQPDS |
| | | | | 481 ESDMITGPEV | ARPTALRMLL | RTPTHTVHRY | WRKFDDSFMR | PVFGGRGFVP | FVAGSPVEQS |
| | | | | 541 PR | | | | | |
| 4 | 14039961 | AAK53432 | Na+/H+ Antiporter *Suaeda maritima* | 1 MLSQLSSFFA | SKMDMVSTSD | HASVVSMNLF | VALLRGCIVI | GHLLEENRWM | NESITALLIG |
| | | | | 61 LSTGIIILLI | SGGKSSHLLV | FSEDLFFIYL | LPPIIFNAGF | QVKKKQFFRN | FITIILFGAV |
| | | | | 121 GTLVSFIIIS | LGSIAIFQKM | DIGSLELGDL | LAIGAIFAAT | DSVCTLQVLN | QDETPLLYSL |
| | | | | 181 VFGEGVVNDA | TSVVLFNAIQ | NFDLTHIDHR | IAFQFGGNFL | YLFFASTLLG | AVTGLLSAYV |

TABLE III-continued

| SEQ ID NO | PROTEIN ID NUMBER (GI) | PROTEIN ACCESSION | PROTEIN DESCRIPTION (SPECIES) | SEQUENCE |
|---|---|---|---|---|
| | | | subsp. *salsa* | 241 IKKLYFGRHS TDREVALMML MAYLSYMLAE LFYLSGILTV FFCGIVMSHY TWHNVTESSR<br>301 VTTKHAFATL SFVAEIFIFL YVGMDALDIE KWRFVSDSPG TSVAVSSILL GLHMVGRAAF<br>361 VFPFAFLMNL SKKSNSEKVT FNQQIVIWWA GLMKSAVSVA LAYNQFSRSG HTQLRGNAIM<br>421 ITSTITVVLF STMVFGLLTK PLILFMLPQP KHFTSASTVS DLGSPKSFSL PLLEDRQDSE<br>481 ADLGNDDEEA YPRGTIARPT SLRMLLNAPT HTVHHYWRRF DDYFMRPVFG GRGFVPFVPG<br>541 SPTEQSITNF VTENIS |
| 5 | 14211574 | BAB56105 | Na+/H+ Antiporter *Petunia x hybrida* | 1 MAFDFGTLLG NVDRLSTSDH QSVVSINLFV ALICACIVIG HLLEENRWMN ESITALVIGS<br>61 CTGIVILLIS GGKNSHILVF SEDLFFIYLL PPIIFNAGFQ VKKKSFFRNF STIMLFGALG<br>121 TLISPFIIISL GAIGIFKKMN IGSLEIGDYL AIGAIFSATD SVCTLQVLNQ DETPLLYSLV<br>181 FGEGVVNDAT SVVLFNAIQN FDLSHIDTGK AMELVGNFLY LFASSTALGV AAGLLSAYII<br>241 KKLYFGRHST DREVAIMILM AYLSAILTVF FYLSAILTVF FSGIVMSHYT WHNVTESSRV<br>301 TTKHTFATLS FIAEIFIFLY VGMDALDIEK WKFVSDSPGI SVQVSSILLG LVLVGRAAFV<br>361 FPLSFLSNLT KKTPEAKISF NQQVTIWWAG LMRGAVSMAL AYNQFTRGGH TQLRANAIMI<br>421 TSTITVVLFS TVVFGLMTKP LIRILLPSHK HLSRMISSEP TTPKSFIVPL LDSTQDSEAD<br>481 LERHVPRPHS LRMLLSTPSH TVHYYWRKFD NAFMRPVFGG RGFVPFAPGS PTDPVGGNLQ |
| 6 | 14211578 | BAB56107 | Na+/H+ Antiporter *Torenia hybrida* | 1 MGFESVIKLA ASETDNLWSS GHGSVVAITL FVTLLCTCIV IGHLLEENRW MNESIIALII<br>61 GLATGVIILL ISGGKSSHLL VFSEDLFFIY ALPPIIFNAG FQVKKKSFFR NFATIMMFGA<br>121 VGTLISFIII SLGTIAFFPK MNMRLGVGDY LAIGAIFAAT DSVCTLQVLS QDETPLLYSL<br>181 VFGEGVVNDA TSVVLFNAVQ NFDLPHMSTA KAFELVGNFF YLFATSTVLG VLTGLLSAYI<br>241 IKKLYFGRHS TDREVAIMIL MAYLSGILTV FFCGIVMSHY TWHNVTENSR<br>301 VTTKHTFATL SFVAEIFIFL YVGMDALDIE KWRFVSGSMT TSAAVSATLL GLVLLSRAAF<br>361 VFPLSFLSNL AKKSPLEKIS LRQQIIIWWA GLMRGAVSMA LAYKQFTREG LTVERENAIF<br>421 ITSTITIVLF STVVFGLMTK PLINLLIPSP KLNRSVSSEP LTPNSITIPL LGESQDSVAE<br>481 LFSIRGQTSQ GGEPVARPSS LRMLLTKPTH TVHYYWRKFD NAFMRPVFGG RGFVPYVPGS<br>541 PTERSVRNWE EETKQ |
| 7 | 14488270 | BAB60901 | Na+/H+ exchanger *Ipomoea tricolor* | 1 MAFGLSSLLQ NSELFTSDHA SVVSMNLFVA LLCACIVLGH LLEENRWVNE SITALIIGLC<br>61 TGVVILLLSR GKSSHLLVFS EDLFFIYLLP PIIFNAGFQV KKKQFFVNFM TIMLFGAIGT<br>121 LISCSIISFG AVKIFKHLDI DFLDFGDYLA IGAIFAATDS VCTLQVLSQD ETPLLYSLVF<br>181 GEGVVNDATS VVLFNAIQSF DMTSFDPKIG LHFIGNFLYL FLSSTFLGVG IGLLCAYIIK<br>241 KLYFGRHSTD REVAMMLMS YLSGILTVF CGIVMSHYTW HNVTESSRVT<br>301 TRHSFATLSF VAETFIFLYV GMDALDIEKW KFVKNSQGLS VAVSSILVGL ILVGRAAFVF<br>361 PLSFLSNLAK KNSSDKISPR QQIIIWWAGL MRGAVSIALA YNKFTTSGHT SLHENAIMIT<br>421 STVTVVLFST VVFGLMTKPL INLLLPHKQ IASGHSSMTT SEPSSPKHFA VPLLDNQHDS<br>481 ESDMITGPEV ARPTALRMLL RTPTHTVHRY WRKFDDSFMR PVFGGRGFVP FVAGSPAEQS<br>541 PR |
| 8 | 4585981 | AAD25617 | similar to Na+/H+- exchanging proteins *Arabidopsis thaliana* | 1 MISPVEHDPQ GQVKQQQAAG VGILLQIMML VLSFVLGHVL RRHRFHYLPE ASGSLLIGLI<br>61 VGILANISDT ETSIRFCPPP SIPEFSLLSF PRSLVCSFYS VSGRGLISTK SSSSCFCCLP<br>121 SYYILCFNIC ISSFKFAAAM LCIMDVIFLD IIHLFEPSQV SVFNLNHSFL TLEPLLPLLS<br>181 SELLSLQLLL VVCYLGGSMY LMYKLPFVEC LMFGALISAT DPVTVLSIFQ VLLLFLLLSV<br>241 STGYKYSHDV GTDVNLYALV FGESVLNDAV SFYYLLRYWA LPFKTMSLVN RQSSSGEHFF<br>301 MVVIRFFETF AGSMSAGLAI SFLNSFYTVV FTLLILSEHI VNVMSLFSLF STSIHACRRC<br>361 WSLRHCFYTL HRNCNRRVMK RYTFSNLSEA SQSFVSSFFH LISSLAETFT FIYMGFDIAM<br>421 EQHSWSHVGA VNVFGCAYLV NLFRQENQKI PMKHQKALWY SGLRGAMAFA LALQSLHDLP<br>481 EGHGQIIFTA TTTIVVVTVT FVLLIGGSTG KMLEALEVVG DDLDDSMSEV NSRRSTLISL<br>541 NIGASSDEDT SSSGSRFKMK LKEFHKTGDG DGDGE |
| 9 | 8515714 | AAF76139 | putative Na+/H+ antiporter SOS1 *Arabidopsis thaliana* | 1 MTTVIDATMA YRFLEEATDS SSSSSSSKLE SSPVDAVLFV GMSLVLGIAS RHLLRGTRVP<br>61 YTVALLVIGI ALGSLEYGAK HNLGKIGHGI RIWNEIDPEL LLAVFLPALL FESSFSMEVH<br>121 QIKRCLGQMV LLAVPGVLIS TACLGSLVKV TFPYEWDWKT SLLLGGLLSA TDPVAVALL<br>181 KELGASKKLS TIIEGESLMN DGTAIVVFQL FLKMAMGQNS DWSSIIKFLL KVALGAVGIG<br>241 LAFGIASVIW LKFIFNDTVI EITLTIAVSY FAYYTAQEWA GASGVLTVMT LGMFYAAFAR<br>301 TAFKGDSQKS LHHFWEMVAY IANTLIFILS GVVIAEGILD SDKIAYQGNS WRFLFLLYVY<br>361 IQLSRVVVVG VLYPLLCRFG YGLDWKESII LVWSGLRGAV ALALSLSVKQ SSGNSHISKE<br>421 TGTLFLFFTG GIVFLTLIVN GSTTQFVLRL LRMDILPAPK KRILEYTKYE MLNKALRAFQ<br>481 DLGDDEELGP ADWPTVESYI SSLKGSEGEL VHHPHNGSKI GSLDPKSLKD IRMRFLNGVQ<br>541 ATYWEMLDEG RISEVTANIL MQSVDEALDQ VSTTLCDWRG LKPHVNFPNY YNFLHSKVVP<br>601 RKLVTYFAVE RLESACYISA AFLRAHTIAR QQLYDFLGES NIGSIVINES EKEGEEAAKF<br>661 LEKVRSSFPQ VLRVVKTKQV TYSVLNHLLG YIENLEKVGL LEEKEIAHLH DAVQTGLKKL<br>721 LRNPPIVKLP KLSDMITSHP LSVALPPAFC EPLHKSKKEP MKLRGVTLYK EGSKPTGVWL<br>781 IFDGIVKWKS KILSNNHSLH PTFSHGSTLG LYEVLTGKPY LCDLITDSMV LCFFIDSEKI<br>841 LSLQSDSTID DFLWQESALV LLKLLRPQIF ESVAMQELRA LVSTESSKLT TYVTGESIEI<br>901 DCNSIGLLLE GFVKPVGIKE ELISSPAALS PSNGNQSFHN SSEASGIMRV SFSQQATQYI<br>961 VETRARAIIF NIGAFGADRT LHRRPSSLTP PRSSSSDQLQ RSFRKEHRGL MSWPENIYAK<br>1021 QQQEINKTTL SLSERAMQLS IFGSMVNVYR RSVSFGGIYN NKLQDNLLYK KLPLNPAQGL<br>1081 VSAKSESSIV TKKQLETRKN ACQLPLKGES STRQNTMVES SDEEDEDEGI VVRIDSPSKI<br>1141 VFRNDL |
| 10 | 9857314 | BAB11940 | Na/H antiporter Nhx1 *Atriplex* | 1 MWSQLSSLLS GKMDALTTSD HASVVSMNLF VALLCGCIVI GMLLEENRWM NESITALLIG<br>61 LATGVVILLI SGGKSSHLLV FSEDLFFIYL LPPIIFNAGF QVKKKQFFRN FITIVLFGAV<br>121 GTLVSFTIIS LGALSIFKKL DIGTLELADY LAIGAIFAAT DSVCTLQVLN QDETPLLYSL<br>181 VFGEGVVNDA TSVVLFNAIQ SFDLTRIDHR IALQFMGNFL YLFIASTILG AFTGLLSAYI |

TABLE III-continued

| SEQ ID NUMBER No (GI) | PROTEIN ACCESSION | PROTEIN DESCRIPTION (SPECIES) | SEQUENCE | |
|---|---|---|---|---|
| | | *gmelini* | 241 IKKLYFGRHS TDREVALMML MAYLSYMLAE LFYLSGILTV FFCGIVMSHY TWHNVTESSR | |
| | | | 301 VTTKHAFATL SFVAEVFLFL YVGMDALDIE KWRFVSDSPG ISVAVSSILL GLVMVGRAAF | |
| | | | 361 VFPLSWLMNF AKKSQSEKVT FNQQIVIWWA GLMRGAVSMA LAYNQFTRSG HTQLRGNAIM | |
| | | | 421 ITSTISVVLF STMVPGLLTK PLIMFLLPQP KHFTSCSTVS DVGSPKSYSL PLLEGNQDYE | |
| | | | 481 VDVGNGNHED TTEPRTIVRP SSLRMLLNAP THTVHHYWRK FDDSFMRPVF GGRGFVPFVP | |
| | | | 541 GSPTEQSTNN LVDRT | |
| 11 6323167 | NP_013239 | NHA1 Putative Na+/H+ antiporter; Nha1p *Saccharomyces cerevisiae* | 1 MAIWEQLEVS KAHVAYACVG VFSSIFSLVS LYVKEKLYIG ESTVAGIFGL IVGPVCLNWF | |
| | | | 61 NPLKWGNSDS ITLEITRIVL CLQIFAVAVE LPRKYMLKHW VSVTMLLLPV MTAGWLIIGL | |
| | | | 121 FVWILIPGLN FSASLLISAC ITATDPILAQ SVVSGKFAQR VPGHLRNLLS AESGCNDGMA | |
| | | | 181 FPPFLFLSMNL ILHPGNGREI VKDWICVTIL YECLFGCLLG CFIGYVGRIT IRFAEKKNII | |
| | | | 241 DRESFLAFYV VLAFMCAGFG SILGVDDLLV SFAAGATFAW DGWFSQKTQE SNVSTVIDLL | |
| | | | 301 LNYAYFIYFG AIIPWSQFNN GEIGTNVWRL IILSIVVIFL RRIPAVMILR PLIPDIKSWR | |
| | | | 361 EALFVGHFGP IGVGAIFAAI LARGELESTF SDEPTPLNVV PSKEESKHWQ LIACIWPITC | |
| | | | 421 FFIVTSIIVH GSSVAIITLG RHLNTITLTK TFTTHTTNGD NGKSSWMQRL PSLDKAGRSF | |
| | | | 481 SLHRMDTQMT LSGDEGEAEE GGGRKGLAGG EDEEGLNNDQ IGSVATSGIP ARPAGGMPRR | |
| | | | 541 RKLSRKEKRL NRRQKLRNKG REIFSSRSKN EMYDDDELND LGRERLQKEK EARAATFALS | |
| | | | 601 TAVNTQRNEE IGMGGDEEED EYTPEKEYSD NYNNTPSFES SERSSSLRGR TYVPRNRYDG | |
| | | | 661 EETESEIESE DEMENESERS MASSEERRIR KMKEEEMKPG TAYLDGNRMI IENKQGEILN | |
| | | | 721 QVDIEDRNEA RDDEVSVDST AHSSLTTTMT NLSSSSGGRL KRILTPTSLG KIHSLVDKGK | |
| | | | 781 DKNKNSKYHA FKIDNLLIIE NEDGDVIKRY KINPHKSDDD KSKNRPRNDS VVSRALTAVG | |
| | | | 841 LKSKANSGVP PPVDEEKAIE GPSRKGPGML KKRTLTPAPP RGVQDSLDLE DEPSSEEDLG | |
| | | | 901 DSYNMDDSED YDDNAYESET EFERQRRLNA LGEMTAPADQ DDEELPPLPV EAQTGNDGPG | |
| | | | 961 TAEGKKKQKS AAVKSALSKT LGLNK | |
| 12 6320663 | NP_010744 | NHX1 Required for intracellular sequestration of Na+; Nhx1p *Saccharomyces cerevisiae* | 1 MLSKVLLNIA FKVLLTTAKR AVDPDDDDEL LPSPDLPGSD PIAGDPDVD LNPVTEEMFS | |
| | | | 61 SWALFIMLLL LISALWSSYY LTQKRIRAVH ETVLSIFYGM VIGLIIRMSP GHYIQDTVTF | |
| | | | 121 NSSYFFNVLL PPIILNSGYE LNQVNFFNNM LSILIFAIPG TPISAVVIGI ILYIWTFLGL | |
| | | | 181 ESIDISFADA MSVGATLSAT DPVTILSIFN AYKVDPKLYT IIFGESLLND AISIVMFETC | |
| | | | 241 QKFHGQPATF SSVFEGAGLF LMTFSVSLLI GVLIGILVAL LLKHTHIRRY PQIESCLILL | |
| | | | 301 IAYESYFFSN GCHMSGIVSL LFCGITLKHY AYYNMSRRSQ ITIKYIFQLL ARLSENFIFI | |
| | | | 361 YLGLELFTEV ELVYKPLLII VAAISICVAR WCAVFPLSQF VNWIYRVKTI RSMSGITGEN | |
| | | | 421 ISVPDEIPYN YQMMTFWAGL RGAVGVALAL GIQGEYKFTL LATVLVVVVL TVIIFGGTTA | |
| | | | 481 GMLEVLNIKT GCISEEDTSD DEFDIEAPRA INLLNGSSIQ TDLGPYSDNN SPDISIDQFA | |
| | | | 541 VSSNKNLPNN ISTTGGNTFG GLNETENTSP NPARSSMDKR NLRDKLGTIF NSDSQWFQNF | |
| | | | 601 DEQVLKPVFL DNVSPSLQDS ATQSPADFSS QNH | |
| 13 15229877 | NP_187154 | NHX2 NHX2 Na+/H+ exchanger *Arabidopsis thaliana* | 1 MTMFASLTSK MLSVSTSDHA SVVSLNLFVA LLCACIVIGH LLEENRWMNE SITALLIGLG | |
| | | | 61 TGVVILLISR GKNSHLLVFS EDLFFIYLLP PIIFNAGFQV KKKQFFRNFV TIMAFGAIGT | |
| | | | 121 VVSCTIISLG AIQFFKKLDI GTFDLGDPLA IGAIFAATDS VCTLQVLNQD ETPLLYSLVF | |
| | | | 181 GEGVVNDATS VVLFNAIQSF DLTHLNHEAA FQFLGNFFYL FLLSTGLGVA TGLISAYVIK | |
| | | | 241 KLYFGRHSTD REVALMMLMA YLSYMLAELF ALSGILTVFF CGIVMSHYTW HNVTESSRIT | |
| | | | 301 TKHAFATLSF LAETFIFLYV GMDALDIEKW RFVSDSPGTS VAVSSILMGL VHLGRAAFVF | |
| | | | 361 PLSFLSNLAK KHQSEKISIK QQVVIWWAGL MRGAVSMALA YNKFTRSGHT ELRGNAIMIT | |
| | | | 421 STITVCLFST MVFGMLTKPL IRYLMPHQKA TTSTTSMLSD DSTPKSIHIP LLDGEQLDSF | |
| | | | 481 ELPGSHQDVP RPNSLRGFLM RPTRTVHYYW RQFDDAFMRP VFGGRGFVPF VPGSPTERSS | |
| | | | 541 HDLSKP | |
| 14 15240159 | NP_200358 | NHX3 Na+/H+ exchanger *Arabidopsis thaliana* | 1 MSIGLTEFVT NKLAAEHPQV IPISVFIAIL CLCLVIGHLL EENRWVNESI TAILVGAASG | |
| | | | 61 TVILLISKGK SSHILVFDEE LFFIYLLPPI IFNAGFQVKK KKFFHNFLTI MSFGVIGVFI | |
| | | | 121 STVIISFGTW WLFPKLGFKG LSARDYLAIG TIFSSTDTVC TLQILHQDET PLLYSLVFGE | |
| | | | 181 GVVNDATSVV LFNAVQKIQF ESLTGWTALQ VFGNFLYLFS TSTLLGIGVG LITSFVLKTL | |
| | | | 241 YFGRHSTTRE LAIMVLMAYL SYMLAELFSL SGILTVFFCG VLMSHYASYN VTESSRITSR | |
| | | | 301 HVFAMLSFIA ETFIFLYVGT DALDFTKWKT SSLSFGGTLG VSGVITALVL LGRAAFVPFL | |
| | | | 361 SVLTNFMNRH TERNESITFK HQVIIWWAGL MRGAVSIALA FKQFTYSGVT LDPVNAAMVT | |
| | | | 421 NTTIVVLFTT LVFGFLTKPL VNYLLPQDAS HNTGNRGKRT EPGSPKEDAT LPLLSFDESA | |
| | | | 481 STNFNRAKDS ISLLMEQPVY TIHRYWRKFD DTYMRPIFGG PRRENQPEC | |
| 15 15230706 | NP_187288 | NHX4 Na+/H+ exchanger *Arabidopsis thaliana* | 1 MVIGLSTMLE KTEALFASDH ASVVSMNLFV ALLCACIVLG HLLEETRWMN ESITALIIGS | |
| | | | 61 CTGIVILLIS GGKSSRILVF SEDLFFIYLL PPIIPNAGFQ VKKKQFFRNF MTIMLFGAIG | |
| | | | 121 TLISFVIISF GAKHLFEKMN IGDLTIADYL AIGAIFSATD SVCTLQVLNQ DETPLLYSLV | |
| | | | 181 FGEGVVNDAT SVVLFNAIQR FDLTNINSAI ALEFAGNFFY LFILSTALGV AAGLLSAFVI | |
| | | | 241 KKLYIGRHST DREVALMMLL AYLSYMLAEL FHLSSILTVF FCGIVMSHYT WHNVTDKSKV | |
| | | | 301 TTKHTFAAMS FLAEIFIFLY VGMDALDIEK WDVVRNSPGQ SIGVSSILLG LILLGRAAFV | |
| | | | 361 FPLSFLSNLT KSSPDEKIDL KKQVTIWWAG LMRGAVSMAL AYNQFTTSGH TKVLGNAIMI | |
| | | | 421 TSTITVVLFS TVVFGLLTKP LVKHLQPSSK QSSTTALQIT LRSSFHDPIL HEPLLSTQGQ | |
| | | | 481 SEYDPEQHVS FRMFWKSPSR AIHHYWRKFD NAVMRRIFGG RGVSPVVPGS PIENSVPQWS | |
| | | | 541 EEVENKEQNG EP | |

TABLE III-continued

| SEQ ID No | PROTEIN NUMBER (GI) | PROTEIN ACCESSION | PROTEIN DESCRIPTION (SPECIES) | SEQUENCE |
|---|---|---|---|---|
| 16 | 30695721 | NP_175839 | NHX5 Na+/H+ exchanger Arabidopsis thaliana | 1 MEEVMISPVE HDPQGVKQQ QAAGVGILLQ IMMLVLSFVL GHVLRRHRFH YLPEASGLIV<br>61 GILANISDTE TSIRFCPPPS IPEFSLLSFP RSLKPFFSNF GAIVTFAIIG TFVASVVTGG<br>121 LVYLGGSMYL MYKLPFVECL MFGALISATD PVTVLSIFQD VGTDVNLYAL VFGESVLNDA<br>181 VSFYYLLRYW ALPFKFFETF AGSMSAEHLF KYAGLDTENL QNLECCLFVL FPYFSYMLAE<br>241 GVGLSGIVSI LFTGIVMKRY TFSNLSEASQ SFVSSFFHLI SSLAETFTFI YMGFDIAMEQ<br>301 HSWSHVGFIL FSIVSSFTDR QAVNVFGCAY LVNLFRQENQ KIPMKHQKAL WYSGLRGAMA<br>361 FALALQSLHD LPEGHGQIIF TATTTIVVVT VLLIGGSTGK MLEALEVVGD DLDDSMSEGF<br>421 EESDHQYVPP PFSIGASSDE DTSSSGSRFK MKLKEFHKTT TSFTALDKNF LTPFFTTNSG<br>481 DGDGDGE |
| 17 | 22330742 | NP_178079 | NHX6 Na+/H+ exchanger Arabidopsis thaliana | 1 MSSELQISPA IHDPQGQEKQ QAAGVGILL QIMMLVLSFV LGHVLRRHKF YYLPEASASL<br>61 LIGLIVGGLA NISNTETSIR FVELFLISFF RHGSISTMSS SFCFCCLPSY YILKIEYLGG<br>121 VMFLMYRLPF VECLMFGSLI SATDPVTVLS IFQELGSDVN LYALVFGESV LNDADEIVTL<br>181 LIRSFSFLCC FWQMAISLYR TMSLVRSHSS GQNFFMVIVR FLETFVGSMS AAMKYFILMY<br>241 SLLLSVYRTW SAVSSYFFHI SRNKTLLFYT SYVSIYFTLI EIVQFVMKHY TYSNLSANSQ<br>301 RFVSAFFHLI SSLAETFVFI YMGFDIAMEK HSWAANVFGC GYLVNLARPA HRKIPMTHQK<br>361 ALWYSGKILL CVPLSSYCFY SSVINTKICG FCIGLRGAMA FALALQSVHD LPEGHGQTIF<br>421 TATTAIVVLT VLLIGGSTGT MLEALEVVGD SHDTSLGDGF EVVNSRYMTS YDDEDTPPGS<br>481 GFRTKLREFH KSAASFTELD RNYLTPFFTS NNGDYDDEGN MEQHHGNNII L |
| 18 | 22325422 | NP_178307 | NHX7 Na+/H+ exchanger Arabidopsis thaliana | 1 MTSIIGAALP YKSPEKAIAS SSYSAENDSS PVDAVIFAGT SLVLGTACRY LFNGTRVPYT<br>61 VVLLVIGIFL GSLEYGTKHN LGKLGHGIRI WNGINPDLLL AVFLPVLLFE SSFSMDVHQI<br>121 KRCMGQMVLL AGPGVLISTF CLGALIKLTF PYNWDWKTSL LLGGLLGATD PVAVVALLKE<br>181 LGASKKMTTL IDGESLMNDG VSVVVFQLFF KMVMGHNSDW GSIIKFLVQN SFGAVGIGLA<br>241 FGIASVFWLK FIFNDTVAQI TVTLSASYFA YYTAQEWAGV SGILTVMILG MFFAAFARTA<br>301 FKGDSHQSLH HFWYFTTQEM AAYIANTLVF MLSGVIIAES VLSGQTISYK AIKWKFISQF<br>361 RYGNKAVLQF LFLTGGIVFL TLVVNGSTTQ LLLHLLRMDT LTATKKRILE YTKFEMMKTA<br>421 LKAFENLGDD EELGSADWPT VIRHISSLKD LEGRQVNPHD GYEAGSLDPT NIMDIRVQAA<br>481 YWEMLDDGRI TQCTANVLMQ SVDEALDLVS TSSLSDWRGL EPRVHFPNYY KFLQSKIIPH<br>541 KLVTHLIVER LESACYISSA FLRAHRIARQ QLHIFLGNSN IASTVINESE VEGEEAKQFL<br>601 EDVRDSFPQV LSVLKTRQVT HYVLNHLNGY IKNLEKVGLL EGKEVSHLHD VVQSDLKKLL<br>661 RHPPSLKLPN VDDLITSNPL LKDRSSFRSL AIGETDA |
| 19 | 15223849 | NP_172918 | NHX8 Na+/H+ exchanger Arabidopsis thaliana | 1 MTSIIGAALP YKSPEKAIAS SSYSAENDSS PVDAVIFAGT SLVLGTACRY LFNGTRVPYT<br>61 VVLLVIGIFL GSLEYGTKHN LGKLGHGIRI WNGINPDLLL AVFLPVLLFE SSFSMDVHQI<br>121 KRCMGQMVLL AGPGVLISTF CLGALIKLTF PYNWDWKTSL LLGGLLGATD PVAVVALLKE<br>181 LGASKKMTTL IDGESLMNDG VSVVVFQLFF KMVMGHNSDW GSIIKFLVQN SFGAVGIGLA<br>241 FGIASVFWLK FIFNDTVAQI TVTLSASYFA YYTAQEWAGV SGILTVMILG MFFAAFARTA<br>301 FKGDSHQSLH HFWYFTTQEM AAYIANTLVF MLSGVIIAES VLSGQTISYK AIKWKFISQF<br>361 RYGNKAVLQF LFLTGGIVFL TLVVNGSTTQ LLLHLLRMDT LTATKKRILE YTKFEMMKTA<br>421 LKAFENLGDD EELGSADWPT VIRHISSLKD LEGRQVNPHD GYEAGSLDPT NIMDIRVQAA<br>481 YWEMLDDGRI TQCTANVLMQ SVDEALDLVS TSSLSDWRGL EPRVHFPNYY KFLQSKIIPH<br>541 KLVTHLIVER LESACYISSA FLRAHRIARQ QLHIFLGNSN IASTVINESE VEGEEAKQFL<br>601 EDVRDSFPQV LSVLKTRQVT HYVLNHLNGY IKNLEKVGLL EGKEVSHLHD VVQSDLKKLL<br>661 RHPPSLKLPN VDDLITSNPL LKDRSSFRSL AIGETDA |
| 20 | 15982204 | CAC84522 | Na+/H+ antiporter, isoform 1 Lycopersicon esculentum | 1 MGLDAVARLG VSILSDGDQV SVDSITLFVA LLCGCIVIGH LLEESRWIND SITTLVIGLS<br>61 TGGIILLTTK GKSSHLLEFD EQLFFIYVLP PIIFNAGFQV KKKQFFRNFV TIMLFGAVGT<br>121 LISFSIISFG AKELLGKLDI GFLELRDYLA IGAIFSATDS VCTLQALNQD ETPRLYSLVF<br>181 GEGVVNDATS VVLFNAIQKL DLSHINSRAA LVFTGNFLYL FLASTFLGVL IGLLSAYLIK<br>241 KIYLGRHSTD REVALMILMA YLSYVMAELF DLSGILTVFI CGIVMSHYTW HNVTFNSKVT<br>301 TRHAFATLSF IAEIFIFLYV GMDALDIEKW RFVKDSPGKS VGVSAALLGL VLVGRACFVF<br>361 PLSLFSNCLK RSEHDKFGLK LQVTIWWAGL MRGSVSMALA YNQFTRFGHT QQPGNAVMIT<br>421 STITIVLFST VVFGLITKPL VRFLLPSSQG FNNLISSEQS FARPLLTNEQ ELELEMGNVD<br>481 PVRPSGLSIL LKEPSYTIHN HWRRFDDAFM RPLFGGRGFV PDAPELSKGG CDQY |
| 21 | 15982206 | CAC83608 | Na+/H+ antiporter, isoform 2 Lycopersicon esculentum | 1 MEDHLQISPA GAKAIPGKEQ QAAGYGILLQ IMMLVLSFVI GHVLRRRHFY YIPEASASLL<br>61 IGLIVGGLAN VSDTETSIRA WFNFHEEFFF LFLLPPIIFQ SGFSLSPKPF FSNFGAIITF<br>121 AILGTFIASF VTGILVYLGG VTYLMYRLPF VECLMFGALI SATDPVTVLS IFQELGTDVN<br>181 LYALVFGESV LNDAMAISLY RTMSLVRSHM STDQNYFMIT IRFVETFMGS LSAGVGVGFV<br>241 SALLFKYAGL DIDNLQNLES CLFVLFPYFS YMLAEGLGLS GIVSILFTGV VMKRYTPNL<br>301 SESSQRFVSA FFHLISSLAE TFVFIYMGFD IAMEKHSWSH VGFIFFSILF IVIARAANVF<br>361 GCAYLVNLVR PPHQKIPAKH QKALWYSGLR GAMAFALALQ PVHDLPEGHG QAIFTATTAI<br>421 VVLTVLIIGG SAGTMLEALE VVGDGQSGSM DETFGNNGY IAPSYRDESY DGEPSSGNRF<br>481 RMKLKEFHKS TTSFSALDKN YLTPFFTTQG GDEDEDEPIM HSSRRAGYDG H |
| 22 | 5731737 | BAA83337 | OsNHX1 Oryza sativa | 1 MGMEVAAARL GALYTTSDYA SVVSINLFVA LLCACIVLGH LLEENRWVNE SITALIIGLC<br>61 TGVVILLMTK GKSSHLLVFS EDLFFIYLLP PIIFNAGFQV KKKQFFRNFM TITLFGAVGT<br>121 MISFFTISIA AIAIFSRMNI GTLDVGDFLA IGAIFSATDS VCTLQVLNQD ETPFLYSLVF |

TABLE III-continued

| SEQ ID NUMBER No (GI) | PROTEIN ACCESSION | PROTEIN DESCRIPTION (SPECIES) | SEQUENCE | |
|---|---|---|---|---|
| | | (japonica cultivar-group) | 181 | GEGVVNDATS IVLFNALQNF DLVHIDAAVV LKFLGNFFYL FLSSTFLGVF AGLLSAYIIK |
| | | | 241 | KLYIGRHSTD REVALMMLMA YLSYMLAELL DLSGILTVFF CGIVMSHYTW HNVTESSRVT |
| | | | 301 | TKHAFATLSF IAETFLFLYV GMDALDIEKW EFASDRPGKS IGISSILLGL VLIGRAAFVF |
| | | | 361 | PLSFLSNLTK KAPNEKITWR QQVVIWWAGL MRGAVSIALA YNKFTRSGHT QLHGNAIMIT |
| | | | 421 | STITVVLFST MVFGMMTKPL IRLLLPASGH PVTSEPSSPK SLHSPLLTSM QGSDLESTTN |
| | | | 481 | IVRPSSLRML LTKPTHTVHY YWRKFDDALM RPMFGGRGFV PFSPGSPTEQ SHGGR |
| 23 14211576 | BAB56106 | Na+/H+ antiporter, Nierembergia caerulea | 1 | MAFDFGTLLG KMNNLTTSDH QSVVSVNLFV ALICACIVIG HLLEENRWMN ESITALVIGS |
| | | | 61 | CTGVIILLIS GGKNSHILVF SEDLFFIYLL PPIIFNAGFQ VKKKSFFRNF STIMLFGAVG |
| | | | 121 | TLISPFIIISA GAIGIFKKMD IGHLEIGDYL AIGAIFAATD SVCTLQVLNQ EETPLLYSLV |
| | | | 181 | FGEGVVNDAT SVVLFNAVQN FDLSHISTGK ALQLIGNFLY LFASSTFLGV AVGLLSAFII |
| | | | 241 | KKLYFGRHST DREVAIMILM AYLSGILTVF FCGIVMSHYT WHNVTESSRV |
| | | | 301 | TTKHTFATLS FIAEIFIFLY VGMDALDIEK WKFVSDSPGT SIKVSSILLG LVLVGRGAFV |
| | | | 361 | FPLSFLSNLT KKNPEDKISF NQQVTIWWAG LMRGAVSMAL AYNQFTRGGH TQLRANAIMI |
| | | | 421 | TSTITVVLFS TVVFGLMTKP LILLLLPSQK HLIRMISSEP MTPKSFIVPL LDSTQDSEAD |
| | | | 481 | LGRHVPRPHS LRMLLSTPSH TVHYYWRKFD NAFMRPVFGG RGFVPFVPGS PTEPVEPTEP |
| | | | 541 | RPAESRPTEP TDE |
| 24 15812035 | AAK27314 | Na+/H+ exchanger Citrus x paradisi | 1 | MDQAISSVVR KLQMVNTSDH NSVVSINIFV ALPCASIVIG HLLEESRWMN ESITALLIGV |
| | | | 61 | CAGVIILLTT GGKSSHLFVS SEDLFFIYLL PPIIFNAGFQ VKKKQFFRNF ITIMLFGAIG |
| | | | 121 | TLVSCTIISL GVIQFFKKLD IGTLDIGDYL AIGAIFAATD SVCTLQVLNQ DDTPLLYSLV |
| | | | 181 | FGEGVVNDAT SVVLFNAIQS FDLTHINTRS AFQFIGNFLY LFFTSTLLGV IGGLLSAYVI |
| | | | 241 | KKLYFGRHST DREVAIMVLM AYLSYMLAEL FYLSGILTVF FCGIVMSHYT WHNVTESSRV |
| | | | 301 | TTKHTFATLS FVAEIFTFLY VGMDALDIEK WRFVKGSPGT SVAASAMLMG LIMAGRAAFV |
| | | | 361 | FPLSFLTNLA KKSPTEKISI KQQVIWWAG LMRGAVSMAL AYNQFTRSGH TQLRENAIMI |
| | | | 421 | TSTITVVLFS TVVFGLMTEP LIRLLLPHPK HTTNHILSDP STPKSLSQPL LEEGQQDSYA |
| | | | 481 | DLVGPTVPRP GSLRALLTTP THTVHYYWRK FDDAFMRPVF GGRGFAPFVP GSPTERSVRG |
| | | | 541 | GQ |
| 25 15027833 | AAK76737 | Na+/H+ antiporter Triticum aestivum | 1 | MGLDLGALAL KYTGLAVSDH DSIVAINIFI ALLCGCIVFG HLLEGNRWVN ESTTALVLGL |
| | | | 61 | ITGVILICT KGVNSRILIF SEDIFFIYLL PPIIFNAGFQ VKKKQFFRNF ATIILFGAAG |
| | | | 121 | TLISFVIITF GAMGLFSKLD VGPLELGDYL AIGAIFSATD SVCTLQVLNQ DEAPLLYSLV |
| | | | 181 | FGEGVVNDVF VLLQFIGKFV LFFTSTVLGV AAGLLSAYII |
| | | | 241 | KKLCFARHST DREVAIMILM AYLSYMLSML LDLSGILTVF FCGIVMSHYT WHNVTESSRV |
| | | | 301 | TTKHTFATLS FIAEIFLFLY VGMDALDIDK WKLASSSPKK PIALSAVILG LVMVGRAAFV |
| | | | 361 | FPLSFLSNLS KKESHPKISF NQQVIIWWAG LMRGAVSIAL AYNKFTTSGH TAVRVNAVMI |
| | | | 421 | TSTIIVVLFS TMVFGLLTKP LINLLIPPRP GTAADISSQS FLDPLTASLL GSDFDVGQLT |
| | | | 481 | PQTNLQYLLT MPTRSVHRVW RKFDDKFMRP MFGGRGFVPF VPGSPIERSV HGPGLLGTVT |
| | | | 541 | EAEDRS |
| 26 28575021 | AAK76738 | Na+/H+ antiporter Triticum aestivum | 1 | MGYQVVAAQL ARLSGALGTS DHASVVSITL FVALLCACIV LGHLLEENRW LNESITALII |
| | | | 61 | GLCTGVVILM TTKGKSSHVL VFSEDLFFIY LLPPIIFNAG FQVKKKQFFR NFMAITLFGA |
| | | | 121 | VGTMMSFFTI SLAAIAIFSR MNIGTLDVSD FLAIGAIFSA TDSVCTLQVL NQDETPFLYS |
| | | | 181 | LVFGEGVVND ATSVVLFNAL QNFDPNQIDA IVILKFLGNF CYLFVSSTFL GVFTGLLSAY |
| | | | 241 | VIKKLYIGRH STDREVALVM LMAYLSYMLA ELLDLSGILT VFFCGIVMSH YTWHNVTESS |
| | | | 301 | RVTTKHAFAT LSFIAETFLF LYVGMDALDI EKWKFASDSP GKSIGISSIL LGLVLVGRAA |
| | | | 361 | FVFPLSFLSN LTKKTELEKI SWRQQIVIWW AGLMRGAVSI ALAYNKFTRS GHTQLHGNAI |
| | | | 421 | MITSTITVVL FSTMLFGILT KPLIRFLLPA SSNGAASDPA SPKSLHSPLL TSQLGSDLEA |
| | | | 481 | PLPIVRPSSL RNLITKPTHT IHYYWRKFDD ALMRPMFGGR GFVPYSPGSP TDPNVLVE |
| 27 31580736 | AAP55209 | Na+/H+ antiporter Triticum aestivum | 1 | MGLDLGALAL KYTGLAVSDH DSIVAINIFI ALLCGCIVFG HLLGGNRWVN ESTAALVLGL |
| | | | 61 | ITGVILICT KGVNSRILIF SEDIFFIYLL PPIIFNAGFQ VKKKQFFRNF ATIILFGAAG |
| | | | 121 | TLISFVIITF GAMGLFSKLD VGPLELGDYL AIGAIFSATD SVCTLQVLNQ DEAPLLYSLV |
| | | | 181 | FGEGVVNDAT SVVLFNAIQN IDINHDVFV LLQFIGKFV LFFTSTVLGV AAGLLSAYII |
| | | | 241 | KKLCFARHST DREVAIMILM AYLSCMLSML LDLSGILTVF FCGIVMSHYT WHNVTESSRV |
| | | | 301 | TTKHTFATLS FIAEIFLFLY VGMDALDIDK WKLASSSPKK PIALSAVILG LVMVGRAAFV |
| | | | 361 | FPLSFLSNLS KKESHPKISF NQQVIIWWAG LMRGAVSIAL AYNKFTTSGH TAVRVNAVMI |
| | | | 421 | TSTIIVVLFS TMVFGLLTKP LINLLIPPRP GTAADISSQS FLDPLTASLL GSDFDVGQLT |
| | | | 481 | PQTNLQYLLT MPTRSAHRVW RKFDDKFMRP MFGGRGFVPF VPGSPIERSV HGPGLLGTVT |
| | | | 541 | EAEDRS |
| 28 30172039 | AAP20428 | Na+/H+ antiporter NHX1 Zea mays subsp. mays | 1 | MGLGVVAELV RLGVLSSTSD HASVVSINLF VALLCACIVL GHLLEENRWV NESTALIVGL |
| | | | 61 | GTGTVILMIS RGVVIHVLVF SEDLFFFYLL PPIIFNAGFQ VKKKQFFRNF ITITLFGAVG |
| | | | 121 | TLISFTVISL GALGLISRLN IGALELGDYL ALGAIFSATD SVCTLQVLSQ DETPFLYSLV |
| | | | 181 | FGEGVVNDAT SVVVFNALQN FDITHIDAEV VFHLLGNFFY LFLLSTVLGV ATGLISALVI |
| | | | 241 | KKLYFGRHST DREVAIMMLM AYLSYMLAEL FALSGILTVF FCGIVMSHYT WHNVTESSRI |
| | | | 301 | TTKHAFATLS FLAETFLFLY VGMDALDIEK WRSVDTPGK SLAISSILMG LVMVGRAAFV |
| | | | 361 | FPLSFLSNLA KKTEHEKISW KQQVVIWWAG LMRGAVSMAL AYKKKFTRAGH TQVRGNAIMI |
| | | | 421 | TSTIIVVLFS TMVFGLLTKP LINLLIPHRN ATSMLSDDSS PKSLHSPLLT SQLGSDLEEP |
| | | | 481 | TNIPRPSSIR GEFLTMTRTV HRYWRKFDDA FMRPMFGGRG FVPFVPGSPT ERNPPDLSKA |
| 29 30172041 | AAP20429 | Na+/H+ antiporter NHX2 Zea mays | 1 | MGLGVDAETV RLGVLSSTSD HASVVSNNFF VAILLCACIVL GHLLEENRMV NESITALLVG |
| | | | 61 | LGTGTVILMI SRGVSIHVLV FSEDLFFIYL LPPIIFNAGF QVKKKQFFRN FITIILFGAI |
| | | | 121 | GTLISFVIIS LGAMGLFKKL DVGPLELGDY LAIGAIFSAT DSVCTLQVLN QDETPLLYSL |
| | | | 181 | VFGEGVVNDA TSIVVFNALQ NFDITHINAE VVFHLLGNFL YLFLLSTVLG VATGLISALV |

TABLE III-continued

| SEQ ID NO | PROTEIN NUMBER (GI) | PROTEIN ACCESSION | PROTEIN DESCRIPTION (SPECIES) | SEQUENCE |
|---|---|---|---|---|
| | | | subsp. mays | 241 IKKIYFGRHS TDREVALMML MAYLSYMLAE LFALSGILTV FFGCIVMSHY TWHNVTESSR<br>301 ITTKHAFATL SFLAETFIFL YVGMDALDIE KWRSVSDTPG KSIAISSILM GLVMLGRAAF<br>361 VFPLSFLSNL AKKNEHEKIS WKQQVVIWWS GLMRGAVSMA LAYNKFTRAG HTEVRGNEIM<br>421 ITSTITVVLF STVVFGLLTK PLIRLLMPHR HLTMLSDDST PKSLHSPLLT SQLGSSIEEP<br>481 TQIPRPTNIR GEFTTMTRTV HRYWRKFDDK FMRPMFGGRG FVPFVPGSPT ERNPHDLSKP |
| 30 | 32396168 | AAP20430 | Na+/H+ antiporter NHX3 Zea mays subsp. mays | 1 MSIGLTAETV TNKLASAEHP QVVPNSVFIA LLCLCLVIGH LLEENRWVNE SITAILVGAA<br>61 TGTVILLISK GKSSHILVFD EELFFIYLLP PIIFNAGFQV KKKQFFRNFI TIILFGAIGT<br>121 LISFVIISLG AMGLFKKLDV GPLELGDYLA IGAIFSATDS VCTLQVLNQD ETPLLYSLVF<br>181 GEGVVNDATS VVLFNAVQKI DFEHLTGEVA LQVFGNPLYL FSTSTVLGIA TGLITAFVLK<br>241 TLYFGRHSTT RELAIMVLMA YLSFMLAELF SLSGIITVFF CGVLMSHVTW HNVTESSRIT<br>301 SRHVFAMLSF IAETFLFLYV GTDALDFTKW KTSSLSFPGKS LGVSSVLLGL VLVGRAAFVF<br>361 PLSFLSNLSK KHPGEKITIR QQVVIWWAGL MRGAVSIALA FNKFTRAGHT QVRGNAIMIT<br>421 STIIVVLFST VVFGLLTKPL INLLIPHRNA TSMLSDDSSP KSLHSPLLTS QLISSIEEPT<br>481 QIPRPTNIRG EFMTMTRTVH RYWRKFDDKF MRPMFGGRGF VPFVPGSPTE RSSPDLSKA |
| 31 | 32396170 | AAP20431 | Na+/H+ antiporter NHX4 Zea mays subsp. mays | 1 MGYQVVAAQL KLASSADHAS VVIITLFVAL LCACIVLGHL LEENRWLNES ITALIIGLGT<br>61 GVVILLISRG KNSRLLVFSE DLFFIYLLPP IIFNAGFQVK KKQFFRNFMT ITLFGAVGTM<br>121 ISFFTISLGA IATFSRMSIG TLDVGDFLAI GAIFSATDSV CTLQVLHQDE TPFLYSLVFG<br>181 EGVVNDATSV VLFNAVQKIQ FTHINAWTAL QLIGNFLYLF STSTLLGIGT GLITAFVLKK<br>241 LYFGRHSTTR ELAIMILMAY LSYMLAELFS LSGLLTVFFC GVLMSHVRIE NVTESSRTTS<br>301 RHVFATLSFI SETFIFLYVG MDALDFEKWK TSSLSFGGTL GVSGVLMGLV MLGRAAFVFP<br>361 LSFLSNLAKK HQSEKISFRM QVVIWWAGLM RGAVSMALAL NKFTRSGHTQ LHGNAIMITS<br>421 TITVVLFSTM VFGMITKPLI RLLLPASGHP RELSEPSSPK SFHSPLLTSQ QGSDLESTTN<br>481 IVRPSSLRGL LTKPTHTVHY YWRKFDDALM RPVFGGRGFV PFVPGSPTER NPPDLSKA |
| 32 | 32396174 | AAP20432 | Na+/H+ antiporter NHX5 Zea mays subsp. mays | 1 MSMGYQVVAA QLKVASSADH ASVVIITLFV ALLCACIVLG HLLEENRWLN ESITALIIGL<br>61 CTGGVILMTT KGKSSHVLVF SEDLFFIYLL PPIIFIAGFQ VKKKQFFRNF MTITLFGAVG<br>121 TMISFFTISL GAIAIFSRMN IGTLDVGDFL AIGAIFSATD SVCTLQVLHQ DETPFLYSLV<br>181 FGEGVVNDAT SVVLFNAVQK IQITHINAEV ALQVFGNFLY LFSTSTLLGI ATGLITSFVL<br>241 KKLYFARHST TRELAIMMLM AYLSYMLAEL FSLSGILTVF FCGVLMSHVT WHNVTESSRI<br>301 TSRHVFAMLS FIAETFIFLY VGTDALDFDK WKTSSLSFGG TLGVSALIMA LVLLGRAAFV<br>361 FPLSVLTNFS NKHENESITF KHQVIIWWAG LMRGAVSIAL AFKQFTYSGV TLDPVNAAMV<br>421 TNTTIVVLFT TLVFGLLTKP LIRLLMPHRH LTMLSDDSTP KSLHSPLLTS QLGSDLEEPT<br>481 NIPRPSSIRG EFLTMTRTVH RYWRKFDDAF MRPMFGGRGF VPVVPGSPIE RSVPQWSEEA<br>541 HNKEP |
| 33 | 32396176 | AAP20433 | Na+/H+ antiporter NHX6 Zea mays subsp. mays | 1 MGLGVVAELV RLGVLSSTSD HASVVSINLF VALLCACIVL GHLLEENRWV NESITALIIG<br>61 LCTGVVILLT TKGKSSHILV FSEDLFFIYL LPPIIFNAGF QVKKQFFRN FMTITLFGAV<br>121 GTMISFFTIS LGALGLISRL NIGALELGDY LALGAIFSAT DSVCTLQVLS QDETPFLYSL<br>181 VFGEGVVNDA TSVVVFNALQ NFDITHIDAE VVFHLLGNPL YLFLLSTVLG VATGLISALV<br>241 IKKLYFGRHS TDREVALMML MAYLSYMLAE LFALSGILTV FFGCIVMSHY TWHNVTESSR<br>301 ITTKHAFATL SFLAETFLFL YVGMDALDID KWRSVSDTPG KSIAISSILM GLVMVGRAAF<br>361 VFPLSFLSNL AKKTEHEKIS WKQQVVIWWA GLMRGAVSMA LAYKKFTRAG HTQVRGNAIM<br>421 ITSTIIVVLF STMVFGLLTK PLINLLIPHR NATSMLSDDS SPKSLHSPLL TSQLGSDLEE<br>481 PTNIPRPSSI RGEFLTMTRT VSRYWRKFDD AFMRPMFGGR GFVPFVPGSP TERNPPDLSK<br>541 A |
| 34 | 22902099 | AAM54141 | Na+/H+ antiporter Gossypium hirsutum | 1 MVAPQLAAVF TKLQTLSSTD HASVVSMNIF VALLCACIVI GHLLEENRWM NESITALIIG<br>61 VFTGVIILLT SGGKSSHLLV FSEDLFFIYL LPPIIFNAGF QVKKKQFFRN FITIMLFGAV<br>121 GTLISCTIIS LGVINFFKEM DIGSLDIGDF LAIGAIFAAT DSVCTLQVLN QDETPLLYSL<br>181 VFGEGVVNDA TSVVLFNAIQ NVNTSPR ILLEFIGSFL YLFLASTMLG VIVGLVSAYI<br>241 IKKLYFGRHS TDREFALMML MAYLSYIMAE LFYLSGILTV FFCGIVMSHY TWHNVTESSR<br>301 VTTKHAFATL SFVAETFLFL YVGMDALDME KWRFVSDPG TSVAVSAVLM GLVMVGRAAF<br>361 VFPLSFLSNL AKKSTEKIS FREQIIIWWA GLMRGAVSMA LAYNQFTRGG HTQLRGNAIM<br>421 ITSTITIVLF STVVFGLMTK PLIRFLLPHP KPTASMLSDQ STPKSMEAPF LGSGQDSFDD<br>481 SLIGVHRPNS IRALLTTPAH TVHYYWRKFD NAFMRPMFGG RGFVPFVPGS PTERSEPNLP<br>541 QWQ |
| 35 | 30144703 | AAP15178 | Na+/H+ antiporter Suaeda maritima subsp. salsa | 1 MWSQLSSFFA SKMDMVSTSD HASVVSMNLF VALLCGCIVI GHLLEENRWM NESITALLIG<br>61 LSTGIIILLI SGGKSSHLLV FSEDLFFIYL LPPIIFNAGF QVKKKQFFRN FITIILFGAV<br>121 GTLVSFIIIS LGSIAIFQKM DIGSLELGDL LAIGAIFAAT DSVCTLQVLN QDETPLLYSL<br>181 VFGEGVVNDA TSVVLFNAIQ NFDLTHIDHR IAYRIAFQFG GNFLYLFFAS TLLGAVTGLL<br>241 SAYVIKKLYF GRHSTDREVA LMMLMAYLSY MLAELFYLSG ILTVFFCGIV MSHYTWHNVT<br>301 ESSRVTTKHA FATLSFVAEI FIFLYVGMDA LDIEKWRFVS DSPGTSVAVS SILLGLLMVG<br>361 RALLFSLVFL MNLSKKSNSE KVTFNQQIVI WWAGLMRGAV SVALAYNQFS RSGHTQLRGN<br>421 AIMITSTITV VLFSTMVFGL LTKPLILFML PQPKHFTSAS TVSDLGSPKS FSLPLLEDRQ<br>481 DSEADLGNDD EEAYPRGTIA RPTSLRMLLN APTHTVHHYW RRFDDYFMRP VFGGRGFVPF<br>541 VPGSPTEQST TNLSQRT |
| 36 | 28201131 | BAC56698 | Na+/H+ antiporter Hordeum | 1 MAFEVVAAQL ARLSDALATS DHASVVSINL FVALLCACIV LGHLLEENRW LNESITALII<br>61 GLCTGVVILM TTKGKSSHVL VFSEDLFFIY LLPPIIFNAG FQVKKKQFFR NFMTITLFGA<br>121 VGTMISFFTI SLAAIAIFSK MNIGTLDVSD FLAIGAIFSA TDSVCTLQVL NQDETPFLYS |

TABLE III-continued

| SEQ ID NUMBER No (GI) | PROTEIN ACCESSION | PROTEIN DESCRIPTION (SPECIES) | SEQUENCE | |
|---|---|---|---|---|
| | | vulgare | 181 | LVFGEGVVND ATSVVLFNAL QNFDPNQIDA IVILKFLGNF CYLFVSSTFL GVFSGLLSAY |
| | | | 241 | IIKKLYIGRH STDREVALMM LMAYLSYMLA ELLDLSGILT VFFCGIVMSH YTWHNVTESS |
| | | | 301 | RVTTKHAFAT LSFIAETFLF LYVGMDALDI EKWKFASDSP GKSIGISSIL LGLVLVGRAA |
| | | | 361 | FVFPLSFLSN LTKKTELEKI SWRQQIVIWW AGLMRGAVSI ALAYNKFTRS GHTQLHGNAI |
| | | | 421 | MITSTITVVL FSTMLFGILT KPLIRFLLPA SSNGDPSEPS SPKSLHSPLL TSMLGSDMEA |
| | | | 481 | PLPIVRPSSL RMLITKPTHT IHYYWRKFDD ALMRPMFGGR GFVPYSPGSP TDPNVIVA |
| 37 27948863 | AAO25547 | Na+/H+ antiporter Hordeum brevisubulatum | 1 | MGWGLGDPPA DYGSIMAVGL FVALMCICII VGHLLEENRW MNESTTALLL GLGAGTVILF |
| | | | 61 | ASSGKNSRLM VFSEDLFFIY LLPPIIFNAG FQVKKKQFFR NFMTITLFAV VGTLISFSII |
| | | | 121 | SLGAMGLISR LWIGALELGD YLALGAIFSA TDSVCTLQVL SQDETPFLYS LVFGEGVVND |
| | | | 181 | ATSVVLFNAI QNFDLGNFSS LKFLQFIGNF LYLFGASTFL GVASGLLSAY VIKKLYFGRH |
| | | | 241 | STDREVAIMM LMAYLSYMLA ELLDLSGILT VFFCGIVMSH YTWHNVTESS RVTTKHAFAT |
| | | | 301 | LSFISETPLF LYVGMDALDI EKWKIVSETY SPMKSITLSS IILALVLVAR AAFVFPLSYL |
| | | | 361 | SNLTKKTAGE KISIRQQVII WWAGLMRGAV SIALAYNKFA KSGHTQLPSN AIMITSTIII |
| | | | 421 | VLFSTIVFGL LTKPLIRLLI PARHLTREVS ALSEPSSPKS FLEQLTVNGP ETDVENGVSI |
| | | | 481 | RRPTSLRMLL ASPTRSVHHY WRKFDNAFMR PVFGGRGFVP FVPGSPTESS VPLLAHGSEN |
| 38 29825705 | AAO91943 | Vacuolar Na+/H+ antiporter Hordeum vulgare | 1 | MGPDLGALAL RYTGLAVSDH DSIVAINIFI ALLCGCIVFG HLLEGNRWVN ESTTAIVLGL |
| | | | 61 | ITGGVILLCT KGVNSRILIF SEDIFFIYLL PPIIFNAGFQ VKKKQFFRNF ATIILFGAVG |
| | | | 121 | TLISFVIITL GAMGLFRKLD VGPLELGDYL AIGAIFSATD SVCTLQVLNQ DQAPLLYSLV |
| | | | 181 | FGEGVVNDAT SVVLFNAIQN IDLNHFDVLV LLQLIGKFLY LFLTSTVLGV AAGLLSAYII |
| | | | 241 | KKLCFARHST DREVAIMILM AYLSYMLSML LDLSGILTVF FCGIVMSHYT RHNVTESSRV |
| | | | 301 | TTKHTFATLS FIAEIFLFLY VGMDALDIDK WKLASSSPKK PIALSAVILG LVMVGRAAFV |
| | | | 361 | FPLSYLSNLS KKESHPKISF NQQVIIWWAG LMRGAVSIAL AYNKYTTSGH TAVRVNAVMI |
| | | | 421 | TSTIIVVLFS TMVFGLLTKP LINLLVPPRP GTAADISSQS FLDPLTASLL GSDFDVGQLT |
| | | | 481 | PQTNLQYLLT MPSRSVHRVW RKFDDKFMRP MFGGRGFVPF VPGSPIERSV HGPGLLGTVT |
| | | | 541 | EAENRS | |

TABLE IV

Plant and fruit yield of wild-type (WT) tomato plants grown in the presence of 5 mM NaCl and T2 transgenic plants overexpressing AtNHX1 (OEX1) grown in the presence of 5 mM and 200 mM NaCl. Plants were harvested 12 weeks after germination. Each value is the Mean ± SD (n = 10 individual plants).

| | WT | OEX1 | |
|---|---|---|---|
| | (5 mM NaCl) | (5 mM NaCl) | (200 mM NaCl) |
| Height (cm) | 124.0 ± 8.2 | 128.8 ± 9.5 | 107.6 ± 5.2 |
| Fresh Weight (g) (without fruit) | 1,270 ± 103 | 1,329 ± 110 | 1,123 ± 134 |
| Fruit per plant | 17.2 ± 1.3 | 17.8 ± .6 | 18.4 ± 1.5 |
| Fruit weight (g) | 119.5 ± 13.4 | 116.7 ± 9.0 | 105.7 ± 6.7 |
| Fruit water content(%) | 90.8 ± 3.2 | 90.2 ± 2.2 | 90.7 ± 2.3 |
| Solid solute content (° Brix) | 4.2 ± 0.6 | 4.4 ± 0.7 | 4.2 ± 0.5 |

TABLE V

Relative yield decrease of representative plants.

| | RELATIVE YIELD DECREASE | | | |
|---|---|---|---|---|
| | 25% | | 50% | |
| CROP | (mmho/cm) | (mM NaCl) | (mmho/cm) | (mM NaCl) |
| Barley | 13 | 120 | 18 | 170 |
| Sugarbeet | 11 | 105 | 15 | 150 |
| Sorghum | 7.2 | 65 | 11 | 100 |
| Soybean | 6.2 | 59 | 7.5 | 65 |
| Rice | 3.8 | 36 | 5.9 | 50 |
| Corn | 3.8 | 36 | 5.9 | 50 |
| Alfalfa | 5.4 | 45 | 8.8 | 75 |
| Cucumber | 4.4 | 40 | 7.0 | 65 |
| Potato | 2.8 | 36 | 5.9 | 50 |
| Beans | 2.3 | 18 | 3.2 | 28 |
| Grape | 4.1 | 37 | 6.7 | 62 |
| Orange | 3.2 | 28 | 4.8 | 43 |
| Peach | 2.9 | 25 | 4.1 | 35 |
| Strawberry | 1.8 | 14 | 2.5 | 21 |

We claim:

1. A method of lowering the salt content of soil, said method comprising:
   a) cultivating in the soil a transgenic plant comprising a recombinant nucleic acid encoding a vacuolar Na$^+$/H$^+$ transporter, wherein the recombinant nucleic acid is the nucleic acid molecule of SEQ ID NO:1 or a nucleic acid molecule encoding SEQ ID NO: 2 and the soil has an initial electrical conductivity; and
   b) harvesting the transgenic plant.

2. The method of claim 1, wherein the initial electrical conductivity of the soil is at least 20 dS/M.

3. The method of claim 1, wherein the transgenic plant further comprises a second recombinant nucleic acid operably linked to the recombinant nucleic acid encoding a vacuolar Na$^+$/H$^+$ transporter, wherein the second recombinant nucleic acid comprises a plant promoter.

4. The method of claim 3, wherein the plant promoter is a 35S promoter.

5. The method of claim 3, wherein the plant promoter is a CaMV promoter.

6. The method of claim 1, wherein the transgenic plant is canola or safflower.

7. The method of claim 6, wherein the transgenic plant is canola.

8. The method of claim 6, wherein the transgenic plant is safflower.

* * * * *

SEQUENCE LISTING

<160> NUMBER OF SEQ ID NOS: 38

<210> SEQ ID NO 1

```
<211> LENGTH: 2178
<212> TYPE: DNA
<213> ORGANISM: Arabidopsis thaliana

<400> SEQUENCE: 1
cctctctgtt tcgttcctcg tagacgaaga agaagaagaa tctcaggttt tagctttcga      60
agcttccaaa attttgaatt ttgatcttct gggctctttt gtaaatcaga ctgaagatat     120
ttagattacc cagaagttgt tcaaggaatg gtttcagtgg acagcacgga aagataaaag     180
agacttttt  ttccagattt tgctgatcca aaatctgaat agttgttcat gttcttggat     240
caaatctgga agaggaagt  ttgttggatc tagaagaaga taacaatgtt ggattctcta     300
gtgtcgaaac tgccttcgtt atcgacatct gatcacgctt ctgtggttgc gttgaatctc     360
tttgttgcac ttctttgtgc ttgtattgtt cttggtcatc ttttggaaga gaatagatgg     420
atgaacgaat ccatcaccgc cttgttgatt gggctaggca ctggtgttac cattttgttg     480
attagtaaag gaaaagctc  gcatcttctc gtctttagtg aagatctttt cttcatatat     540
cttttgccac ccattatatt caatgcaggg tttcaagtaa aaagaagca  gttttttccgc    600
aatttcgtga ctattatgct ttttggtgct gttgggacta ttatttcttg cacaatcata     660
tctctaggtg taacacagtt cttaagaag  ttggacattg aacctttga  cttgggtgat     720
tatcttgcta ttggtgccat atttgctgca acagattcag tatgtacact gcaggttctg     780
aatcaagacg agacaccttt gctttacagt cttgtattcg gagagggtgt tgtgaatgat     840
gcaacgtcag ttgtggtctt caacgcgatt cagagctttg atctcactca cctaaaccac     900
gaagctgctt tcatcttct  tggaaacttc ttgtatttgt ttctcctaag taccttgctt     960
ggtgctgcaa ccggtctgat aagtgcgtat gttatcaaga agctatactt tggaaggcac    1020
tcaactgacc gagaggttgc ccttatgatg cttatggcgt atctttctta tatgcttgct    1080
gagcttttcg acttgagcgg tatcctcact gtgtttttct gtggtattgt gatgtcccat    1140
tacacatggc acaatgtaac ggagagctca agaataacaa caaagcatac ctttgcaact    1200
ttgtcatttc ttgcggagac atttattttc ttgtatgttg gaatggatgc cttggacatt    1260
gacaagtgga gatccgtgag tgacacaccg ggaacatcga tcgcagtgag ctcaatccta    1320
atgggtctgg tcatggttgg aagagcagcg ttcgtctttc cgttatcgtt tctatctaac    1380
ttagccaaga gaatcaaag  cgagaaaatc aactttaaca tgcaggttgt gatttggtgg    1440
tctggtctca tgagaggtgc tgtatctatg gctcttgcat acaacaagtt tacaagggcc    1500
gggcacacag atgtacgcgg gaatgcaatc atgatcacga gtacgataac tgtctgtctt    1560
tttagcacag tggtgtttgg tatgctgacc aaaccactca taagctacct attaccgcac    1620
cagaacgcca ccacgagcat gttatctgat gacaacaccc caaaatccat acatatccct    1680
ttgttggacc aagactcgtt cattgagcct tcagggaacc acaatgtgcc tcggcctgac    1740
agtatacgtg gcttcttgac acggcccact cgaaccgtgc attactactg gagacaattt    1800
gatgactcct tcatgcgacc cgtctttgga ggtcgtggct ttgtaccctt tgttccaggt    1860
tctccaactg agagaaaccc tcctgatctt agtaaggctt gagggtaacg tggaagaaaa    1920
gctttgattt tttttggtag aaaagggtga ttcaaattat gcttttgtgt aaattatcca    1980
tttgtaatat tgtttgtgag gacagaaatc tgtcctaacg tttgagagc  agaaagcaaa    2040
acatggcaac tttgaagtgt tgattgatg  tatgtaatta tattcatatt tgttttgttg    2100
taacacaaac tacacatttg tttatgtttt gaatttggtt tttgcttcga aaaaaaaaa     2160
aaaaaaaaaa aaaaaaaa                                                  2178
```

<210> SEQ ID NO 2
<211> LENGTH: 538
<212> TYPE: PRT
<213> ORGANISM: Arabidopsis thaliana

<400> SEQUENCE: 2

| | | | | | | | | | | | | | | |
|---|---|---|---|---|---|---|---|---|---|---|---|---|---|---|
| Met | Leu | Asp | Ser | Leu | Val | Ser | Lys | Leu | Pro | Ser | Leu | Ser | Thr | Ser | Asp |
| 1 | | | | 5 | | | | | 10 | | | | | 15 | |
| His | Ala | Ser | Val | Val | Ala | Leu | Asn | Leu | Phe | Val | Ala | Leu | Leu | Cys | Ala |
| | | | 20 | | | | | 25 | | | | | 30 | | |
| Cys | Ile | Val | Leu | Gly | His | Leu | Leu | Glu | Glu | Asn | Arg | Trp | Met | Asn | Glu |
| | | 35 | | | | | 40 | | | | | 45 | | | |
| Ser | Ile | Thr | Ala | Leu | Leu | Ile | Gly | Leu | Gly | Thr | Gly | Val | Thr | Ile | Leu |
| 50 | | | | | 55 | | | | | 60 | | | | | |
| Leu | Ile | Ser | Lys | Gly | Lys | Ser | Ser | His | Leu | Leu | Val | Phe | Ser | Glu | Asp |
| 65 | | | | | 70 | | | | | 75 | | | | | 80 |
| Leu | Phe | Phe | Ile | Tyr | Leu | Leu | Pro | Pro | Ile | Ile | Phe | Asn | Ala | Gly | Phe |
| | | | | 85 | | | | | 90 | | | | | 95 | |
| Gln | Val | Lys | Lys | Lys | Gln | Phe | Phe | Arg | Asn | Phe | Val | Thr | Ile | Met | Leu |
| | | | 100 | | | | | 105 | | | | | 110 | | |
| Phe | Gly | Ala | Val | Gly | Thr | Ile | Ile | Ser | Cys | Thr | Ile | Ile | Ser | Leu | Gly |
| | | 115 | | | | | 120 | | | | | 125 | | | |
| Val | Thr | Gln | Phe | Phe | Lys | Lys | Leu | Asp | Ile | Gly | Thr | Phe | Asp | Leu | Gly |
| 130 | | | | | 135 | | | | | 140 | | | | | |
| Asp | Tyr | Leu | Ala | Ile | Gly | Ala | Ile | Phe | Ala | Ala | Thr | Asp | Ser | Val | Cys |
| 145 | | | | | 150 | | | | | 155 | | | | | 160 |
| Thr | Leu | Gln | Val | Leu | Asn | Gln | Asp | Glu | Thr | Pro | Leu | Leu | Tyr | Ser | Leu |
| | | | | 165 | | | | | 170 | | | | | 175 | |
| Val | Phe | Gly | Glu | Gly | Val | Val | Asn | Asp | Ala | Thr | Ser | Val | Val | Val | Phe |
| | | | 180 | | | | | 185 | | | | | 190 | | |
| Asn | Ala | Ile | Gln | Ser | Phe | Asp | Leu | Thr | His | Leu | Asn | His | Glu | Ala | Ala |
| | | 195 | | | | | 200 | | | | | 205 | | | |
| Phe | His | Leu | Leu | Gly | Asn | Phe | Leu | Tyr | Leu | Phe | Leu | Leu | Ser | Thr | Leu |
| 210 | | | | | 215 | | | | | 220 | | | | | |
| Leu | Gly | Ala | Ala | Thr | Gly | Leu | Ile | Ser | Ala | Tyr | Val | Ile | Lys | Lys | Leu |
| 225 | | | | | 230 | | | | | 235 | | | | | 240 |
| Tyr | Phe | Gly | Arg | His | Ser | Thr | Asp | Arg | Glu | Val | Ala | Leu | Met | Met | Leu |
| | | | | 245 | | | | | 250 | | | | | 255 | |
| Met | Ala | Tyr | Leu | Ser | Tyr | Met | Leu | Ala | Glu | Leu | Phe | Asp | Leu | Ser | Gly |
| | | | 260 | | | | | 265 | | | | | 270 | | |
| Ile | Leu | Thr | Val | Phe | Phe | Cys | Gly | Ile | Val | Met | Ser | His | Tyr | Thr | Trp |
| | | 275 | | | | | 280 | | | | | 285 | | | |
| His | Asn | Val | Thr | Glu | Ser | Ser | Arg | Ile | Thr | Thr | Lys | His | Thr | Phe | Ala |
| | 290 | | | | | 295 | | | | | 300 | | | | |
| Thr | Leu | Ser | Phe | Leu | Ala | Glu | Thr | Phe | Ile | Phe | Leu | Tyr | Val | Gly | Met |
| 305 | | | | | 310 | | | | | 315 | | | | | 320 |
| Asp | Ala | Leu | Asp | Ile | Asp | Lys | Trp | Arg | Ser | Val | Ser | Asp | Thr | Pro | Gly |
| | | | | 325 | | | | | 330 | | | | | 335 | |
| Thr | Ser | Ile | Ala | Val | Ser | Ser | Ile | Leu | Met | Gly | Leu | Val | Met | Val | Gly |
| | | | 340 | | | | | 345 | | | | | 350 | | |
| Arg | Ala | Ala | Phe | Val | Phe | Pro | Leu | Ser | Phe | Leu | Ser | Asn | Leu | Ala | Lys |
| | | 355 | | | | | 360 | | | | | 365 | | | |
| Lys | Asn | Gln | Ser | Glu | Lys | Ile | Asn | Phe | Asn | Met | Gln | Val | Val | Ile | Trp |
| 370 | | | | | 375 | | | | | 380 | | | | | |

```
Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
            405                 410                 415

Ile Thr Ser Thr Ile Thr Val Cys Leu Phe Ser Thr Val Phe Gly
        420                 425                 430

Met Leu Thr Lys Pro Leu Ile Ser Tyr Leu Leu Pro His Gln Asn Ala
            435                 440                 445

Thr Thr Ser Met Leu Ser Asp Asp Asn Thr Pro Lys Ser Ile His Ile
        450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu Thr Arg Pro Thr Arg
            485                 490                 495

Thr Val His Tyr Tyr Trp Arg Gln Phe Asp Asp Ser Phe Met Arg Pro
            500                 505                 510

Val Phe Gly Gly Arg Gly Phe Val Pro Phe Val Pro Gly Ser Pro Thr
            515                 520                 525

Glu Arg Asn Pro Pro Asp Leu Ser Lys Ala
            530                 535

<210> SEQ ID NO 3
<211> LENGTH: 542
<212> TYPE: PRT
<213> ORGANISM: Ipomoea nil

<400> SEQUENCE: 3

Met Ala Phe Gly Leu Ser Ser Leu Leu Gln Asn Ser Asp Leu Phe Thr
1               5                   10                  15

Ser Asp His Ala Ser Val Val Ser Met Asn Leu Phe Val Ala Leu Leu
            20                  25                  30

Cys Ala Cys Ile Val Leu Gly His Leu Glu Glu Asn Arg Trp Val
        35                  40                  45

Asn Glu Ser Ile Thr Ala Leu Ile Ile Gly Leu Cys Thr Gly Val Val
50                  55                  60

Ile Leu Leu Leu Ser Gly Gly Lys Ser Ser His Leu Leu Val Phe Ser
65                  70                  75                  80

Glu Asp Leu Phe Phe Ile Tyr Leu Leu Pro Pro Ile Ile Phe Asn Ala
                85                  90                  95

Gly Phe Gln Val Lys Lys Lys Gln Phe Phe Val Asn Phe Met Thr Ile
            100                 105                 110

Met Leu Phe Gly Ala Ile Gly Thr Leu Ile Ser Cys Ser Ile Ile Ser
            115                 120                 125

Phe Gly Ala Val Lys Ile Phe Lys His Leu Asp Ile Asp Phe Leu Asp
130                 135                 140

Phe Gly Asp Tyr Leu Ala Ile Gly Ala Ile Phe Ala Ala Thr Asp Ser
145                 150                 155                 160

Val Cys Thr Leu Gln Val Leu Ser Gln Asp Glu Thr Pro Leu Leu Tyr
            165                 170                 175

Ser Leu Val Phe Gly Glu Gly Val Val Asn Asp Ala Thr Ser Val Val
            180                 185                 190

Leu Phe Asn Ala Ile Gln Ser Phe Asp Met Thr Ser Phe Asp Pro Lys
        195                 200                 205

Ile Gly Leu His Phe Ile Gly Asn Phe Leu Tyr Leu Phe Leu Ser Ser
    210                 215                 220
```

```
Thr Phe Leu Gly Val Gly Ile Gly Leu Leu Cys Ala Tyr Ile Ile Lys
225                 230                 235                 240

Lys Leu Tyr Phe Gly Arg His Ser Thr Asp Arg Glu Val Ala Leu Met
            245                 250                 255

Met Leu Met Ser Tyr Leu Ser Tyr Ile Met Ala Glu Leu Phe Tyr Leu
        260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Val Thr Thr Arg His Ser
290                 295                 300

Phe Ala Thr Leu Ser Phe Val Ala Glu Thr Phe Ile Phe Leu Tyr Val
305                 310                 315                 320

Gly Met Asp Ala Leu Asp Ile Glu Lys Trp Lys Phe Val Lys Asn Ser
                325                 330                 335

Gln Gly Leu Ser Val Ala Val Ser Ser Ile Leu Val Gly Leu Ile Leu
            340                 345                 350

Val Gly Arg Ala Ala Phe Val Phe Pro Leu Ser Phe Leu Ser Asn Leu
        355                 360                 365

Ala Lys Lys Asn Ser Ser Asp Lys Ile Ser Phe Arg Gln Gln Ile Ile
370                 375                 380

Ile Trp Trp Ala Gly Leu Met Arg Gly Ala Val Ser Ile Ala Leu Ala
385                 390                 395                 400

Tyr Asn Lys Phe Thr Thr Ser Gly His Thr Ser Leu His Glu Asn Ala
                405                 410                 415

Ile Met Ile Thr Ser Thr Val Thr Val Val Leu Phe Ser Thr Val Val
            420                 425                 430

Phe Gly Leu Met Thr Lys Pro Leu Ile Asn Leu Leu Leu Pro Pro His
        435                 440                 445

Lys Gln Met Pro Ser Gly His Ser Ser Met Thr Thr Ser Glu Pro Ser
450                 455                 460

Ser Pro Lys His Phe Thr Val Pro Leu Leu Asp Asn Gln Pro Asp Ser
465                 470                 475                 480

Glu Ser Asp Met Ile Thr Gly Pro Glu Val Ala Arg Pro Thr Ala Leu
                485                 490                 495

Arg Met Leu Leu Arg Thr Pro Thr His Thr Val His Arg Tyr Trp Arg
            500                 505                 510

Lys Phe Asp Asp Ser Phe Met Arg Pro Val Phe Gly Gly Arg Gly Phe
        515                 520                 525

Val Pro Phe Val Ala Gly Ser Pro Val Glu Gln Ser Pro Arg
530                 535                 540

<210> SEQ ID NO 4
<211> LENGTH: 556
<212> TYPE: PRT
<213> ORGANISM: Suaeda maritima

<400> SEQUENCE: 4

Met Leu Ser Gln Leu Ser Ser Phe Phe Ala Ser Lys Met Asp Met Val
1               5                   10                  15

Ser Thr Ser Asp His Ala Ser Val Val Ser Met Asn Leu Phe Val Ala
            20                  25                  30

Leu Leu Arg Gly Cys Ile Val Ile Gly His Leu Leu Glu Glu Asn Arg
        35                  40                  45

Trp Met Asn Glu Ser Ile Thr Ala Leu Leu Ile Gly Leu Ser Thr Gly
    50                  55                  60
```

-continued

```
Ile Ile Ile Leu Leu Ile Ser Gly Gly Lys Ser Ser His Leu Leu Val
 65                  70                  75                  80

Phe Ser Glu Asp Leu Phe Phe Ile Tyr Leu Pro Pro Ile Ile Phe
             85                  90                  95

Asn Ala Gly Phe Gln Val Lys Lys Gln Phe Phe Arg Asn Phe Ile
            100                 105                 110

Thr Ile Ile Leu Phe Gly Ala Val Gly Thr Leu Val Ser Phe Ile Ile
            115                 120                 125

Ile Ser Leu Gly Ser Ile Ala Ile Phe Gln Lys Met Asp Ile Gly Ser
        130                 135                 140

Leu Glu Leu Gly Asp Leu Leu Ala Ile Gly Ala Ile Phe Ala Ala Thr
145                 150                 155                 160

Asp Ser Val Cys Thr Leu Gln Val Leu Asn Gln Asp Glu Thr Pro Leu
                165                 170                 175

Leu Tyr Ser Leu Val Phe Gly Glu Gly Val Val Asn Asp Ala Thr Ser
            180                 185                 190

Val Val Leu Phe Asn Ala Ile Gln Asn Phe Asp Leu Thr His Ile Asp
        195                 200                 205

His Arg Ile Ala Phe Gln Phe Gly Gly Asn Phe Leu Tyr Leu Phe Phe
210                 215                 220

Ala Ser Thr Leu Leu Gly Ala Val Thr Gly Leu Leu Ser Ala Tyr Val
225                 230                 235                 240

Ile Lys Lys Leu Tyr Phe Gly Arg His Ser Thr Asp Arg Glu Val Ala
                245                 250                 255

Leu Met Met Leu Met Ala Tyr Leu Ser Tyr Met Leu Ala Glu Leu Phe
                260                 265                 270

Tyr Leu Ser Gly Ile Leu Thr Val Phe Phe Cys Gly Ile Val Met Ser
            275                 280                 285

His Tyr Thr Trp His Asn Val Thr Glu Ser Ser Arg Val Thr Thr Lys
        290                 295                 300

His Ala Phe Ala Thr Leu Ser Phe Val Ala Glu Ile Phe Ile Phe Leu
305                 310                 315                 320

Tyr Val Gly Met Asp Ala Leu Asp Ile Glu Lys Trp Arg Phe Val Ser
                325                 330                 335

Asp Ser Pro Gly Thr Ser Val Ala Val Ser Ser Ile Leu Leu Gly Leu
                340                 345                 350

His Met Val Gly Arg Ala Ala Phe Val Phe Pro Phe Ala Phe Leu Met
            355                 360                 365

Asn Leu Ser Lys Lys Ser Asn Ser Glu Lys Val Thr Phe Asn Gln Gln
        370                 375                 380

Ile Val Ile Trp Trp Ala Gly Leu Met Lys Ser Ala Val Ser Val Ala
385                 390                 395                 400

Leu Ala Tyr Asn Gln Phe Ser Arg Ser Gly His Thr Gln Leu Arg Gly
                405                 410                 415

Asn Ala Ile Met Ile Thr Ser Thr Ile Thr Val Val Leu Phe Ser Thr
            420                 425                 430

Met Val Phe Gly Leu Leu Thr Lys Pro Leu Ile Leu Phe Met Leu Pro
        435                 440                 445

Gln Pro Lys His Phe Thr Ser Ala Ser Thr Val Ser Asp Leu Gly Ser
450                 455                 460

Pro Lys Ser Phe Ser Leu Pro Leu Leu Glu Asp Arg Gln Asp Ser Glu
465                 470                 475                 480

Ala Asp Leu Gly Asn Asp Asp Glu Glu Ala Tyr Pro Arg Gly Thr Ile
                485                 490                 495
```

```
Ala Arg Pro Thr Ser Leu Arg Met Leu Leu Asn Ala Pro Thr His Thr
                500                 505                 510

Val His His Tyr Trp Arg Arg Phe Asp Asp Tyr Phe Met Arg Pro Val
        515                 520                 525

Phe Gly Gly Arg Gly Phe Val Pro Phe Val Pro Gly Ser Pro Thr Glu
    530                 535                 540

Gln Ser Ile Thr Asn Phe Val Thr Glu Asn Ile Ser
545                 550                 555

<210> SEQ ID NO 5
<211> LENGTH: 540
<212> TYPE: PRT
<213> ORGANISM: Petunia x hybrida

<400> SEQUENCE: 5

Met Ala Phe Asp Phe Gly Thr Leu Leu Gly Asn Val Asp Arg Leu Ser
  1               5                  10                  15

Thr Ser Asp His Gln Ser Val Val Ser Ile Asn Leu Phe Val Ala Leu
             20                  25                  30

Ile Cys Ala Cys Ile Val Ile Gly His Leu Leu Glu Glu Asn Arg Trp
         35                  40                  45

Met Asn Glu Ser Ile Thr Ala Leu Val Ile Gly Ser Cys Thr Gly Ile
     50                  55                  60

Val Ile Leu Leu Ile Ser Gly Gly Lys Asn Ser His Ile Leu Val Phe
 65                  70                  75                  80

Ser Glu Asp Leu Phe Phe Ile Tyr Leu Leu Pro Pro Ile Ile Phe Asn
                 85                  90                  95

Ala Gly Phe Gln Val Lys Lys Lys Ser Phe Phe Arg Asn Phe Ser Thr
            100                 105                 110

Ile Met Leu Phe Gly Ala Leu Gly Thr Leu Ile Ser Phe Ile Ile Ile
        115                 120                 125

Ser Leu Gly Ala Ile Gly Ile Phe Lys Lys Met Asn Ile Gly Ser Leu
    130                 135                 140

Glu Ile Gly Asp Tyr Leu Ala Ile Gly Ala Ile Phe Ser Ala Thr Asp
145                 150                 155                 160

Ser Val Cys Thr Leu Gln Val Leu Asn Gln Asp Glu Thr Pro Leu Leu
                165                 170                 175

Tyr Ser Leu Val Phe Gly Glu Gly Val Val Asn Asp Ala Thr Ser Val
            180                 185                 190

Val Leu Phe Asn Ala Ile Gln Asn Phe Asp Leu Ser His Ile Asp Thr
        195                 200                 205

Gly Lys Ala Met Glu Leu Val Gly Asn Phe Leu Tyr Leu Phe Ala Ser
    210                 215                 220

Ser Thr Ala Leu Gly Val Ala Ala Gly Leu Leu Ser Ala Tyr Ile Ile
225                 230                 235                 240

Lys Lys Leu Tyr Phe Gly Arg His Ser Thr Asp Arg Glu Val Ala Ile
                245                 250                 255

Met Ile Leu Met Ala Tyr Leu Ser Tyr Met Leu Ala Glu Leu Phe Tyr
            260                 265                 270

Leu Ser Ala Ile Leu Thr Val Phe Phe Ser Gly Ile Val Met Ser His
        275                 280                 285

Tyr Thr Trp His Asn Val Thr Glu Ser Ser Arg Val Thr Thr Lys His
    290                 295                 300

Thr Phe Ala Thr Leu Ser Phe Ile Ala Glu Ile Phe Ile Phe Leu Tyr
305                 310                 315                 320
```

```
Val Gly Met Asp Ala Leu Asp Ile Glu Lys Trp Lys Phe Val Ser Asp
            325                 330                 335

Ser Pro Gly Ile Ser Val Gln Val Ser Ser Ile Leu Leu Gly Leu Val
            340                 345                 350

Leu Val Gly Arg Ala Ala Phe Val Phe Pro Leu Ser Phe Leu Ser Asn
            355                 360                 365

Leu Thr Lys Lys Thr Pro Glu Ala Lys Ile Ser Phe Asn Gln Gln Val
            370                 375                 380

Thr Ile Trp Trp Ala Gly Leu Met Arg Gly Ala Val Ser Met Ala Leu
385                 390                 395                 400

Ala Tyr Asn Gln Phe Thr Arg Gly Gly His Thr Gln Leu Arg Ala Asn
            405                 410                 415

Ala Ile Met Ile Thr Ser Thr Ile Thr Val Val Leu Phe Ser Thr Val
            420                 425                 430

Val Phe Gly Leu Met Thr Lys Pro Leu Ile Arg Ile Leu Leu Pro Ser
            435                 440                 445

His Lys His Leu Ser Arg Met Ile Ser Ser Glu Pro Thr Thr Pro Lys
            450                 455                 460

Ser Phe Ile Val Pro Leu Leu Asp Ser Thr Gln Asp Ser Glu Ala Asp
465                 470                 475                 480

Leu Glu Arg His Val Pro Arg Pro His Ser Leu Arg Met Leu Leu Ser
            485                 490                 495

Thr Pro Ser His Thr Val His Tyr Tyr Trp Arg Lys Phe Asp Asn Ala
            500                 505                 510

Phe Met Arg Pro Val Phe Gly Gly Arg Gly Phe Val Pro Phe Ala Pro
            515                 520                 525

Gly Ser Pro Thr Asp Pro Val Gly Gly Asn Leu Gln
            530                 535                 540

<210> SEQ ID NO 6
<211> LENGTH: 555
<212> TYPE: PRT
<213> ORGANISM: Torenia hybrida

<400> SEQUENCE: 6

Met Gly Phe Glu Ser Val Ile Lys Leu Ala Ala Ser Glu Thr Asp Asn
1               5                   10                  15

Leu Trp Ser Ser Gly His Gly Ser Val Val Ala Ile Thr Leu Phe Val
            20                  25                  30

Thr Leu Leu Cys Thr Cys Ile Val Ile Gly His Leu Glu Glu Asn
            35                  40                  45

Arg Trp Met Asn Glu Ser Ile Ile Ala Leu Ile Gly Leu Ala Thr
    50                  55                  60

Gly Val Ile Ile Leu Leu Ile Ser Gly Gly Lys Ser Ser His Leu Leu
65                  70                  75                  80

Val Phe Ser Glu Asp Leu Phe Ile Tyr Ala Leu Pro Pro Ile Ile
                85                  90                  95

Phe Asn Ala Gly Phe Gln Val Lys Lys Lys Ser Phe Phe Arg Asn Phe
            100                 105                 110

Ala Thr Ile Met Met Phe Gly Ala Val Gly Thr Leu Ile Ser Phe Ile
            115                 120                 125

Ile Ile Ser Leu Gly Thr Ile Ala Phe Phe Pro Lys Met Asn Met Arg
            130                 135                 140

Leu Gly Val Gly Asp Tyr Leu Ala Ile Gly Ala Ile Phe Ala Ala Thr
145                 150                 155                 160
```

```
Asp Ser Val Cys Thr Leu Gln Val Leu Ser Gln Asp Glu Thr Pro Leu
                165                 170                 175

Leu Tyr Ser Leu Val Phe Gly Glu Gly Val Val Asn Asp Ala Thr Ser
            180                 185                 190

Val Val Leu Phe Asn Ala Val Gln Asn Phe Asp Leu Pro His Met Ser
        195                 200                 205

Thr Ala Lys Ala Phe Glu Leu Val Gly Asn Phe Phe Tyr Leu Phe Ala
    210                 215                 220

Thr Ser Thr Val Leu Gly Val Leu Thr Gly Leu Leu Ser Ala Tyr Ile
225                 230                 235                 240

Ile Lys Lys Leu Tyr Phe Gly Arg His Ser Thr Asp Arg Glu Val Ala
                245                 250                 255

Ile Met Ile Leu Met Ala Tyr Leu Ser Tyr Met Leu Ala Glu Leu Phe
            260                 265                 270

Asp Leu Ser Gly Ile Leu Thr Val Phe Phe Cys Gly Ile Val Met Ser
        275                 280                 285

His Tyr Thr Trp His Asn Val Thr Glu Asn Ser Arg Val Thr Thr Lys
    290                 295                 300

His Thr Phe Ala Thr Leu Ser Phe Val Ala Glu Ile Phe Ile Phe Leu
305                 310                 315                 320

Tyr Val Gly Met Asp Ala Leu Asp Ile Glu Lys Trp Arg Phe Val Ser
                325                 330                 335

Gly Ser Met Thr Thr Ser Ala Ala Val Ser Ala Thr Leu Leu Gly Leu
            340                 345                 350

Val Leu Leu Ser Arg Ala Ala Phe Val Phe Pro Leu Ser Phe Leu Ser
        355                 360                 365

Asn Leu Ala Lys Lys Ser Pro Leu Glu Lys Ile Ser Leu Arg Gln Gln
    370                 375                 380

Ile Ile Ile Trp Trp Ala Gly Leu Met Arg Gly Ala Val Ser Met Ala
385                 390                 395                 400

Leu Ala Tyr Lys Gln Phe Thr Arg Glu Gly Leu Thr Val Glu Arg Glu
                405                 410                 415

Asn Ala Ile Phe Ile Thr Ser Thr Ile Thr Ile Val Leu Phe Ser Thr
            420                 425                 430

Val Val Phe Gly Leu Met Thr Lys Pro Leu Ile Asn Leu Leu Ile Pro
        435                 440                 445

Ser Pro Lys Leu Asn Arg Ser Val Ser Ser Glu Pro Leu Thr Pro Asn
    450                 455                 460

Ser Ile Thr Ile Pro Leu Leu Gly Glu Ser Gln Asp Ser Val Ala Glu
465                 470                 475                 480

Leu Phe Ser Ile Arg Gly Gln Thr Ser Gln Gly Gly Glu Pro Val Ala
                485                 490                 495

Arg Pro Ser Ser Leu Arg Met Leu Leu Thr Lys Pro Thr His Thr Val
            500                 505                 510

His Tyr Tyr Trp Arg Lys Phe Asp Asn Ala Phe Met Arg Pro Val Phe
        515                 520                 525

Gly Gly Arg Gly Phe Val Pro Tyr Val Pro Gly Ser Pro Thr Glu Arg
    530                 535                 540

Ser Val Arg Asn Trp Glu Glu Thr Lys Gln
545                 550                 555

<210> SEQ ID NO 7
<211> LENGTH: 542
<212> TYPE: PRT
```

<213> ORGANISM: Ipomoea tricolor

<400> SEQUENCE: 7

Met Ala Phe Gly Leu Ser Ser Leu Leu Gln Asn Ser Glu Leu Phe Thr
1               5                   10                  15

Ser Asp His Ala Ser Val Val Ser Met Asn Leu Phe Val Ala Leu Leu
            20                  25                  30

Cys Ala Cys Ile Val Leu Gly His Leu Leu Glu Glu Asn Arg Trp Val
        35                  40                  45

Asn Glu Ser Ile Thr Ala Leu Ile Ile Gly Leu Cys Thr Gly Val Val
    50                  55                  60

Ile Leu Leu Leu Ser Arg Gly Lys Ser Ser His Leu Leu Val Phe Ser
65                  70                  75                  80

Glu Asp Leu Phe Phe Ile Tyr Leu Leu Pro Pro Ile Ile Phe Asn Ala
                85                  90                  95

Gly Phe Gln Val Lys Lys Lys Gln Phe Phe Val Asn Phe Met Thr Ile
            100                 105                 110

Met Leu Phe Gly Ala Ile Gly Thr Leu Ile Ser Cys Ser Ile Ile Ser
        115                 120                 125

Phe Gly Ala Val Lys Ile Phe Lys His Leu Asp Ile Asp Phe Leu Asp
    130                 135                 140

Phe Gly Asp Tyr Leu Ala Ile Gly Ala Ile Phe Ala Ala Thr Asp Ser
145                 150                 155                 160

Val Cys Thr Leu Gln Val Leu Ser Gln Asp Glu Thr Pro Leu Leu Tyr
                165                 170                 175

Ser Leu Val Phe Gly Glu Gly Val Val Asn Asp Ala Thr Ser Val Val
            180                 185                 190

Leu Phe Asn Ala Ile Gln Ser Phe Asp Met Thr Ser Phe Asp Pro Lys
        195                 200                 205

Ile Gly Leu His Phe Ile Gly Asn Phe Leu Tyr Leu Phe Leu Ser Ser
    210                 215                 220

Thr Phe Leu Gly Val Gly Ile Gly Leu Leu Cys Ala Tyr Ile Ile Lys
225                 230                 235                 240

Lys Leu Tyr Phe Gly Arg His Ser Thr Asp Arg Glu Val Ala Leu Met
                245                 250                 255

Met Leu Met Ser Tyr Leu Ser Tyr Ile Met Ala Glu Leu Phe Tyr Leu
            260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Val Thr Thr Arg His Ser
    290                 295                 300

Phe Ala Thr Leu Ser Phe Val Ala Glu Thr Phe Ile Phe Leu Tyr Val
305                 310                 315                 320

Gly Met Asp Ala Leu Asp Ile Glu Lys Trp Lys Phe Val Lys Asn Ser
                325                 330                 335

Gln Gly Leu Ser Val Ala Val Ser Ser Ile Leu Val Gly Leu Ile Leu
            340                 345                 350

Val Gly Arg Ala Ala Phe Val Phe Pro Leu Ser Phe Leu Ser Asn Leu
        355                 360                 365

Ala Lys Lys Asn Ser Ser Asp Lys Ile Ser Phe Arg Gln Gln Ile Ile
    370                 375                 380

Ile Trp Trp Ala Gly Leu Met Arg Gly Ala Val Ser Ile Ala Leu Ala
385                 390                 395                 400

Tyr Asn Lys Phe Thr Thr Ser Gly His Thr Ser Leu His Glu Asn Ala

```
            405                 410                 415
Ile Met Ile Thr Ser Thr Val Thr Val Val Leu Phe Ser Thr Val Val
                420                 425                 430

Phe Gly Leu Met Thr Lys Pro Leu Ile Asn Leu Leu Leu Pro Pro His
            435                 440                 445

Lys Gln Ile Ala Ser Gly His Ser Ser Met Thr Thr Ser Glu Pro Ser
        450                 455                 460

Ser Pro Lys His Phe Ala Val Pro Leu Leu Asp Asn Gln His Asp Ser
465                 470                 475                 480

Glu Ser Asp Met Ile Thr Gly Pro Glu Val Ala Arg Pro Thr Ala Leu
                485                 490                 495

Arg Met Leu Leu Arg Thr Pro Thr His Thr Val His Arg Tyr Trp Arg
            500                 505                 510

Lys Phe Asp Asp Ser Phe Met Arg Pro Val Phe Gly Arg Gly Phe
        515                 520                 525

Val Pro Phe Val Ala Gly Ser Pro Ala Glu Gln Ser Pro Arg
530                 535                 540

<210> SEQ ID NO 8
<211> LENGTH: 575
<212> TYPE: PRT
<213> ORGANISM: Arabidopsis thaliana

<400> SEQUENCE: 8

Met Ile Ser Pro Val Glu His Asp Pro Gln Gly Gln Val Lys Gln Gln
1               5                   10                  15

Gln Ala Ala Gly Val Gly Ile Leu Leu Gln Ile Met Met Leu Val Leu
                20                  25                  30

Ser Phe Val Leu Gly His Val Leu Arg Arg His Arg Phe His Tyr Leu
            35                  40                  45

Pro Glu Ala Ser Gly Ser Leu Leu Ile Gly Leu Ile Val Gly Ile Leu
        50                  55                  60

Ala Asn Ile Ser Asp Thr Glu Thr Ser Ile Arg Phe Cys Pro Pro
65                  70                  75                  80

Ser Ile Pro Glu Phe Ser Leu Leu Ser Phe Pro Arg Ser Leu Val Cys
                85                  90                  95

Ser Phe Tyr Ser Val Ser Gly Arg Gly Leu Ile Ser Thr Lys Ser Ser
            100                 105                 110

Ser Ser Cys Phe Cys Cys Leu Pro Ser Tyr Tyr Ile Leu Cys Phe Asn
        115                 120                 125

Ile Cys Ile Ser Ser Phe Lys Phe Ala Ala Ala Met Leu Cys Ile Met
130                 135                 140

Asp Val Ile Phe Leu Asp Ile Ile His Leu Phe Glu Pro Ser Gln Val
145                 150                 155                 160

Ser Val Phe Asn Leu Asn His Ser Phe Leu Thr Leu Glu Pro Leu Leu
                165                 170                 175

Pro Leu Leu Ser Ser Glu Leu Leu Ser Leu Gln Leu Leu Val Val
            180                 185                 190

Cys Tyr Leu Gly Gly Ser Met Tyr Leu Met Tyr Lys Leu Pro Phe Val
        195                 200                 205

Glu Cys Leu Met Phe Gly Ala Leu Ile Ser Ala Thr Asp Pro Val Thr
    210                 215                 220

Val Leu Ser Ile Phe Gln Val Leu Leu Leu Phe Leu Leu Ser Val
225                 230                 235                 240

Ser Thr Gly Tyr Lys Tyr Ser His Asp Val Gly Thr Asp Val Asn Leu
```

```
                245                 250                 255
Tyr Ala Leu Val Phe Gly Glu Ser Val Leu Asn Asp Ala Val Ser Phe
            260                 265                 270

Tyr Tyr Leu Leu Arg Tyr Trp Ala Leu Pro Phe Lys Thr Met Ser Leu
        275                 280                 285

Val Asn Arg Gln Ser Ser Gly Glu His Phe Phe Met Val Val Ile
290                 295                 300

Arg Phe Phe Glu Thr Phe Ala Gly Ser Met Ser Ala Gly Leu Ala Ile
305                 310                 315                 320

Ser Phe Leu Asn Ser Phe Tyr Thr Val Val Phe Thr Leu Leu Ile Leu
            325                 330                 335

Ser Glu His Ile Val Asn Val Met Ser Leu Phe Ser Leu Phe Ser Thr
            340                 345                 350

Ser Ile His Ala Cys Arg Arg Cys Trp Ser Leu Arg His Cys Phe Tyr
            355                 360                 365

Thr Leu His Arg Asn Cys Asn Arg Arg Val Met Lys Arg Tyr Thr Phe
        370                 375                 380

Ser Asn Leu Ser Glu Ala Ser Gln Ser Phe Val Ser Ser Phe His
385                 390                 395                 400

Leu Ile Ser Ser Leu Ala Glu Thr Phe Thr Phe Ile Tyr Met Gly Phe
                405                 410                 415

Asp Ile Ala Met Glu Gln His Ser Trp Ser His Val Gly Ala Val Asn
            420                 425                 430

Val Phe Gly Cys Ala Tyr Leu Val Asn Leu Phe Arg Gln Glu Asn Gln
        435                 440                 445

Lys Ile Pro Met Lys His Gln Lys Ala Leu Trp Tyr Ser Gly Leu Arg
    450                 455                 460

Gly Ala Met Ala Phe Ala Leu Ala Leu Gln Ser Leu His Asp Leu Pro
465                 470                 475                 480

Glu Gly His Gly Gln Ile Ile Phe Thr Ala Thr Thr Ile Val Val
                485                 490                 495

Val Thr Val Thr Phe Val Leu Leu Ile Gly Gly Ser Thr Gly Lys Met
            500                 505                 510

Leu Glu Ala Leu Glu Val Val Gly Asp Asp Leu Asp Asp Ser Met Ser
        515                 520                 525

Glu Val Asn Ser Arg Arg Ser Thr Leu Ile Ser Leu Asn Ile Gly Ala
    530                 535                 540

Ser Ser Asp Glu Asp Thr Ser Ser Gly Ser Arg Phe Lys Met Lys
545                 550                 555                 560

Leu Lys Glu Phe His Lys Thr Gly Asp Gly Asp Gly Asp Gly Glu
                565                 570                 575

<210> SEQ ID NO 9
<211> LENGTH: 1146
<212> TYPE: PRT
<213> ORGANISM: Arabidopsis thaliana

<400> SEQUENCE: 9

Met Thr Thr Val Ile Asp Ala Thr Met Ala Tyr Arg Phe Leu Glu Glu
1               5                   10                  15

Ala Thr Asp Ser Ser Ser Ser Ser Ser Lys Leu Glu Ser Ser
            20                  25                  30

Pro Val Asp Ala Val Leu Phe Val Gly Met Ser Leu Val Leu Gly Ile
        35                  40                  45

Ala Ser Arg His Leu Leu Arg Gly Thr Arg Val Pro Tyr Thr Val Ala
```

-continued

```
            50                  55                  60
Leu Leu Val Ile Gly Ile Ala Leu Gly Ser Leu Glu Tyr Gly Ala Lys
65                  70                  75                  80

His Asn Leu Gly Lys Ile Gly His Gly Ile Arg Ile Trp Asn Glu Ile
                85                  90                  95

Asp Pro Glu Leu Leu Ala Val Phe Leu Pro Ala Leu Leu Phe Glu
            100                 105                 110

Ser Ser Phe Ser Met Glu Val His Gln Ile Lys Arg Cys Leu Gly Gln
            115                 120                 125

Met Val Leu Leu Ala Val Pro Gly Val Leu Ile Ser Thr Ala Cys Leu
    130                 135                 140

Gly Ser Leu Val Lys Val Thr Phe Pro Tyr Glu Trp Asp Trp Lys Thr
145                 150                 155                 160

Ser Leu Leu Leu Gly Gly Leu Leu Ser Ala Thr Asp Pro Val Ala Val
                165                 170                 175

Val Ala Leu Leu Lys Glu Leu Gly Ala Ser Lys Lys Leu Ser Thr Ile
            180                 185                 190

Ile Glu Gly Glu Ser Leu Met Asn Asp Gly Thr Ala Ile Val Val Phe
    195                 200                 205

Gln Leu Phe Leu Lys Met Ala Met Gly Gln Asn Ser Asp Trp Ser Ser
210                 215                 220

Ile Ile Lys Phe Leu Leu Lys Val Ala Leu Gly Ala Val Gly Ile Gly
225                 230                 235                 240

Leu Ala Phe Gly Ile Ala Ser Val Ile Trp Leu Lys Phe Ile Phe Asn
                245                 250                 255

Asp Thr Val Ile Glu Ile Thr Leu Thr Ile Ala Val Ser Tyr Phe Ala
            260                 265                 270

Tyr Tyr Thr Ala Gln Glu Trp Ala Gly Ala Ser Gly Val Leu Thr Val
    275                 280                 285

Met Thr Leu Gly Met Phe Tyr Ala Ala Phe Ala Arg Thr Ala Phe Lys
290                 295                 300

Gly Asp Ser Gln Lys Ser Leu His His Phe Trp Glu Met Val Ala Tyr
305                 310                 315                 320

Ile Ala Asn Thr Leu Ile Phe Ile Leu Ser Gly Val Val Ile Ala Glu
                325                 330                 335

Gly Ile Leu Asp Ser Asp Lys Ile Ala Tyr Gln Gly Asn Ser Trp Arg
            340                 345                 350

Phe Leu Phe Leu Leu Tyr Val Tyr Ile Gln Leu Ser Arg Val Val Val
    355                 360                 365

Val Gly Val Leu Tyr Pro Leu Leu Cys Arg Phe Gly Tyr Gly Leu Asp
370                 375                 380

Trp Lys Glu Ser Ile Ile Leu Val Trp Ser Gly Leu Arg Gly Ala Val
385                 390                 395                 400

Ala Leu Ala Leu Ser Leu Ser Val Lys Gln Ser Ser Gly Asn Ser His
                405                 410                 415

Ile Ser Lys Glu Thr Gly Thr Leu Phe Leu Phe Thr Gly Gly Ile
            420                 425                 430

Val Phe Leu Thr Leu Ile Val Asn Gly Ser Thr Thr Gln Phe Val Leu
    435                 440                 445

Arg Leu Leu Arg Met Asp Ile Leu Pro Ala Pro Lys Lys Arg Ile Leu
450                 455                 460

Glu Tyr Thr Lys Tyr Glu Met Leu Asn Lys Ala Leu Arg Ala Phe Gln
465                 470                 475                 480
```

```
Asp Leu Gly Asp Asp Glu Glu Leu Gly Pro Ala Asp Trp Pro Thr Val
            485                 490                 495
Glu Ser Tyr Ile Ser Ser Leu Lys Gly Ser Gly Glu Leu Val His
        500                 505                 510
His Pro His Asn Gly Ser Lys Ile Gly Ser Leu Asp Pro Lys Ser Leu
        515                 520                 525
Lys Asp Ile Arg Met Arg Phe Leu Asn Gly Val Gln Ala Thr Tyr Trp
    530                 535                 540
Glu Met Leu Asp Glu Gly Arg Ile Ser Glu Val Thr Ala Asn Ile Leu
545                 550                 555                 560
Met Gln Ser Val Asp Glu Ala Leu Asp Gln Val Ser Thr Thr Leu Cys
                565                 570                 575
Asp Trp Arg Gly Leu Lys Pro His Val Asn Phe Pro Asn Tyr Tyr Asn
            580                 585                 590
Phe Leu His Ser Lys Val Val Pro Arg Lys Leu Val Thr Tyr Phe Ala
        595                 600                 605
Val Glu Arg Leu Glu Ser Ala Cys Tyr Ile Ser Ala Ala Phe Leu Arg
    610                 615                 620
Ala His Thr Ile Ala Arg Gln Gln Leu Tyr Asp Phe Leu Gly Glu Ser
625                 630                 635                 640
Asn Ile Gly Ser Ile Val Ile Asn Glu Ser Glu Lys Glu Gly Glu Glu
                645                 650                 655
Ala Lys Lys Phe Leu Glu Lys Val Arg Ser Ser Phe Pro Gln Val Leu
            660                 665                 670
Arg Val Val Lys Thr Lys Gln Val Thr Tyr Ser Val Leu Asn His Leu
        675                 680                 685
Leu Gly Tyr Ile Glu Asn Leu Glu Lys Val Gly Leu Leu Glu Glu Lys
    690                 695                 700
Glu Ile Ala His Leu His Asp Ala Val Gln Thr Gly Leu Lys Lys Leu
705                 710                 715                 720
Leu Arg Asn Pro Pro Ile Val Lys Leu Pro Lys Leu Ser Asp Met Ile
                725                 730                 735
Thr Ser His Pro Leu Ser Val Ala Leu Pro Pro Ala Phe Cys Glu Pro
            740                 745                 750
Leu Lys His Ser Lys Lys Glu Pro Met Lys Leu Arg Gly Val Thr Leu
        755                 760                 765
Tyr Lys Glu Gly Ser Lys Pro Thr Gly Val Trp Leu Ile Phe Asp Gly
    770                 775                 780
Ile Val Lys Trp Lys Ser Lys Ile Leu Ser Asn His Ser Leu His
785                 790                 795                 800
Pro Thr Phe Ser His Gly Ser Thr Leu Gly Leu Tyr Glu Val Leu Thr
                805                 810                 815
Gly Lys Pro Tyr Leu Cys Asp Leu Ile Thr Asp Ser Met Val Leu Cys
            820                 825                 830
Phe Phe Ile Asp Ser Glu Lys Ile Leu Ser Leu Gln Ser Asp Ser Thr
        835                 840                 845
Ile Asp Asp Phe Leu Trp Gln Glu Ser Ala Leu Val Leu Leu Lys Leu
    850                 855                 860
Leu Arg Pro Gln Ile Phe Glu Ser Val Ala Met Gln Glu Leu Arg Ala
865                 870                 875                 880
Leu Val Ser Thr Glu Ser Ser Lys Leu Thr Thr Tyr Val Thr Gly Glu
                885                 890                 895
Ser Ile Glu Ile Asp Cys Asn Ser Ile Gly Leu Leu Leu Glu Gly Phe
            900                 905                 910
```

Val Lys Pro Val Gly Ile Lys Glu Glu Leu Ile Ser Ser Pro Ala Ala
            915                 920                 925

Leu Ser Pro Ser Asn Gly Asn Gln Ser Phe His Asn Ser Ser Glu Ala
        930                 935                 940

Ser Gly Ile Met Arg Val Ser Phe Ser Gln Ala Thr Gln Tyr Ile
945                 950                 955                 960

Val Glu Thr Arg Ala Arg Ala Ile Ile Phe Asn Ile Gly Ala Phe Gly
                965                 970                 975

Ala Asp Arg Thr Leu His Arg Arg Pro Ser Ser Leu Thr Pro Pro Arg
            980                 985                 990

Ser Ser Ser Ser Asp Gln Leu Gln Arg Ser Phe Arg Lys Glu His Arg
        995                 1000                1005

Gly Leu Met Ser Trp Pro Glu Asn Ile Tyr Ala Lys Gln Gln Gln Glu
    1010                1015                1020

Ile Asn Lys Thr Thr Leu Ser Leu Ser Glu Arg Ala Met Gln Leu Ser
1025                1030                1035                1040

Ile Phe Gly Ser Met Val Asn Val Tyr Arg Arg Ser Val Ser Phe Gly
                1045                1050                1055

Gly Ile Tyr Asn Asn Lys Leu Gln Asp Asn Leu Leu Tyr Lys Lys Leu
            1060                1065                1070

Pro Leu Asn Pro Ala Gln Gly Leu Val Ser Ala Lys Ser Glu Ser Ser
        1075                1080                1085

Ile Val Thr Lys Lys Gln Leu Glu Thr Arg Lys His Ala Cys Gln Leu
    1090                1095                1100

Pro Leu Lys Gly Glu Ser Ser Thr Arg Gln Asn Thr Met Val Glu Ser
1105                1110                1115                1120

Ser Asp Glu Glu Asp Glu Asp Glu Gly Ile Val Val Arg Ile Asp Ser
                1125                1130                1135

Pro Ser Lys Ile Val Phe Arg Asn Asp Leu
            1140                1145

<210> SEQ ID NO 10
<211> LENGTH: 555
<212> TYPE: PRT
<213> ORGANISM: Atriplex gmelini

<400> SEQUENCE: 10

Met Trp Ser Gln Leu Ser Ser Leu Leu Ser Gly Lys Met Asp Ala Leu
1               5                   10                  15

Thr Thr Ser Asp His Ala Ser Val Val Ser Met Asn Leu Phe Val Ala
            20                  25                  30

Leu Leu Cys Gly Cys Ile Val Ile Gly His Leu Leu Glu Glu Asn Arg
        35                  40                  45

Trp Met Asn Glu Ser Ile Thr Ala Leu Leu Ile Gly Leu Ala Thr Gly
    50                  55                  60

Val Val Ile Leu Leu Ile Ser Gly Gly Lys Ser Ser His Leu Leu Val
65                  70                  75                  80

Phe Ser Glu Asp Leu Phe Phe Ile Tyr Leu Leu Pro Pro Ile Ile Phe
                85                  90                  95

Asn Ala Gly Phe Gln Val Lys Lys Lys Gln Phe Phe Arg Asn Phe Ile
            100                 105                 110

Thr Ile Val Leu Phe Gly Ala Val Gly Thr Leu Val Ser Phe Thr Ile
        115                 120                 125

Ile Ser Leu Gly Ala Leu Ser Ile Phe Lys Lys Leu Asp Ile Gly Thr
    130                 135                 140

```
Leu Glu Leu Ala Asp Tyr Leu Ala Ile Gly Ala Ile Phe Ala Ala Thr
145                 150                 155                 160

Asp Ser Val Cys Thr Leu Gln Val Leu Asn Gln Asp Glu Thr Pro Leu
                165                 170                 175

Leu Tyr Ser Leu Val Phe Gly Glu Gly Val Val Asn Asp Ala Thr Ser
            180                 185                 190

Val Val Leu Phe Asn Ala Ile Gln Ser Phe Asp Leu Thr Arg Ile Asp
        195                 200                 205

His Arg Ile Ala Leu Gln Phe Met Gly Asn Phe Leu Tyr Leu Phe Ile
    210                 215                 220

Ala Ser Thr Ile Leu Gly Ala Phe Thr Gly Leu Leu Ser Ala Tyr Ile
225                 230                 235                 240

Ile Lys Lys Leu Tyr Phe Gly Arg His Ser Thr Asp Arg Glu Val Ala
                245                 250                 255

Leu Met Met Leu Met Ala Tyr Leu Ser Tyr Met Leu Ala Glu Leu Phe
            260                 265                 270

Tyr Leu Ser Gly Ile Leu Thr Val Phe Phe Cys Gly Ile Val Met Ser
        275                 280                 285

His Tyr Thr Trp His Asn Val Thr Glu Ser Ser Arg Val Thr Thr Lys
    290                 295                 300

His Ala Phe Ala Thr Leu Ser Phe Val Ala Glu Val Phe Leu Phe Leu
305                 310                 315                 320

Tyr Val Gly Met Asp Ala Leu Asp Ile Glu Lys Trp Arg Phe Val Ser
                325                 330                 335

Asp Ser Pro Gly Ile Ser Val Ala Val Ser Ser Ile Leu Leu Gly Leu
            340                 345                 350

Val Met Val Gly Arg Ala Ala Phe Val Phe Pro Leu Ser Trp Leu Met
        355                 360                 365

Asn Phe Ala Lys Lys Ser Gln Ser Glu Lys Val Thr Phe Asn Gln Gln
    370                 375                 380

Ile Val Ile Trp Trp Ala Gly Leu Met Arg Gly Ala Val Ser Met Ala
385                 390                 395                 400

Leu Ala Tyr Asn Gln Phe Thr Arg Ser Gly His Thr Gln Leu Arg Gly
                405                 410                 415

Asn Ala Ile Met Ile Thr Ser Thr Ile Ser Val Val Leu Phe Ser Thr
            420                 425                 430

Met Val Phe Gly Leu Leu Thr Lys Pro Leu Ile Met Phe Leu Leu Pro
        435                 440                 445

Gln Pro Lys His Phe Thr Ser Cys Ser Thr Val Ser Asp Val Gly Ser
    450                 455                 460

Pro Lys Ser Tyr Ser Leu Pro Leu Leu Glu Gly Asn Gln Asp Tyr Glu
465                 470                 475                 480

Val Asp Val Gly Asn Gly Asn His Glu Asp Thr Thr Glu Pro Arg Thr
                485                 490                 495

Ile Val Arg Pro Ser Ser Leu Arg Met Leu Leu Asn Ala Pro Thr His
            500                 505                 510

Thr Val His His Tyr Trp Arg Lys Phe Asp Asp Ser Phe Met Arg Pro
        515                 520                 525

Val Phe Gly Gly Arg Gly Phe Val Pro Phe Val Pro Gly Ser Pro Thr
    530                 535                 540

Glu Gln Ser Thr Asn Asn Leu Val Asp Arg Thr
545                 550                 555
```

-continued

```
<210> SEQ ID NO 11
<211> LENGTH: 985
<212> TYPE: PRT
<213> ORGANISM: Saccharomyces cerevisiae

<400> SEQUENCE: 11

Met Ala Ile Trp Glu Gln Leu Glu Val Ser Lys Ala His Val Ala Tyr
 1               5                  10                  15

Ala Cys Val Gly Val Phe Ser Ser Ile Phe Ser Leu Val Ser Leu Tyr
            20                  25                  30

Val Lys Glu Lys Leu Tyr Ile Gly Glu Ser Thr Val Ala Gly Ile Phe
        35                  40                  45

Gly Leu Ile Val Gly Pro Val Cys Leu Asn Trp Phe Asn Pro Leu Lys
    50                  55                  60

Trp Gly Asn Ser Asp Ser Ile Thr Leu Glu Ile Thr Arg Ile Val Leu
65                  70                  75                  80

Cys Leu Gln Ile Phe Ala Val Ala Val Glu Leu Pro Arg Lys Tyr Met
                85                  90                  95

Leu Lys His Trp Val Ser Val Thr Met Leu Leu Pro Val Met Thr
            100                 105                 110

Ala Gly Trp Leu Ile Ile Gly Leu Phe Val Trp Ile Leu Ile Pro Gly
        115                 120                 125

Leu Asn Phe Ser Ala Ser Leu Leu Ile Ser Ala Cys Ile Thr Ala Thr
    130                 135                 140

Asp Pro Ile Leu Ala Gln Ser Val Val Ser Gly Lys Phe Ala Gln Arg
145                 150                 155                 160

Val Pro Gly His Leu Arg Asn Leu Leu Ser Ala Glu Ser Gly Cys Asn
                165                 170                 175

Asp Gly Met Ala Phe Pro Phe Leu Phe Leu Ser Met Asn Leu Ile Leu
            180                 185                 190

His Pro Gly Asn Gly Arg Glu Ile Val Lys Asp Trp Ile Cys Val Thr
        195                 200                 205

Ile Leu Tyr Glu Cys Leu Phe Gly Cys Leu Leu Gly Cys Phe Ile Gly
    210                 215                 220

Tyr Val Gly Arg Ile Thr Ile Arg Phe Ala Glu Lys Lys Asn Ile Ile
225                 230                 235                 240

Asp Arg Glu Ser Phe Leu Ala Phe Tyr Val Val Leu Ala Phe Met Cys
                245                 250                 255

Ala Gly Phe Gly Ser Ile Leu Gly Val Asp Asp Leu Leu Val Ser Phe
            260                 265                 270

Ala Ala Gly Ala Thr Phe Ala Trp Asp Gly Trp Phe Ser Gln Lys Thr
        275                 280                 285

Gln Glu Ser Asn Val Ser Thr Val Ile Asp Leu Leu Asn Tyr Ala
    290                 295                 300

Tyr Phe Ile Tyr Phe Gly Ala Ile Ile Pro Trp Ser Gln Phe Asn Asn
305                 310                 315                 320

Gly Glu Ile Gly Thr Asn Val Trp Arg Leu Ile Ile Leu Ser Ile Val
                325                 330                 335

Val Ile Phe Leu Arg Arg Ile Pro Ala Val Met Ile Leu Arg Pro Leu
            340                 345                 350

Ile Pro Asp Ile Lys Ser Trp Arg Glu Ala Leu Phe Val Gly His Phe
        355                 360                 365

Gly Pro Ile Gly Val Gly Ala Ile Phe Ala Ala Ile Leu Ala Arg Gly
    370                 375                 380

Glu Leu Glu Ser Thr Phe Ser Asp Glu Pro Thr Pro Leu Asn Val Val
```

```
                385                 390                 395                 400

Pro Ser Lys Glu Glu Ser Lys His Trp Gln Leu Ile Ala Cys Ile Trp
                        405                 410                 415

Pro Ile Thr Cys Phe Phe Ile Val Thr Ser Ile Ile Val His Gly Ser
                        420                 425                 430

Ser Val Ala Ile Ile Thr Leu Gly Arg His Leu Asn Thr Ile Thr Leu
                        435                 440                 445

Thr Lys Thr Phe Thr Thr His Thr Thr Asn Gly Asp Asn Gly Lys Ser
                450                 455                 460

Ser Trp Met Gln Arg Leu Pro Ser Leu Asp Lys Ala Gly Arg Ser Phe
        465                 470                 475                 480

Ser Leu His Arg Met Asp Thr Gln Met Thr Leu Ser Gly Asp Glu Gly
                        485                 490                 495

Glu Ala Glu Glu Gly Gly Gly Arg Lys Gly Leu Ala Gly Glu Glu Asp
                        500                 505                 510

Glu Glu Gly Leu Asn Asn Asp Gln Ile Gly Ser Val Ala Thr Ser Gly
                        515                 520                 525

Ile Pro Ala Arg Pro Ala Gly Gly Met Pro Arg Arg Arg Lys Leu Ser
        530                 535                 540

Arg Lys Glu Lys Arg Leu Asn Arg Arg Gln Lys Leu Arg Asn Lys Gly
        545                 550                 555                 560

Arg Glu Ile Phe Ser Ser Arg Ser Lys Asn Glu Met Tyr Asp Asp Asp
                        565                 570                 575

Glu Leu Asn Asp Leu Gly Arg Glu Arg Leu Gln Lys Glu Lys Glu Ala
                        580                 585                 590

Arg Ala Ala Thr Phe Ala Leu Ser Thr Ala Val Asn Thr Gln Arg Asn
                        595                 600                 605

Glu Glu Ile Gly Met Gly Gly Asp Glu Glu Asp Glu Tyr Thr Pro
                        610                 615                 620

Glu Lys Glu Tyr Ser Asp Asn Tyr Asn Asn Thr Pro Ser Phe Glu Ser
        625                 630                 635                 640

Ser Glu Arg Ser Ser Ser Leu Arg Gly Arg Thr Tyr Val Pro Arg Asn
                        645                 650                 655

Arg Tyr Asp Gly Glu Glu Thr Glu Ser Glu Ile Glu Ser Glu Asp Glu
                        660                 665                 670

Met Glu Asn Glu Ser Glu Arg Ser Met Ala Ser Ser Glu Arg Arg
                        675                 680                 685

Ile Arg Lys Met Lys Glu Glu Met Lys Pro Gly Thr Ala Tyr Leu
        690                 695                 700

Asp Gly Asn Arg Met Ile Ile Glu Asn Lys Gln Gly Glu Ile Leu Asn
        705                 710                 715                 720

Gln Val Asp Ile Glu Asp Arg Asn Glu Ala Arg Asp Glu Val Ser
                        725                 730                 735

Val Asp Ser Thr Ala His Ser Ser Leu Thr Thr Thr Met Thr Asn Leu
                        740                 745                 750

Ser Ser Ser Ser Gly Gly Arg Leu Lys Arg Ile Leu Thr Pro Thr Ser
                        755                 760                 765

Leu Gly Lys Ile His Ser Leu Val Asp Lys Gly Lys Asp Lys Asn Lys
                        770                 775                 780

Asn Ser Lys Tyr His Ala Phe Lys Ile Asp Asn Leu Leu Ile Ile Glu
        785                 790                 795                 800

Asn Glu Asp Gly Asp Val Ile Lys Arg Tyr Lys Ile Asn Pro His Lys
                        805                 810                 815
```

Ser Asp Asp Asp Lys Ser Lys Asn Arg Pro Arg Asn Asp Ser Val Val
            820                 825                 830

Ser Arg Ala Leu Thr Ala Val Gly Leu Lys Ser Lys Ala Asn Ser Gly
        835                 840                 845

Val Pro Pro Val Asp Glu Glu Lys Ala Ile Glu Gly Pro Ser Arg
    850                 855                 860

Lys Gly Pro Gly Met Leu Lys Lys Arg Thr Leu Thr Pro Ala Pro Pro
865                 870                 875                 880

Arg Gly Val Gln Asp Ser Leu Asp Leu Glu Asp Pro Ser Ser Glu
                885                 890                 895

Glu Asp Leu Gly Asp Ser Tyr Asn Met Asp Asp Ser Gly Asp Tyr Asp
            900                 905                 910

Asp Asn Ala Tyr Glu Ser Glu Thr Glu Phe Glu Arg Gln Arg Arg Leu
            915                 920                 925

Asn Ala Leu Gly Glu Met Thr Ala Pro Ala Asp Gln Asp Asp Glu Glu
            930                 935                 940

Leu Pro Pro Leu Pro Val Glu Ala Gln Thr Gly Asn Asp Gly Pro Gly
945                 950                 955                 960

Thr Ala Glu Gly Lys Lys Lys Gln Lys Ser Ala Ala Val Lys Ser Ala
                965                 970                 975

Leu Ser Lys Thr Leu Gly Leu Asn Lys
            980                 985

<210> SEQ ID NO 12
<211> LENGTH: 633
<212> TYPE: PRT
<213> ORGANISM: Saccharomyces cerevisiae

<400> SEQUENCE: 12

Met Leu Ser Lys Val Leu Leu Asn Ile Ala Phe Lys Val Leu Leu Thr
1               5                   10                  15

Thr Ala Lys Arg Ala Val Asp Pro Asp Asp Asp Glu Leu Leu Pro
            20                  25                  30

Ser Pro Asp Leu Pro Gly Ser Asp Asp Pro Ile Ala Gly Asp Pro Asp
        35                  40                  45

Val Asp Leu Asn Pro Val Thr Glu Glu Met Phe Ser Ser Trp Ala Leu
 50                 55                  60

Phe Ile Met Leu Leu Leu Ile Ser Ala Leu Trp Ser Ser Tyr Tyr
65                  70                  75                  80

Leu Thr Gln Lys Arg Ile Arg Ala Val His Glu Thr Val Leu Ser Ile
                85                  90                  95

Phe Tyr Gly Met Val Ile Gly Leu Ile Ile Arg Met Ser Pro Gly His
            100                 105                 110

Tyr Ile Gln Asp Thr Val Thr Phe Asn Ser Ser Tyr Phe Phe Asn Val
        115                 120                 125

Leu Leu Pro Pro Ile Ile Leu Asn Ser Gly Tyr Glu Leu Asn Gln Val
    130                 135                 140

Asn Phe Phe Asn Asn Met Leu Ser Ile Leu Ile Phe Ala Ile Pro Gly
145                 150                 155                 160

Thr Phe Ile Ser Ala Val Val Ile Gly Ile Ile Leu Tyr Ile Trp Thr
                165                 170                 175

Phe Leu Gly Leu Glu Ser Ile Asp Ile Ser Phe Ala Asp Ala Met Ser
            180                 185                 190

Val Gly Ala Thr Leu Ser Ala Thr Asp Pro Val Thr Ile Leu Ser Ile
        195                 200                 205

-continued

Phe Asn Ala Tyr Lys Val Asp Pro Lys Leu Tyr Thr Ile Ile Phe Gly
210                 215                 220

Glu Ser Leu Leu Asn Asp Ala Ile Ser Ile Val Met Phe Glu Thr Cys
225                 230                 235                 240

Gln Lys Phe His Gly Gln Pro Ala Thr Phe Ser Ser Val Phe Glu Gly
                245                 250                 255

Ala Gly Leu Phe Leu Met Thr Phe Ser Val Ser Leu Leu Ile Gly Val
            260                 265                 270

Leu Ile Gly Ile Leu Val Ala Leu Leu Leu Lys His Thr His Ile Arg
        275                 280                 285

Arg Tyr Pro Gln Ile Glu Ser Cys Leu Ile Leu Ile Ala Tyr Glu
290                 295                 300

Ser Tyr Phe Phe Ser Asn Gly Cys His Met Ser Gly Ile Val Ser Leu
305                 310                 315                 320

Leu Phe Cys Gly Ile Thr Leu Lys His Tyr Ala Tyr Asn Met Ser
                325                 330                 335

Arg Arg Ser Gln Ile Thr Ile Lys Tyr Ile Phe Gln Leu Leu Ala Arg
                340                 345                 350

Leu Ser Glu Asn Phe Ile Phe Ile Tyr Leu Gly Leu Glu Leu Phe Thr
            355                 360                 365

Glu Val Glu Leu Val Tyr Lys Pro Leu Leu Ile Ile Val Ala Ala Ile
370                 375                 380

Ser Ile Cys Val Ala Arg Trp Cys Ala Val Phe Pro Leu Ser Gln Phe
385                 390                 395                 400

Val Asn Trp Ile Tyr Arg Val Lys Thr Ile Arg Ser Met Ser Gly Ile
                405                 410                 415

Thr Gly Glu Asn Ile Ser Val Pro Asp Glu Ile Pro Tyr Asn Tyr Gln
            420                 425                 430

Met Met Thr Phe Trp Ala Gly Leu Arg Gly Ala Val Gly Val Ala Leu
            435                 440                 445

Ala Leu Gly Ile Gln Gly Glu Tyr Lys Phe Thr Leu Leu Ala Thr Val
        450                 455                 460

Leu Val Val Val Leu Thr Val Ile Ile Phe Gly Gly Thr Thr Ala
465                 470                 475                 480

Gly Met Leu Glu Val Leu Asn Ile Lys Thr Gly Cys Ile Ser Glu Glu
                485                 490                 495

Asp Thr Ser Asp Asp Glu Phe Asp Ile Glu Ala Pro Arg Ala Ile Asn
            500                 505                 510

Leu Leu Asn Gly Ser Ser Ile Gln Thr Asp Leu Gly Pro Tyr Ser Asp
        515                 520                 525

Asn Asn Ser Pro Asp Ile Ser Ile Asp Gln Phe Ala Val Ser Ser Asn
530                 535                 540

Lys Asn Leu Pro Asn Asn Ile Ser Thr Thr Gly Gly Asn Thr Phe Gly
545                 550                 555                 560

Gly Leu Asn Glu Thr Glu Asn Thr Ser Pro Asn Pro Ala Arg Ser Ser
                565                 570                 575

Met Asp Lys Arg Asn Leu Arg Asp Lys Leu Gly Thr Ile Phe Asn Ser
            580                 585                 590

Asp Ser Gln Trp Phe Gln Asn Phe Asp Glu Gln Val Leu Lys Pro Val
        595                 600                 605

Phe Leu Asp Asn Val Ser Pro Ser Leu Gln Asp Ser Ala Thr Gln Ser
610                 615                 620

Pro Ala Asp Phe Ser Ser Gln Asn His
625                 630

<210> SEQ ID NO 13
<211> LENGTH: 546
<212> TYPE: PRT
<213> ORGANISM: Arabidopsis thaliana

<400> SEQUENCE: 13

Met Thr Met Phe Ala Ser Leu Thr Ser Lys Met Leu Ser Val Ser Thr
1               5                   10                  15

Ser Asp His Ala Ser Val Val Ser Leu Asn Leu Phe Val Ala Leu Leu
            20                  25                  30

Cys Ala Cys Ile Val Ile Gly His Leu Glu Glu Asn Arg Trp Met
        35                  40                  45

Asn Glu Ser Ile Thr Ala Leu Leu Ile Gly Leu Gly Thr Gly Val Val
50                  55                  60

Ile Leu Leu Ile Ser Arg Gly Lys Asn Ser His Leu Leu Val Phe Ser
65                  70                  75                  80

Glu Asp Leu Phe Phe Ile Tyr Leu Leu Pro Pro Ile Ile Phe Asn Ala
                85                  90                  95

Gly Phe Gln Val Lys Lys Lys Gln Phe Phe Arg Asn Phe Val Thr Ile
            100                 105                 110

Met Ala Phe Gly Ala Ile Gly Thr Val Val Ser Cys Thr Ile Ile Ser
        115                 120                 125

Leu Gly Ala Ile Gln Phe Phe Lys Lys Leu Asp Ile Gly Thr Phe Asp
    130                 135                 140

Leu Gly Asp Phe Leu Ala Ile Gly Ala Ile Phe Ala Ala Thr Asp Ser
145                 150                 155                 160

Val Cys Thr Leu Gln Val Leu Asn Gln Asp Glu Thr Pro Leu Leu Tyr
                165                 170                 175

Ser Leu Val Phe Gly Glu Gly Val Val Asn Asp Ala Thr Ser Val Val
            180                 185                 190

Leu Phe Asn Ala Ile Gln Ser Phe Asp Leu Thr His Leu Asn His Glu
        195                 200                 205

Ala Ala Phe Gln Phe Leu Gly Asn Phe Phe Tyr Leu Phe Leu Leu Ser
    210                 215                 220

Thr Gly Leu Gly Val Ala Thr Gly Leu Ile Ser Ala Tyr Val Ile Lys
225                 230                 235                 240

Lys Leu Tyr Phe Gly Arg His Ser Thr Asp Arg Glu Val Ala Leu Met
                245                 250                 255

Met Leu Met Ala Tyr Leu Ser Tyr Met Leu Ala Glu Leu Phe Ala Leu
            260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Ile Thr Thr Lys His Ala
    290                 295                 300

Phe Ala Thr Leu Ser Phe Leu Ala Glu Thr Phe Ile Phe Leu Tyr Val
305                 310                 315                 320

Gly Met Asp Ala Leu Asp Ile Glu Lys Trp Arg Phe Val Ser Asp Ser
                325                 330                 335

Pro Gly Thr Ser Val Ala Val Ser Ser Ile Leu Met Gly Leu Val Met
            340                 345                 350

Leu Gly Arg Ala Ala Phe Val Phe Pro Leu Ser Phe Leu Ser Asn Leu
        355                 360                 365

Ala Lys Lys His Gln Ser Glu Lys Ile Ser Ile Lys Gln Gln Val Val
    370                 375                 380

```
Ile Trp Trp Ala Gly Leu Met Arg Gly Ala Val Ser Met Ala Leu Ala
385                 390                 395                 400

Tyr Asn Lys Phe Thr Arg Ser Gly His Thr Glu Leu Arg Gly Asn Ala
            405                 410                 415

Ile Met Ile Thr Ser Thr Ile Thr Val Cys Leu Phe Ser Thr Met Val
            420                 425                 430

Phe Gly Met Leu Thr Lys Pro Leu Ile Arg Tyr Leu Met Pro His Gln
            435                 440                 445

Lys Ala Thr Thr Ser Thr Thr Ser Met Leu Ser Asp Asp Ser Thr Pro
            450                 455                 460

Lys Ser Ile His Ile Pro Leu Leu Asp Gly Glu Gln Leu Asp Ser Phe
465                 470                 475                 480

Glu Leu Pro Gly Ser His Gln Asp Val Pro Arg Pro Asn Ser Leu Arg
                485                 490                 495

Gly Phe Leu Met Arg Pro Thr Arg Thr Val His Tyr Tyr Trp Arg Gln
                500                 505                 510

Phe Asp Asp Ala Phe Met Arg Pro Val Phe Gly Gly Arg Gly Phe Val
            515                 520                 525

Pro Phe Val Pro Gly Ser Pro Thr Glu Arg Ser Ser His Asp Leu Ser
            530                 535                 540

Lys Pro
545

<210> SEQ ID NO 14
<211> LENGTH: 529
<212> TYPE: PRT
<213> ORGANISM: Arabidopsis thaliana

<400> SEQUENCE: 14

Met Ser Ile Gly Leu Thr Glu Phe Val Thr Asn Lys Leu Ala Ala Glu
1               5                   10                  15

His Pro Gln Val Ile Pro Ile Ser Val Phe Ile Ala Ile Leu Cys Leu
            20                  25                  30

Cys Leu Val Ile Gly His Leu Leu Glu Glu Asn Arg Trp Val Asn Glu
            35                  40                  45

Ser Ile Thr Ala Ile Leu Val Gly Ala Ala Ser Gly Thr Val Ile Leu
50                  55                  60

Leu Ile Ser Lys Gly Lys Ser Ser His Ile Leu Val Phe Asp Glu Glu
65                  70                  75                  80

Leu Phe Phe Ile Tyr Leu Leu Pro Pro Ile Ile Phe Asn Ala Gly Phe
            85                  90                  95

Gln Val Lys Lys Lys Lys Phe Phe His Asn Phe Leu Thr Ile Met Ser
            100                 105                 110

Phe Gly Val Ile Gly Val Phe Ile Ser Thr Val Ile Ile Ser Phe Gly
            115                 120                 125

Thr Trp Trp Leu Phe Pro Lys Leu Gly Phe Lys Gly Leu Ser Ala Arg
            130                 135                 140

Asp Tyr Leu Ala Ile Gly Thr Ile Phe Ser Ser Thr Asp Thr Val Cys
145                 150                 155                 160

Thr Leu Gln Ile Leu His Gln Asp Glu Thr Pro Leu Leu Tyr Ser Leu
            165                 170                 175

Val Phe Gly Glu Gly Val Val Asn Asp Ala Thr Ser Val Val Leu Phe
            180                 185                 190

Asn Ala Val Gln Lys Ile Gln Phe Glu Ser Leu Thr Gly Trp Thr Ala
            195                 200                 205
```

```
Leu Gln Val Phe Gly Asn Phe Leu Tyr Leu Phe Ser Thr Ser Thr Leu
    210                 215                 220
Leu Gly Ile Gly Val Gly Leu Ile Thr Ser Phe Val Leu Lys Thr Leu
225                 230                 235                 240
Tyr Phe Gly Arg His Ser Thr Thr Arg Glu Leu Ala Ile Met Val Leu
                245                 250                 255
Met Ala Tyr Leu Ser Tyr Met Leu Ala Glu Leu Phe Ser Leu Ser Gly
            260                 265                 270
Ile Leu Thr Val Phe Phe Cys Gly Val Leu Met Ser His Tyr Ala Ser
        275                 280                 285
Tyr Asn Val Thr Glu Ser Ser Arg Ile Thr Ser Arg His Val Phe Ala
    290                 295                 300
Met Leu Ser Phe Ile Ala Glu Thr Phe Ile Phe Leu Tyr Val Gly Thr
305                 310                 315                 320
Asp Ala Leu Asp Phe Thr Lys Trp Lys Thr Ser Ser Leu Ser Phe Gly
                325                 330                 335
Gly Thr Leu Gly Val Ser Gly Val Ile Thr Ala Leu Val Leu Leu Gly
            340                 345                 350
Arg Ala Ala Phe Val Phe Pro Leu Ser Val Leu Thr Asn Phe Met Asn
        355                 360                 365
Arg His Thr Glu Arg Asn Glu Ser Ile Thr Phe Lys His Gln Val Ile
    370                 375                 380
Ile Trp Trp Ala Gly Leu Met Arg Gly Ala Val Ser Ile Ala Leu Ala
385                 390                 395                 400
Phe Lys Gln Phe Thr Tyr Ser Gly Val Thr Leu Asp Pro Val Asn Ala
                405                 410                 415
Ala Met Val Thr Asn Thr Thr Ile Val Val Leu Phe Thr Thr Leu Val
            420                 425                 430
Phe Gly Phe Leu Thr Lys Pro Leu Val Asn Tyr Leu Leu Pro Gln Asp
        435                 440                 445
Ala Ser His Asn Thr Gly Asn Arg Gly Lys Arg Thr Glu Pro Gly Ser
    450                 455                 460
Pro Lys Glu Asp Ala Thr Leu Pro Leu Leu Ser Phe Asp Glu Ser Ala
465                 470                 475                 480
Ser Thr Asn Phe Asn Arg Ala Lys Asp Ser Ile Ser Leu Leu Met Glu
                485                 490                 495
Gln Pro Val Tyr Thr Ile His Arg Tyr Trp Arg Lys Phe Asp Asp Thr
            500                 505                 510
Tyr Met Arg Pro Ile Phe Gly Gly Pro Arg Arg Glu Asn Gln Pro Glu
        515                 520                 525
Cys

<210> SEQ ID NO 15
<211> LENGTH: 552
<212> TYPE: PRT
<213> ORGANISM: Arabidopsis thaliana

<400> SEQUENCE: 15

Met Val Ile Gly Leu Ser Thr Met Leu Glu Lys Thr Glu Ala Leu Phe
1               5                   10                  15
Ala Ser Asp His Ala Ser Val Val Ser Met Asn Leu Phe Val Ala Leu
                20                  25                  30
Leu Cys Ala Cys Ile Val Leu Gly His Leu Leu Glu Glu Thr Arg Trp
        35                  40                  45
```

```
Met Asn Glu Ser Ile Thr Ala Leu Ile Ile Gly Ser Cys Thr Gly Ile
 50                  55                  60

Val Ile Leu Leu Ile Ser Gly Gly Lys Ser Ser Arg Ile Leu Val Phe
 65                  70                  75                  80

Ser Glu Asp Leu Phe Phe Ile Tyr Leu Leu Pro Pro Ile Ile Phe Asn
                 85                  90                  95

Ala Gly Phe Gln Val Lys Lys Gln Phe Phe Arg Asn Phe Met Thr
            100                 105                 110

Ile Met Leu Phe Gly Ala Ile Gly Thr Leu Ile Ser Phe Val Ile Ile
        115                 120                 125

Ser Phe Gly Ala Lys His Leu Phe Glu Lys Met Asn Ile Gly Asp Leu
130                 135                 140

Thr Ile Ala Asp Tyr Leu Ala Ile Gly Ala Ile Phe Ser Ala Thr Asp
145                 150                 155                 160

Ser Val Cys Thr Leu Gln Val Leu Asn Gln Asp Glu Thr Pro Leu Leu
                165                 170                 175

Tyr Ser Leu Val Phe Gly Glu Gly Val Val Asn Asp Ala Thr Ser Val
                180                 185                 190

Val Leu Phe Asn Ala Ile Gln Arg Phe Asp Leu Thr Asn Ile Asn Ser
            195                 200                 205

Ala Ile Ala Leu Glu Phe Ala Gly Asn Phe Phe Tyr Leu Phe Ile Leu
        210                 215                 220

Ser Thr Ala Leu Gly Val Ala Ala Gly Leu Leu Ser Ala Phe Val Ile
225                 230                 235                 240

Lys Lys Leu Tyr Ile Gly Arg His Ser Thr Asp Arg Glu Val Ala Leu
                245                 250                 255

Met Met Leu Leu Ala Tyr Leu Ser Tyr Met Leu Ala Glu Leu Phe His
                260                 265                 270

Leu Ser Ser Ile Leu Thr Val Phe Phe Cys Gly Ile Val Met Ser His
        275                 280                 285

Tyr Thr Trp His Asn Val Thr Asp Lys Ser Lys Val Thr Thr Lys His
        290                 295                 300

Thr Phe Ala Ala Met Ser Phe Leu Ala Glu Ile Phe Ile Phe Leu Tyr
305                 310                 315                 320

Val Gly Met Asp Ala Leu Asp Ile Glu Lys Trp Asp Val Val Arg Asn
                325                 330                 335

Ser Pro Gly Gln Ser Ile Gly Val Ser Ser Ile Leu Leu Gly Leu Ile
                340                 345                 350

Leu Leu Gly Arg Ala Ala Phe Val Phe Pro Leu Ser Phe Leu Ser Asn
            355                 360                 365

Leu Thr Lys Ser Ser Pro Asp Glu Lys Ile Asp Leu Lys Lys Gln Val
        370                 375                 380

Thr Ile Trp Trp Ala Gly Leu Met Arg Gly Ala Val Ser Met Ala Leu
385                 390                 395                 400

Ala Tyr Asn Gln Phe Thr Thr Ser Gly His Thr Lys Val Leu Gly Asn
                405                 410                 415

Ala Ile Met Ile Thr Ser Thr Ile Thr Val Val Leu Phe Ser Thr Val
            420                 425                 430

Val Phe Gly Leu Leu Thr Lys Pro Leu Val Lys His Leu Gln Pro Ser
        435                 440                 445

Ser Lys Gln Ser Ser Thr Thr Ala Leu Gln Ile Thr Leu Arg Ser Ser
    450                 455                 460

Phe His Asp Pro Ile Leu His Glu Pro Leu Leu Ser Thr Gln Gly Gln
465                 470                 475                 480
```

```
Ser Glu Tyr Asp Pro Glu Gln His Val Ser Phe Arg Met Phe Trp Lys
                485                 490                 495

Ser Pro Ser Arg Ala Ile His His Tyr Trp Arg Lys Phe Asp Asn Ala
            500                 505                 510

Val Met Arg Arg Ile Phe Gly Gly Arg Gly Val Ser Pro Val Val Pro
                515                 520                 525

Gly Ser Pro Ile Glu Asn Ser Val Pro Gln Trp Ser Glu Glu Val Glu
        530                 535                 540

Asn Lys Glu Gln Asn Gly Glu Pro
545                 550

<210> SEQ ID NO 16
<211> LENGTH: 487
<212> TYPE: PRT
<213> ORGANISM: Arabidopsis thaliana

<400> SEQUENCE: 16

Met Glu Glu Val Met Ile Ser Pro Val Glu His Asp Pro Gln Gly Gln
  1               5                  10                  15

Val Lys Gln Gln Gln Ala Ala Gly Val Gly Ile Leu Leu Gln Ile Met
                 20                  25                  30

Met Leu Val Leu Ser Phe Val Leu Gly His Val Leu Arg Arg His Arg
             35                  40                  45

Phe His Tyr Leu Pro Glu Ala Ser Gly Leu Ile Val Gly Ile Leu Ala
         50                  55                  60

Asn Ile Ser Asp Thr Glu Thr Ser Ile Arg Phe Cys Pro Pro Pro Ser
 65                  70                  75                  80

Ile Pro Glu Phe Ser Leu Leu Ser Phe Pro Arg Ser Leu Lys Pro Phe
                 85                  90                  95

Phe Ser Asn Phe Gly Ala Ile Val Thr Phe Ala Ile Ile Gly Thr Phe
                100                 105                 110

Val Ala Ser Val Val Thr Gly Gly Leu Val Tyr Leu Gly Gly Ser Met
                115                 120                 125

Tyr Leu Met Tyr Lys Leu Pro Phe Val Glu Cys Leu Met Phe Gly Ala
            130                 135                 140

Leu Ile Ser Ala Thr Asp Pro Val Thr Val Leu Ser Ile Phe Gln Asp
145                 150                 155                 160

Val Gly Thr Asp Val Asn Leu Tyr Ala Leu Val Phe Gly Glu Ser Val
                165                 170                 175

Leu Asn Asp Ala Val Ser Phe Tyr Tyr Leu Leu Arg Tyr Trp Ala Leu
            180                 185                 190

Pro Phe Lys Phe Phe Glu Thr Phe Ala Gly Ser Met Ser Ala Glu His
        195                 200                 205

Leu Phe Lys Tyr Ala Gly Leu Asp Thr Glu Asn Leu Gln Asn Leu Glu
    210                 215                 220

Cys Cys Leu Phe Val Leu Phe Pro Tyr Phe Ser Tyr Met Leu Ala Glu
225                 230                 235                 240

Gly Val Gly Leu Ser Gly Ile Val Ser Ile Leu Phe Thr Gly Ile Val
                245                 250                 255

Met Lys Arg Tyr Thr Phe Ser Asn Leu Ser Glu Ala Ser Gln Ser Phe
            260                 265                 270

Val Ser Ser Phe Phe His Leu Ile Ser Ser Leu Ala Glu Thr Phe Thr
        275                 280                 285

Phe Ile Tyr Met Gly Phe Asp Ile Ala Met Glu Gln His Ser Trp Ser
    290                 295                 300
```

```
His Val Gly Phe Ile Leu Phe Ser Ile Val Ser Ser Phe Thr Asp Arg
305                 310                 315                 320

Gln Ala Val Asn Val Phe Gly Cys Ala Tyr Leu Val Asn Leu Phe Arg
            325                 330                 335

Gln Glu Asn Gln Lys Ile Pro Met Lys His Gln Lys Ala Leu Trp Tyr
        340                 345                 350

Ser Gly Leu Arg Gly Ala Met Ala Phe Ala Leu Ala Leu Gln Ser Leu
    355                 360                 365

His Asp Leu Pro Glu Gly His Gly Gln Ile Ile Phe Thr Ala Thr Thr
370                 375                 380

Thr Ile Val Val Val Thr Val Leu Leu Ile Gly Gly Ser Thr Gly Lys
385                 390                 395                 400

Met Leu Glu Ala Leu Glu Val Val Gly Asp Asp Leu Asp Asp Ser Met
            405                 410                 415

Ser Glu Gly Phe Glu Glu Ser Asp His Gln Tyr Val Pro Pro Pro Phe
            420                 425                 430

Ser Ile Gly Ala Ser Ser Asp Glu Asp Thr Ser Ser Ser Gly Ser Arg
        435                 440                 445

Phe Lys Met Lys Leu Lys Glu Phe His Lys Thr Thr Thr Ser Phe Thr
    450                 455                 460

Ala Leu Asp Lys Asn Phe Leu Thr Pro Phe Phe Thr Thr Asn Ser Gly
465                 470                 475                 480

Asp Gly Asp Gly Asp Gly Glu
                485

<210> SEQ ID NO 17
<211> LENGTH: 531
<212> TYPE: PRT
<213> ORGANISM: Arabidopsis thaliana

<400> SEQUENCE: 17

Met Ser Ser Glu Leu Gln Ile Ser Pro Ala Ile His Asp Pro Gln Gly
1               5                   10                  15

Gln Glu Lys Gln Gln Ala Ala Gly Val Gly Ile Leu Leu Gln Ile
            20                  25                  30

Met Met Leu Val Leu Ser Phe Val Leu Gly His Val Leu Arg Arg His
        35                  40                  45

Lys Phe Tyr Tyr Leu Pro Glu Ala Ser Ala Ser Leu Leu Ile Gly Leu
    50                  55                  60

Ile Val Gly Gly Leu Ala Asn Ile Ser Asn Thr Glu Thr Ser Ile Arg
65                  70                  75                  80

Phe Val Glu Leu Phe Leu Ile Ser Phe Phe Arg His Gly Ser Ile Ser
                85                  90                  95

Thr Met Ser Ser Ser Phe Cys Phe Cys Cys Leu Pro Ser Tyr Tyr Ile
            100                 105                 110

Leu Lys Ile Glu Tyr Leu Gly Gly Val Met Phe Leu Met Tyr Arg Leu
        115                 120                 125

Pro Phe Val Glu Cys Leu Met Phe Gly Ser Leu Ile Ser Ala Thr Asp
    130                 135                 140

Pro Val Thr Val Leu Ser Ile Phe Gln Glu Leu Gly Ser Asp Val Asn
145                 150                 155                 160

Leu Tyr Ala Leu Val Phe Gly Glu Ser Val Leu Asn Asp Ala Asp Glu
                165                 170                 175

Ile Val Thr Leu Leu Ile Arg Ser Phe Ser Phe Leu Cys Cys Phe Trp
            180                 185                 190
```

```
Gln Met Ala Ile Ser Leu Tyr Arg Thr Met Ser Leu Val Arg Ser His
        195                 200                 205

Ser Ser Gly Gln Asn Phe Phe Met Val Ile Val Arg Phe Leu Glu Thr
        210                 215                 220

Phe Val Gly Ser Met Ser Ala Ala Met Lys Tyr Phe Ile Leu Met Tyr
225                 230                 235                 240

Ser Leu Leu Leu Ser Val Tyr Arg Thr Trp Ser Ala Val Ser Ser Tyr
                245                 250                 255

Phe Phe His Ile Ser Arg Asn Lys Thr Leu Leu Phe Tyr Thr Ser Tyr
                260                 265                 270

Val Ser Ile Tyr Phe Thr Leu Ile Glu Ile Val Gln Phe Val Met Lys
            275                 280                 285

His Tyr Thr Tyr Ser Asn Leu Ser Ala Asn Ser Gln Arg Phe Val Ser
        290                 295                 300

Ala Phe Phe His Leu Ile Ser Ser Leu Ala Glu Thr Phe Val Phe Ile
305                 310                 315                 320

Tyr Met Gly Phe Asp Ile Ala Met Glu Lys His Ser Trp Ala Ala Asn
                325                 330                 335

Val Phe Gly Cys Gly Tyr Leu Val Asn Leu Ala Arg Pro Ala His Arg
                340                 345                 350

Lys Ile Pro Met Thr His Gln Lys Ala Leu Trp Tyr Ser Gly Lys Ile
            355                 360                 365

Leu Leu Cys Val Pro Leu Ser Ser Tyr Cys Phe Tyr Ser Ser Val Ile
        370                 375                 380

Asn Thr Lys Ile Cys Gly Phe Cys Ile Gly Leu Arg Gly Ala Met Ala
385                 390                 395                 400

Phe Ala Leu Ala Leu Gln Ser Val His Asp Leu Pro Glu Gly His Gly
                405                 410                 415

Gln Thr Ile Phe Thr Ala Thr Thr Ala Ile Val Val Leu Thr Val Leu
                420                 425                 430

Leu Ile Gly Gly Ser Thr Gly Thr Met Leu Glu Ala Leu Glu Val Val
            435                 440                 445

Gly Asp Ser His Asp Thr Ser Leu Gly Asp Gly Phe Glu Val Val Asn
        450                 455                 460

Ser Arg Tyr Met Thr Ser Tyr Asp Asp Glu Asp Thr Pro Pro Gly Ser
465                 470                 475                 480

Gly Phe Arg Thr Lys Leu Arg Glu Phe His Lys Ser Ala Ala Ser Phe
                485                 490                 495

Thr Glu Leu Asp Arg Asn Tyr Leu Thr Pro Phe Phe Thr Ser Asn Asn
                500                 505                 510

Gly Asp Tyr Asp Asp Glu Gly Asn Met Glu Gln His His Gly Asn Asn
            515                 520                 525

Ile Ile Leu
        530

<210> SEQ ID NO 18
<211> LENGTH: 697
<212> TYPE: PRT
<213> ORGANISM: Arabidopsis thaliana

<400> SEQUENCE: 18

Met Thr Ser Ile Ile Gly Ala Ala Leu Pro Tyr Lys Ser Pro Glu Lys
1               5                   10                  15

Ala Ile Ala Ser Ser Ser Tyr Ser Ala Glu Asn Asp Ser Ser Pro Val
            20                  25                  30
```

```
Asp Ala Val Ile Phe Ala Gly Thr Ser Leu Val Leu Gly Thr Ala Cys
         35                  40                  45

Arg Tyr Leu Phe Asn Gly Thr Arg Val Pro Tyr Thr Val Leu Leu
     50                  55                  60

Val Ile Gly Ile Phe Leu Gly Ser Leu Glu Tyr Gly Thr Lys His Asn
 65                  70                  75                  80

Leu Gly Lys Leu Gly His Gly Ile Arg Ile Trp Asn Gly Ile Asn Pro
                     85                  90                  95

Asp Leu Leu Leu Ala Val Phe Leu Pro Val Leu Leu Phe Glu Ser Ser
                 100                 105                 110

Phe Ser Met Asp Val His Gln Ile Lys Arg Cys Met Gly Gln Met Val
             115                 120                 125

Leu Leu Ala Gly Pro Gly Val Leu Ile Ser Thr Phe Cys Leu Gly Ala
         130                 135                 140

Leu Ile Lys Leu Thr Phe Pro Tyr Asn Trp Asp Trp Lys Thr Ser Leu
145                 150                 155                 160

Leu Leu Gly Gly Leu Leu Gly Ala Thr Asp Pro Val Ala Val Val Ala
                 165                 170                 175

Leu Leu Lys Glu Leu Gly Ala Ser Lys Lys Met Thr Thr Leu Ile Asp
             180                 185                 190

Gly Glu Ser Leu Met Asn Asp Gly Val Ser Val Val Phe Gln Leu
         195                 200                 205

Phe Phe Lys Met Val Met Gly His Asn Ser Asp Trp Gly Ser Ile Ile
     210                 215                 220

Lys Phe Leu Val Gln Asn Ser Phe Gly Ala Val Gly Ile Gly Leu Ala
225                 230                 235                 240

Phe Gly Ile Ala Ser Val Phe Trp Leu Lys Phe Ile Phe Asn Asp Thr
                 245                 250                 255

Val Ala Gln Ile Thr Val Thr Leu Ser Ala Ser Tyr Phe Ala Tyr Tyr
             260                 265                 270

Thr Ala Gln Glu Trp Ala Gly Val Ser Gly Ile Leu Thr Val Met Ile
         275                 280                 285

Leu Gly Met Phe Phe Ala Ala Phe Ala Arg Thr Ala Phe Lys Gly Asp
     290                 295                 300

Ser His Gln Ser Leu His His Phe Trp Tyr Phe Thr Thr Gln Glu Met
305                 310                 315                 320

Ala Ala Tyr Ile Ala Asn Thr Leu Val Phe Met Leu Ser Gly Val Ile
                 325                 330                 335

Ile Ala Glu Ser Val Leu Ser Gly Gln Thr Ile Ser Tyr Lys Ala Ile
             340                 345                 350

Lys Trp Lys Phe Ile Ser Gln Phe Arg Tyr Gly Asn Lys Ala Val Leu
         355                 360                 365

Gln Phe Leu Phe Leu Thr Gly Gly Ile Val Phe Leu Thr Leu Val Val
     370                 375                 380

Asn Gly Ser Thr Thr Gln Leu Leu His Leu Leu Arg Met Asp Thr
385                 390                 395                 400

Leu Thr Ala Thr Lys Lys Arg Ile Leu Glu Tyr Thr Lys Phe Glu Met
                 405                 410                 415

Met Lys Thr Ala Leu Lys Ala Phe Glu Asn Leu Gly Asp Asp Glu Glu
             420                 425                 430

Leu Gly Ser Ala Asp Trp Pro Thr Val Ile Arg His Ile Ser Ser Leu
         435                 440                 445

Lys Asp Leu Glu Gly Arg Gln Val Asn Pro His Asp Gly Tyr Glu Ala
```

```
                    450                 455                 460
Gly Ser Leu Asp Pro Thr Asn Ile Met Asp Ile Arg Val Gln Ala Ala
465                 470                 475                 480

Tyr Trp Glu Met Leu Asp Asp Gly Arg Ile Thr Gln Cys Thr Ala Asn
                485                 490                 495

Val Leu Met Gln Ser Val Asp Glu Ala Leu Asp Leu Val Ser Thr Ser
                500                 505                 510

Ser Leu Ser Asp Trp Arg Gly Leu Glu Pro Arg Val His Phe Pro Asn
            515                 520                 525

Tyr Tyr Lys Phe Leu Gln Ser Lys Ile Ile Pro His Lys Leu Val Thr
        530                 535                 540

His Leu Ile Val Glu Arg Leu Glu Ser Ala Cys Tyr Ile Ser Ser Ala
545                 550                 555                 560

Phe Leu Arg Ala His Arg Ile Ala Arg Gln Gln Leu His Ile Phe Leu
                565                 570                 575

Gly Asn Ser Asn Ile Ala Ser Thr Val Ile Asn Glu Ser Glu Val Glu
                580                 585                 590

Gly Glu Glu Ala Lys Gln Phe Leu Glu Asp Val Arg Asp Ser Phe Pro
            595                 600                 605

Gln Val Leu Ser Val Leu Lys Thr Arg Gln Val Thr His Tyr Val Leu
        610                 615                 620

Asn His Leu Asn Gly Tyr Ile Lys Asn Leu Glu Lys Val Gly Leu Leu
625                 630                 635                 640

Glu Gly Lys Glu Val Ser His Leu His Asp Val Val Gln Ser Asp Leu
                645                 650                 655

Lys Lys Leu Leu Arg His Pro Pro Ser Leu Lys Leu Pro Asn Val Asp
            660                 665                 670

Asp Leu Ile Thr Ser Asn Pro Leu Leu Lys Asp Arg Ser Ser Phe Arg
        675                 680                 685

Ser Leu Ala Ile Gly Glu Thr Asp Ala
    690                 695

<210> SEQ ID NO 19
<211> LENGTH: 697
<212> TYPE: PRT
<213> ORGANISM: Arabidopsis thaliana

<400> SEQUENCE: 19

Met Thr Ser Ile Ile Gly Ala Ala Leu Pro Tyr Lys Ser Pro Glu Lys
  1               5                  10                  15

Ala Ile Ala Ser Ser Tyr Ser Ala Glu Asn Asp Ser Ser Pro Val
                20                  25                  30

Asp Ala Val Ile Phe Ala Gly Ser Leu Val Leu Gly Thr Ala Cys
            35                  40                  45

Arg Tyr Leu Phe Asn Gly Thr Arg Val Pro Tyr Thr Val Val Leu Leu
     50                  55                  60

Val Ile Gly Ile Phe Leu Gly Ser Leu Glu Tyr Gly Thr Lys His Asn
 65                  70                  75                  80

Leu Gly Lys Leu Gly His Gly Ile Arg Ile Trp Asn Gly Ile Asn Pro
                85                  90                  95

Asp Leu Leu Leu Ala Val Phe Leu Pro Val Leu Leu Phe Glu Ser Ser
            100                 105                 110

Phe Ser Met Asp Val His Gln Ile Lys Arg Cys Met Gly Gln Met Val
        115                 120                 125

Leu Leu Ala Gly Pro Gly Val Leu Ile Ser Thr Phe Cys Leu Gly Ala
```

-continued

```
                130                 135                 140
Leu Ile Lys Leu Thr Phe Pro Tyr Asn Trp Asp Trp Lys Thr Ser Leu
145                 150                 155                 160

Leu Leu Gly Gly Leu Leu Gly Ala Thr Asp Pro Val Ala Val Val Ala
                165                 170                 175

Leu Leu Lys Glu Leu Gly Ala Ser Lys Lys Met Thr Thr Leu Ile Asp
                180                 185                 190

Gly Glu Ser Leu Met Asn Asp Gly Val Ser Val Val Phe Gln Leu
                195                 200                 205

Phe Phe Lys Met Val Met Gly His Asn Ser Asp Trp Gly Ser Ile Ile
        210                 215                 220

Lys Phe Leu Val Gln Asn Ser Phe Gly Ala Val Gly Ile Gly Leu Ala
225                 230                 235                 240

Phe Gly Ile Ala Ser Val Phe Trp Leu Lys Phe Ile Phe Asn Asp Thr
                245                 250                 255

Val Ala Gln Ile Thr Val Thr Leu Ser Ala Ser Tyr Phe Ala Tyr Tyr
                260                 265                 270

Thr Ala Gln Glu Trp Ala Gly Val Ser Gly Ile Leu Thr Val Met Ile
        275                 280                 285

Leu Gly Met Phe Phe Ala Ala Phe Ala Arg Thr Ala Phe Lys Gly Asp
        290                 295                 300

Ser His Gln Ser Leu His Phe Trp Tyr Phe Thr Thr Gln Glu Met
305                 310                 315                 320

Ala Ala Tyr Ile Ala Asn Thr Leu Val Phe Met Leu Ser Gly Val Ile
                325                 330                 335

Ile Ala Glu Ser Val Leu Ser Gly Gln Thr Ile Ser Tyr Lys Ala Ile
                340                 345                 350

Lys Trp Lys Phe Ile Ser Gln Phe Arg Tyr Gly Asn Lys Ala Val Leu
        355                 360                 365

Gln Phe Leu Phe Leu Thr Gly Gly Ile Val Phe Leu Thr Leu Val Val
        370                 375                 380

Asn Gly Ser Thr Thr Gln Leu Leu Leu His Leu Leu Arg Met Asp Thr
385                 390                 395                 400

Leu Thr Ala Thr Lys Lys Arg Ile Leu Glu Tyr Thr Lys Phe Glu Met
                405                 410                 415

Met Lys Thr Ala Leu Lys Ala Phe Glu Asn Leu Gly Asp Asp Glu Glu
                420                 425                 430

Leu Gly Ser Ala Asp Trp Pro Thr Val Ile Arg His Ile Ser Ser Leu
        435                 440                 445

Lys Asp Leu Glu Gly Arg Gln Val Asn Pro His Asp Gly Tyr Glu Ala
450                 455                 460

Gly Ser Leu Asp Pro Thr Asn Ile Met Asp Ile Arg Val Gln Ala Ala
465                 470                 475                 480

Tyr Trp Glu Met Leu Asp Asp Gly Arg Ile Thr Gln Cys Thr Ala Asn
                485                 490                 495

Val Leu Met Gln Ser Val Asp Glu Ala Leu Asp Leu Val Ser Thr Ser
                500                 505                 510

Ser Leu Ser Asp Trp Arg Gly Leu Glu Pro Arg Val His Phe Pro Asn
        515                 520                 525

Tyr Tyr Lys Phe Leu Gln Ser Lys Ile Ile Pro His Lys Leu Val Thr
        530                 535                 540

His Leu Ile Val Glu Arg Leu Glu Ser Ala Cys Tyr Ile Ser Ser Ala
545                 550                 555                 560
```

```
Phe Leu Arg Ala His Arg Ile Ala Arg Gln Gln Leu His Ile Phe Leu
                565                 570                 575

Gly Asn Ser Asn Ile Ala Ser Thr Val Ile Asn Glu Ser Glu Val Glu
            580                 585                 590

Gly Glu Glu Ala Lys Gln Phe Leu Glu Asp Val Arg Asp Ser Phe Pro
        595                 600                 605

Gln Val Leu Ser Val Leu Lys Thr Arg Gln Val Thr His Tyr Val Leu
    610                 615                 620

Asn His Leu Asn Gly Tyr Ile Lys Asn Leu Glu Lys Val Gly Leu Leu
625                 630                 635                 640

Glu Gly Lys Glu Val Ser His Leu His Asp Val Gln Ser Asp Leu
                645                 650                 655

Lys Lys Leu Leu Arg His Pro Pro Ser Leu Lys Leu Pro Asn Val Asp
                660                 665                 670

Asp Leu Ile Thr Ser Asn Pro Leu Leu Lys Asp Arg Ser Ser Phe Arg
            675                 680                 685

Ser Leu Ala Ile Gly Glu Thr Asp Ala
        690                 695

<210> SEQ ID NO 20
<211> LENGTH: 534
<212> TYPE: PRT
<213> ORGANISM: Lycopersicon esculentum

<400> SEQUENCE: 20

Met Gly Leu Asp Ala Val Ala Arg Leu Gly Val Ser Ile Leu Ser Asp
  1               5                  10                  15

Gly Asp Gln Val Ser Val Asp Ser Ile Thr Leu Phe Val Ala Leu Leu
                20                  25                  30

Cys Gly Cys Ile Val Ile Gly His Leu Leu Glu Glu Ser Arg Trp Ile
            35                  40                  45

Asn Asp Ser Ile Thr Thr Leu Val Ile Gly Leu Ser Thr Gly Gly Ile
        50                  55                  60

Ile Leu Leu Thr Thr Lys Gly Lys Ser Ser His Leu Leu Glu Phe Asp
 65                  70                  75                  80

Glu Gln Leu Phe Phe Ile Tyr Val Leu Pro Pro Ile Ile Phe Asn Ala
                85                  90                  95

Gly Phe Gln Val Lys Lys Lys Gln Phe Arg Asn Phe Val Thr Ile
                100                 105                 110

Met Leu Phe Gly Ala Val Gly Thr Leu Ile Ser Phe Ser Ile Ser
            115                 120                 125

Phe Gly Ala Lys Glu Leu Leu Gly Lys Leu Asp Ile Gly Phe Leu Glu
                130                 135                 140

Leu Arg Asp Tyr Leu Ala Ile Gly Ala Ile Phe Ser Ala Thr Asp Ser
145                 150                 155                 160

Val Cys Thr Leu Gln Ala Leu Asn Gln Asp Thr Pro Arg Leu Tyr
                165                 170                 175

Ser Leu Val Phe Gly Glu Gly Val Val Asn Asp Ala Thr Ser Val Val
            180                 185                 190

Leu Phe Asn Ala Ile Gln Lys Leu Asp Leu Ser His Ile Asn Ser Arg
        195                 200                 205

Ala Ala Leu Val Phe Thr Gly Asn Phe Leu Tyr Leu Phe Leu Ala Ser
    210                 215                 220

Thr Phe Leu Gly Val Leu Ile Gly Leu Leu Ser Ala Tyr Leu Ile Lys
225                 230                 235                 240
```

-continued

```
Lys Ile Tyr Leu Gly Arg His Ser Thr Asp Arg Glu Val Ala Leu Met
                245                 250                 255

Ile Leu Met Ala Tyr Leu Ser Tyr Val Met Ala Glu Leu Phe Asp Leu
            260                 265                 270

Ser Gly Ile Leu Thr Val Phe Ile Cys Gly Ile Val Met Ser His Tyr
        275                 280                 285

Thr Trp His Asn Val Thr Phe Asn Ser Lys Val Thr Thr Arg His Ala
    290                 295                 300

Phe Ala Thr Leu Ser Phe Ile Ala Glu Ile Phe Ile Phe Leu Tyr Val
305                 310                 315                 320

Gly Met Asp Ala Leu Asp Ile Glu Lys Trp Arg Phe Val Lys Asp Ser
                325                 330                 335

Pro Gly Lys Ser Val Gly Val Ser Ala Ala Leu Leu Gly Leu Val Leu
            340                 345                 350

Val Gly Arg Ala Cys Phe Val Phe Pro Leu Ser Leu Phe Ser Asn Cys
        355                 360                 365

Leu Lys Arg Ser Glu His Asp Lys Phe Gly Leu Lys Leu Gln Val Thr
    370                 375                 380

Ile Trp Trp Ala Gly Leu Met Arg Gly Ser Val Ser Met Ala Leu Ala
385                 390                 395                 400

Tyr Asn Gln Phe Thr Arg Phe Gly His Thr Gln Gln Pro Gly Asn Ala
                405                 410                 415

Val Met Ile Thr Ser Thr Ile Thr Ile Val Leu Phe Ser Thr Val Val
            420                 425                 430

Phe Gly Leu Ile Thr Lys Pro Leu Val Arg Phe Leu Leu Pro Ser Ser
        435                 440                 445

Gln Gly Phe Asn Asn Leu Ile Ser Ser Glu Gln Ser Phe Ala Arg Pro
    450                 455                 460

Leu Leu Thr Asn Glu Gln Glu Leu Glu Leu Glu Met Gly Asn Val Asp
465                 470                 475                 480

Pro Val Arg Pro Ser Gly Leu Ser Ile Leu Leu Lys Glu Pro Ser Tyr
                485                 490                 495

Thr Ile His Asn His Trp Arg Arg Phe Asp Asp Ala Phe Met Arg Pro
            500                 505                 510

Leu Phe Gly Gly Arg Gly Phe Val Pro Asp Ala Pro Glu Leu Ser Lys
        515                 520                 525

Gly Gly Cys Asp Gln Tyr
    530
```

<210> SEQ ID NO 21
<211> LENGTH: 531
<212> TYPE: PRT
<213> ORGANISM: Lycopersicon esculentum

<400> SEQUENCE: 21

```
Met Glu Asp His Leu Gln Ile Ser Pro Ala Gly Ala Lys Ala Ile Pro
  1               5                  10                  15

Gly Lys Glu Gln Gln Ala Ala Gly Tyr Gly Ile Leu Leu Gln Ile Met
                20                  25                  30

Met Leu Val Leu Ser Phe Val Ile Gly His Val Leu Arg Arg Arg His
            35                  40                  45

Phe Tyr Tyr Ile Pro Glu Ala Ser Ala Ser Leu Leu Ile Gly Leu Ile
    50                  55                  60

Val Gly Gly Leu Ala Asn Val Ser Asp Thr Glu Thr Ser Ile Arg Ala
65                  70                  75                  80
```

```
Trp Phe Asn Phe His Glu Glu Phe Phe Phe Leu Phe Leu Leu Pro Pro
                85                  90                  95
Ile Ile Phe Gln Ser Gly Phe Ser Leu Ser Pro Lys Pro Phe Phe Ser
            100                 105                 110
Asn Phe Gly Ala Ile Ile Thr Phe Ala Ile Leu Gly Thr Phe Ile Ala
            115                 120                 125
Ser Phe Val Thr Gly Ile Leu Val Tyr Leu Gly Gly Val Thr Tyr Leu
            130                 135                 140
Met Tyr Arg Leu Pro Phe Val Glu Cys Leu Met Phe Gly Ala Leu Ile
145                 150                 155                 160
Ser Ala Thr Asp Pro Val Thr Val Leu Ser Ile Phe Gln Glu Leu Gly
                165                 170                 175
Thr Asp Val Asn Leu Tyr Ala Leu Val Phe Gly Glu Ser Val Leu Asn
            180                 185                 190
Asp Ala Met Ala Ile Ser Leu Tyr Arg Thr Met Ser Leu Val Arg Ser
            195                 200                 205
His Met Ser Thr Asp Gln Asn Tyr Phe Met Ile Thr Ile Arg Phe Val
    210                 215                 220
Glu Thr Phe Met Gly Ser Leu Ser Ala Gly Val Gly Val Gly Phe Val
225                 230                 235                 240
Ser Ala Leu Leu Phe Lys Tyr Ala Gly Leu Asp Ile Asp Asn Leu Gln
                245                 250                 255
Asn Leu Glu Ser Cys Leu Phe Val Leu Phe Pro Tyr Phe Ser Tyr Met
            260                 265                 270
Leu Ala Glu Gly Leu Gly Leu Ser Gly Ile Val Ser Ile Leu Phe Thr
            275                 280                 285
Gly Val Val Met Lys Arg Tyr Thr Tyr Pro Asn Leu Ser Glu Ser Ser
290                 295                 300
Gln Arg Phe Val Ser Ala Phe Phe His Leu Ile Ser Ser Leu Ala Glu
305                 310                 315                 320
Thr Phe Val Phe Ile Tyr Met Gly Phe Asp Ile Ala Met Glu Lys His
                325                 330                 335
Ser Trp Ser His Val Gly Phe Ile Phe Phe Ser Ile Leu Phe Ile Val
            340                 345                 350
Ile Ala Arg Ala Ala Asn Val Phe Gly Cys Ala Tyr Leu Val Asn Leu
            355                 360                 365
Val Arg Pro His Gln Lys Ile Pro Ala Lys His Gln Lys Ala Leu
370                 375                 380
Trp Tyr Ser Gly Leu Arg Gly Ala Met Ala Phe Ala Leu Ala Leu Gln
385                 390                 395                 400
Pro Val His Asp Leu Pro Glu Gly His Gly Gln Ala Ile Phe Thr Ala
                405                 410                 415
Thr Thr Ala Ile Val Val Leu Thr Val Leu Ile Ile Gly Gly Ser Ala
            420                 425                 430
Gly Thr Met Leu Glu Ala Leu Glu Val Val Gly Asp Gly Gln Ser Gly
            435                 440                 445
Ser Met Asp Glu Thr Phe Glu Gly Asn Asn Gly Tyr Ile Ala Pro Ser
    450                 455                 460
Tyr Arg Asp Glu Ser Tyr Asp Gly Glu Pro Ser Ser Gly Asn Arg Phe
465                 470                 475                 480
Arg Met Lys Leu Lys Glu Phe His Lys Ser Thr Thr Ser Phe Ser Ala
                485                 490                 495
Leu Asp Lys Asn Tyr Leu Thr Pro Phe Phe Thr Thr Gln Gly Gly Asp
            500                 505                 510
```

```
Glu Asp Glu Asp Glu Pro Ile Met His Ser Ser Arg Arg Ala Gly Tyr
        515                 520                 525

Asp Gly His
    530

<210> SEQ ID NO 22
<211> LENGTH: 535
<212> TYPE: PRT
<213> ORGANISM: Oryza sativa

<400> SEQUENCE: 22

Met Gly Met Glu Val Ala Ala Ala Arg Leu Gly Ala Leu Tyr Thr Thr
  1               5                  10                  15

Ser Asp Tyr Ala Ser Val Val Ser Ile Asn Leu Phe Val Ala Leu Leu
             20                  25                  30

Cys Ala Cys Ile Val Leu Gly His Leu Leu Glu Glu Asn Arg Trp Val
         35                  40                  45

Asn Glu Ser Ile Thr Ala Leu Ile Ile Gly Leu Cys Thr Gly Val Val
 50                  55                  60

Ile Leu Leu Met Thr Lys Gly Lys Ser Ser His Leu Phe Val Phe Ser
 65                  70                  75                  80

Glu Asp Leu Phe Phe Ile Tyr Leu Leu Pro Pro Ile Ile Phe Asn Ala
                 85                  90                  95

Gly Phe Gln Val Lys Lys Lys Gln Phe Phe Arg Asn Phe Met Thr Ile
            100                 105                 110

Thr Leu Phe Gly Ala Val Gly Thr Met Ile Ser Phe Phe Thr Ile Ser
            115                 120                 125

Ile Ala Ala Ile Ala Ile Phe Ser Arg Met Asn Ile Gly Thr Leu Asp
130                 135                 140

Val Gly Asp Phe Leu Ala Ile Gly Ala Ile Phe Ser Ala Thr Asp Ser
145                 150                 155                 160

Val Cys Thr Leu Gln Val Leu Asn Gln Asp Glu Thr Pro Phe Leu Tyr
                165                 170                 175

Ser Leu Val Phe Gly Glu Gly Val Val Asn Asp Ala Thr Ser Ile Val
            180                 185                 190

Leu Phe Asn Ala Leu Gln Asn Phe Asp Leu Val His Ile Asp Ala Ala
            195                 200                 205

Val Val Leu Lys Phe Leu Gly Asn Phe Phe Tyr Leu Phe Leu Ser Ser
210                 215                 220

Thr Phe Leu Gly Val Phe Ala Gly Leu Leu Ser Ala Tyr Ile Ile Lys
225                 230                 235                 240

Lys Leu Tyr Ile Gly Arg His Ser Thr Asp Arg Glu Val Ala Leu Met
                245                 250                 255

Met Leu Met Ala Tyr Leu Ser Tyr Met Leu Ala Glu Leu Leu Asp Leu
            260                 265                 270

Ser Gly Ile Leu Thr Val Phe Phe Cys Gly Ile Val Met Ser His Tyr
            275                 280                 285

Thr Trp His Asn Val Thr Glu Ser Ser Arg Val Thr Thr Lys His Ala
        290                 295                 300

Phe Ala Thr Leu Ser Phe Ile Ala Glu Thr Phe Leu Phe Leu Tyr Val
305                 310                 315                 320

Gly Met Asp Ala Leu Asp Ile Glu Lys Trp Glu Phe Ala Ser Asp Arg
                325                 330                 335

Pro Gly Lys Ser Ile Gly Ile Ser Ser Ile Leu Leu Gly Leu Val Leu
            340                 345                 350
```

```
Ile Gly Arg Ala Ala Phe Val Phe Pro Leu Ser Phe Leu Ser Asn Leu
            355                 360                 365

Thr Lys Lys Ala Pro Asn Glu Lys Ile Thr Trp Arg Gln Gln Val Val
    370                 375                 380

Ile Trp Trp Ala Gly Leu Met Arg Gly Ala Val Ser Ile Ala Leu Ala
385                 390                 395                 400

Tyr Asn Lys Phe Thr Arg Ser Gly His Thr Gln Leu His Gly Asn Ala
                405                 410                 415

Ile Met Ile Thr Ser Thr Ile Thr Val Val Leu Phe Ser Thr Met Val
            420                 425                 430

Phe Gly Met Met Thr Lys Pro Leu Ile Arg Leu Leu Leu Pro Ala Ser
                435                 440                 445

Gly His Pro Val Thr Ser Glu Pro Ser Ser Pro Lys Ser Leu His Ser
            450                 455                 460

Pro Leu Leu Thr Ser Met Gln Gly Ser Asp Leu Glu Ser Thr Thr Asn
465                 470                 475                 480

Ile Val Arg Pro Ser Ser Leu Arg Met Leu Leu Thr Lys Pro Thr His
                485                 490                 495

Thr Val His Tyr Tyr Trp Arg Lys Phe Asp Asp Ala Leu Met Arg Pro
            500                 505                 510

Met Phe Gly Gly Arg Gly Phe Val Pro Phe Ser Pro Gly Ser Pro Thr
                515                 520                 525

Glu Gln Ser His Gly Gly Arg
            530                 535

<210> SEQ ID NO 23
<211> LENGTH: 553
<212> TYPE: PRT
<213> ORGANISM: Nierembergia caerulea

<400> SEQUENCE: 23

Met Ala Phe Asp Phe Gly Thr Leu Leu Gly Lys Met Asn Asn Leu Thr
1               5                   10                  15

Thr Ser Asp His Gln Ser Val Val Ser Val Asn Leu Phe Val Ala Leu
            20                  25                  30

Ile Cys Ala Cys Ile Val Ile Gly His Leu Leu Glu Glu Asn Arg Trp
        35                  40                  45

Met Asn Glu Ser Ile Thr Ala Leu Val Ile Gly Ser Cys Thr Gly Val
    50                  55                  60

Ile Ile Leu Leu Ile Ser Gly Gly Lys Asn Ser His Ile Leu Val Phe
65                  70                  75                  80

Ser Glu Asp Leu Phe Phe Ile Tyr Leu Leu Pro Pro Ile Ile Phe Asn
                85                  90                  95

Ala Gly Phe Gln Val Lys Lys Lys Ser Phe Phe Arg Asn Phe Ser Thr
            100                 105                 110

Ile Met Leu Phe Gly Ala Val Gly Thr Leu Ile Ser Phe Ile Ile Ile
        115                 120                 125

Ser Ala Gly Ala Ile Gly Ile Phe Lys Lys Met Asp Ile Gly His Leu
    130                 135                 140

Glu Ile Gly Asp Tyr Leu Ala Ile Gly Ala Ile Phe Ala Ala Thr Asp
145                 150                 155                 160

Ser Val Cys Thr Leu Gln Val Leu Asn Gln Glu Glu Thr Pro Leu Leu
                165                 170                 175

Tyr Ser Leu Val Phe Gly Glu Gly Val Val Asn Asp Ala Thr Ser Val
            180                 185                 190
```

Val Leu Phe Asn Ala Val Gln Asn Phe Asp Leu Ser His Ile Ser Thr
            195                 200                 205

Gly Lys Ala Leu Gln Leu Ile Gly Asn Phe Leu Tyr Leu Phe Ala Ser
            210                 215                 220

Ser Thr Phe Leu Gly Val Ala Val Gly Leu Leu Ser Ala Phe Ile Ile
225                 230                 235                 240

Lys Lys Leu Tyr Phe Gly Arg His Ser Thr Asp Arg Glu Val Ala Ile
            245                 250                 255

Met Ile Leu Met Ala Tyr Leu Ser Tyr Met Leu Ala Glu Leu Phe Tyr
            260                 265                 270

Leu Ser Gly Ile Leu Thr Val Phe Phe Cys Gly Ile Val Met Ser His
            275                 280                 285

Tyr Thr Trp His Asn Val Thr Glu Ser Ser Arg Val Thr Thr Lys His
            290                 295                 300

Thr Phe Ala Thr Leu Ser Phe Ile Ala Glu Ile Phe Ile Phe Leu Tyr
305                 310                 315                 320

Val Gly Met Asp Ala Leu Asp Ile Glu Lys Trp Lys Phe Val Ser Asp
            325                 330                 335

Ser Pro Gly Thr Ser Ile Lys Val Ser Ser Ile Leu Leu Gly Leu Val
            340                 345                 350

Leu Val Gly Arg Gly Ala Phe Val Phe Pro Leu Ser Phe Leu Ser Asn
            355                 360                 365

Leu Thr Lys Lys Asn Pro Glu Asp Lys Ile Ser Phe Asn Gln Gln Val
            370                 375                 380

Thr Ile Trp Trp Ala Gly Leu Met Arg Gly Ala Val Ser Met Ala Leu
385                 390                 395                 400

Ala Tyr Asn Gln Phe Thr Arg Gly Gly His Thr Gln Leu Arg Ala Asn
            405                 410                 415

Ala Ile Met Ile Thr Ser Thr Ile Thr Val Val Leu Phe Ser Thr Val
            420                 425                 430

Val Phe Gly Leu Met Thr Lys Pro Leu Ile Leu Leu Leu Pro Ser
            435                 440                 445

Gln Lys His Leu Ile Arg Met Ile Ser Ser Glu Pro Met Thr Pro Lys
            450                 455                 460

Ser Phe Ile Val Pro Leu Leu Asp Ser Thr Gln Asp Ser Glu Ala Asp
465                 470                 475                 480

Leu Gly Arg His Val Pro Arg Pro His Ser Leu Arg Met Leu Leu Ser
            485                 490                 495

Thr Pro Ser His Thr Val His Tyr Tyr Trp Arg Lys Phe Asp Asn Ala
            500                 505                 510

Phe Met Arg Pro Val Phe Gly Gly Arg Gly Phe Val Pro Phe Val Pro
            515                 520                 525

Gly Ser Pro Thr Glu Pro Val Glu Pro Thr Glu Pro Arg Pro Ala Glu
            530                 535                 540

Ser Arg Pro Thr Glu Pro Thr Asp Glu
545                 550

<210> SEQ ID NO 24
<211> LENGTH: 542
<212> TYPE: PRT
<213> ORGANISM: Citrus x paradisi

<400> SEQUENCE: 24

Met Asp Gln Ala Ile Ser Ser Val Val Arg Lys Leu Gln Met Val Asn
1               5                   10                  15

-continued

```
Thr Ser Asp His Asn Ser Val Val Ser Ile Asn Ile Phe Val Ala Leu
            20                  25                  30
Pro Cys Ala Ser Ile Val Ile Gly His Leu Leu Glu Glu Ser Arg Trp
            35                  40                  45
Met Asn Glu Ser Ile Thr Ala Leu Leu Ile Gly Val Cys Ala Gly Val
 50                  55                  60
Ile Ile Leu Leu Thr Thr Gly Gly Lys Ser Ser His Leu Phe Val Phe
 65                  70                  75                  80
Ser Glu Asp Leu Phe Phe Ile Tyr Val Leu Pro Pro Ile Ile Phe Asn
            85                  90                  95
Ala Gly Phe Gln Val Lys Lys Lys Gln Phe Phe Arg Asn Phe Ile Thr
            100                 105                 110
Ile Met Leu Phe Gly Ala Ile Gly Thr Leu Val Ser Cys Thr Ile Ile
            115                 120                 125
Ser Leu Gly Val Ile Gln Phe Phe Lys Lys Leu Asp Ile Gly Thr Leu
            130                 135                 140
Asp Ile Gly Asp Tyr Leu Ala Ile Gly Ala Ile Phe Ala Ala Thr Asp
145                 150                 155                 160
Ser Val Cys Thr Leu Gln Val Leu Asn Gln Asp Thr Pro Leu Leu
            165                 170                 175
Tyr Ser Leu Val Phe Gly Glu Gly Val Val Asn Asp Ala Thr Ser Val
            180                 185                 190
Val Leu Phe Asn Ala Ile Gln Ser Phe Asp Leu Thr His Ile Asn Thr
            195                 200                 205
Arg Ser Ala Phe Gln Phe Ile Gly Asn Phe Leu Tyr Leu Phe Phe Thr
            210                 215                 220
Ser Thr Leu Leu Gly Val Ile Gly Gly Leu Leu Ser Ala Tyr Val Ile
225                 230                 235                 240
Lys Lys Leu Tyr Phe Gly Arg His Ser Thr Asp Arg Glu Val Ala Ile
            245                 250                 255
Met Val Leu Met Ala Tyr Leu Ser Tyr Met Leu Ala Glu Leu Phe Tyr
            260                 265                 270
Leu Ser Gly Ile Leu Thr Val Phe Phe Cys Gly Ile Val Met Ser His
            275                 280                 285
Tyr Thr Trp His Asn Val Thr Glu Ser Ser Arg Val Thr Thr Lys His
            290                 295                 300
Thr Phe Ala Thr Leu Ser Phe Val Ala Glu Ile Phe Thr Phe Leu Tyr
305                 310                 315                 320
Val Gly Met Asp Ala Leu Asp Ile Glu Lys Trp Arg Phe Val Lys Gly
            325                 330                 335
Ser Pro Gly Thr Ser Val Ala Ala Ser Ala Met Leu Met Gly Leu Ile
            340                 345                 350
Met Ala Gly Arg Ala Ala Phe Val Phe Pro Leu Ser Phe Leu Thr Asn
            355                 360                 365
Leu Ala Lys Lys Ser Pro Thr Glu Lys Ile Ser Ile Lys Gln Gln Val
            370                 375                 380
Ile Ile Trp Trp Ala Gly Leu Met Arg Gly Ala Val Ser Met Ala Leu
385                 390                 395                 400
Ala Tyr Asn Gln Phe Thr Arg Ser Gly His Thr Gln Leu Arg Glu Asn
            405                 410                 415
Ala Ile Met Ile Thr Ser Thr Ile Thr Val Val Leu Phe Ser Thr Val
            420                 425                 430
Val Phe Gly Leu Met Thr Glu Pro Leu Ile Arg Leu Leu Leu Pro His
```

```
                435               440                445
Pro Lys His Thr Thr Asn His Ile Leu Ser Asp Pro Ser Thr Pro Lys
450                 455                 460

Ser Leu Ser Gln Pro Leu Leu Glu Glu Gly Gln Gln Asp Ser Tyr Ala
465                 470                 475                 480

Asp Leu Val Gly Pro Thr Val Pro Arg Pro Gly Ser Leu Arg Ala Leu
                485                 490                 495

Leu Thr Thr Pro Thr His Thr Val His Tyr Tyr Trp Arg Lys Phe Asp
                500                 505                 510

Asp Ala Phe Met Arg Pro Val Phe Gly Gly Arg Gly Phe Ala Pro Phe
                515                 520                 525

Val Pro Gly Ser Pro Thr Glu Arg Ser Val Arg Gly Gly Gln
530                 535                 540

<210> SEQ ID NO 25
<211> LENGTH: 546
<212> TYPE: PRT
<213> ORGANISM: Triticum aestivum

<400> SEQUENCE: 25

Met Gly Leu Asp Leu Gly Ala Leu Ala Leu Lys Tyr Thr Gly Leu Ala
1               5                   10                  15

Val Ser Asp His Asp Ser Ile Val Ala Ile Asn Ile Phe Ile Ala Leu
                20                  25                  30

Leu Cys Gly Cys Ile Val Phe Gly His Leu Leu Glu Gly Asn Arg Trp
            35                  40                  45

Val Asn Glu Ser Thr Thr Ala Leu Val Leu Gly Leu Ile Thr Gly Gly
        50                  55                  60

Val Ile Leu Ile Cys Thr Lys Val Asn Ser Arg Ile Leu Ile Phe
65                  70                  75                  80

Ser Glu Asp Ile Phe Phe Ile Tyr Leu Leu Pro Pro Ile Ile Phe Asn
                85                  90                  95

Ala Gly Phe Gln Val Lys Lys Gln Phe Phe Arg Asn Phe Ala Thr
                100                 105                 110

Ile Ile Leu Phe Gly Ala Ala Gly Thr Leu Ile Ser Phe Val Ile Ile
            115                 120                 125

Thr Phe Gly Ala Met Gly Leu Phe Ser Lys Leu Asp Val Gly Pro Leu
            130                 135                 140

Glu Leu Gly Asp Tyr Leu Ala Ile Gly Ala Ile Phe Ser Ala Thr Asp
145                 150                 155                 160

Ser Val Cys Thr Leu Gln Val Leu Asn Gln Asp Glu Ala Pro Leu Leu
                165                 170                 175

Tyr Ser Leu Val Phe Gly Glu Gly Val Val Asn Asp Ala Thr Ser Val
                180                 185                 190

Val Leu Phe Asn Ala Ile Gln Asn Ile Asp Ile Asn His Phe Asp Val
                195                 200                 205

Phe Val Leu Leu Gln Phe Ile Gly Lys Phe Leu Tyr Leu Phe Phe Thr
                210                 215                 220

Ser Thr Val Leu Gly Val Ala Ala Gly Leu Leu Ser Ala Tyr Ile Ile
225                 230                 235                 240

Lys Lys Leu Cys Phe Ala Arg His Ser Thr Asp Arg Glu Val Ala Ile
                245                 250                 255

Met Ile Leu Met Ala Tyr Leu Ser Tyr Met Leu Ser Met Leu Leu Asp
                260                 265                 270

Leu Ser Gly Ile Leu Thr Val Phe Phe Cys Gly Ile Val Met Ser His
```

```
                    275                 280                 285
Tyr Thr Trp His Asn Val Thr Glu Ser Ser Arg Val Thr Thr Lys His
            290                 295                 300
Thr Phe Ala Thr Leu Ser Phe Ile Ala Glu Ile Phe Leu Phe Leu Tyr
305                 310                 315                 320
Val Gly Met Asp Ala Leu Asp Ile Asp Lys Trp Lys Leu Ala Ser Ser
                325                 330                 335
Ser Pro Lys Lys Pro Ile Ala Leu Ser Ala Val Ile Leu Gly Leu Val
                340                 345                 350
Met Val Gly Arg Ala Ala Phe Val Phe Pro Leu Ser Phe Leu Ser Asn
                355                 360                 365
Leu Ser Lys Lys Glu Ser His Pro Lys Ile Ser Phe Asn Gln Gln Val
            370                 375                 380
Ile Ile Trp Trp Ala Gly Leu Met Arg Gly Ala Val Ser Ile Ala Leu
385                 390                 395                 400
Ala Tyr Asn Lys Phe Thr Thr Ser Gly His Thr Ala Val Arg Val Asn
                405                 410                 415
Ala Val Met Ile Thr Ser Thr Ile Ile Val Leu Phe Ser Thr Met
                420                 425                 430
Val Phe Gly Leu Leu Thr Lys Pro Leu Ile Asn Leu Leu Ile Pro Pro
                435                 440                 445
Arg Pro Gly Thr Ala Ala Asp Ile Ser Ser Gln Ser Phe Leu Asp Pro
                450                 455                 460
Leu Thr Ala Ser Leu Leu Gly Ser Asp Phe Asp Val Gly Gln Leu Thr
465                 470                 475                 480
Pro Gln Thr Asn Leu Gln Tyr Leu Leu Thr Met Pro Thr Arg Ser Val
                485                 490                 495
His Arg Val Trp Arg Lys Phe Asp Asp Lys Phe Met Arg Pro Met Phe
                500                 505                 510
Gly Gly Arg Gly Phe Val Pro Val Pro Gly Ser Pro Ile Glu Arg
                515                 520                 525
Ser Val His Gly Pro Gly Leu Leu Gly Thr Val Thr Glu Ala Glu Asp
                530                 535                 540
Arg Ser
545

<210> SEQ ID NO 26
<211> LENGTH: 538
<212> TYPE: PRT
<213> ORGANISM: Triticum aestivum

<400> SEQUENCE: 26

Met Gly Tyr Gln Val Val Ala Ala Gln Leu Ala Arg Leu Ser Gly Ala
1               5                   10                  15
Leu Gly Thr Ser Asp His Ala Ser Val Val Ser Ile Thr Leu Phe Val
            20                  25                  30
Ala Leu Leu Cys Ala Cys Ile Val Leu Gly His Leu Glu Glu Asn
            35                  40                  45
Arg Trp Leu Asn Glu Ser Ile Thr Ala Leu Ile Ile Gly Leu Cys Thr
    50                  55                  60
Gly Val Val Ile Leu Met Thr Thr Lys Gly Lys Ser Ser His Val Leu
65                  70                  75                  80
Val Phe Ser Glu Asp Leu Phe Phe Ile Tyr Leu Leu Pro Pro Ile Ile
                85                  90                  95
Phe Asn Ala Gly Phe Gln Val Lys Lys Lys Gln Phe Phe Arg Asn Phe
```

```
                100                 105                 110
Met Ala Ile Thr Leu Phe Gly Ala Val Gly Thr Met Met Ser Phe Phe
            115                 120                 125

Thr Ile Ser Leu Ala Ala Ile Ala Ile Phe Ser Arg Met Asn Ile Gly
        130                 135                 140

Thr Leu Asp Val Ser Asp Phe Leu Ala Ile Gly Ala Ile Phe Ser Ala
145                 150                 155                 160

Thr Asp Ser Val Cys Thr Leu Gln Val Leu Asn Gln Asp Glu Thr Pro
                165                 170                 175

Phe Leu Tyr Ser Leu Val Phe Gly Glu Gly Val Val Asn Asp Ala Thr
            180                 185                 190

Ser Val Val Leu Phe Asn Ala Leu Gln Asn Phe Asp Pro Asn Gln Ile
        195                 200                 205

Asp Ala Ile Val Ile Leu Lys Phe Leu Gly Asn Phe Cys Tyr Leu Phe
210                 215                 220

Val Ser Ser Thr Phe Leu Gly Val Phe Thr Gly Leu Leu Ser Ala Tyr
225                 230                 235                 240

Val Ile Lys Lys Leu Tyr Ile Gly Arg His Ser Thr Asp Arg Glu Val
                245                 250                 255

Ala Leu Val Met Leu Met Ala Tyr Leu Ser Tyr Met Leu Ala Glu Leu
            260                 265                 270

Leu Asp Leu Ser Gly Ile Leu Thr Val Phe Phe Cys Gly Ile Val Met
        275                 280                 285

Ser His Tyr Thr Trp His Asn Val Thr Glu Ser Ser Arg Val Thr Thr
290                 295                 300

Lys His Ala Phe Ala Thr Leu Ser Phe Ile Ala Glu Thr Phe Leu Phe
305                 310                 315                 320

Leu Tyr Val Gly Met Asp Ala Leu Asp Ile Glu Lys Trp Lys Phe Ala
                325                 330                 335

Ser Asp Ser Pro Gly Lys Ser Ile Gly Ile Ser Ser Ile Leu Leu Gly
            340                 345                 350

Leu Val Leu Val Gly Arg Ala Ala Phe Val Phe Pro Leu Ser Phe Leu
        355                 360                 365

Ser Asn Leu Thr Lys Lys Thr Glu Leu Glu Lys Ile Ser Trp Arg Gln
370                 375                 380

Gln Ile Val Ile Trp Trp Ala Gly Leu Met Arg Gly Ala Val Ser Ile
385                 390                 395                 400

Ala Leu Ala Tyr Asn Lys Phe Thr Arg Ser Gly His Thr Gln Leu His
                405                 410                 415

Gly Asn Ala Ile Met Ile Thr Ser Thr Ile Thr Val Val Leu Phe Ser
            420                 425                 430

Thr Met Leu Phe Gly Ile Leu Thr Lys Pro Leu Ile Arg Phe Leu Leu
        435                 440                 445

Pro Ala Ser Ser Asn Gly Ala Ala Ser Asp Pro Ala Ser Pro Lys Ser
        450                 455                 460

Leu His Ser Pro Leu Leu Thr Ser Gln Leu Gly Ser Asp Leu Glu Ala
465                 470                 475                 480

Pro Leu Pro Ile Val Arg Pro Ser Ser Leu Arg Met Leu Ile Thr Lys
                485                 490                 495

Pro Thr His Thr Ile His Tyr Tyr Trp Arg Lys Phe Asp Asp Ala Leu
            500                 505                 510

Met Arg Pro Met Phe Gly Gly Arg Gly Phe Val Pro Tyr Ser Pro Gly
        515                 520                 525
```

```
Ser Pro Thr Asp Pro Asn Val Leu Val Glu
        530                 535

<210> SEQ ID NO 27
<211> LENGTH: 546
<212> TYPE: PRT
<213> ORGANISM: Triticum aestivum

<400> SEQUENCE: 27

Met Gly Leu Asp Leu Gly Ala Leu Ala Leu Lys Tyr Thr Gly Leu Ala
 1               5                  10                  15

Val Ser Asp His Asp Ser Ile Val Ala Ile Asn Ile Phe Ile Ala Leu
            20                  25                  30

Leu Cys Gly Cys Ile Val Phe Gly His Leu Leu Gly Gly Asn Arg Trp
        35                  40                  45

Val Asn Glu Ser Thr Ala Ala Leu Val Leu Gly Leu Ile Thr Gly Gly
    50                  55                  60

Val Ile Leu Ile Cys Thr Lys Val Asn Ser Arg Ile Leu Ile Phe
65                  70                  75                  80

Ser Glu Asp Ile Phe Phe Ile Tyr Leu Leu Pro Pro Ile Ile Phe Asn
                85                  90                  95

Ala Gly Phe Gln Val Lys Lys Gln Phe Phe Arg Asn Phe Ala Thr
            100                 105                 110

Ile Ile Leu Phe Gly Ala Ala Gly Thr Leu Ile Ser Phe Val Ile Ile
        115                 120                 125

Thr Phe Gly Ala Met Gly Leu Phe Ser Lys Leu Asp Val Gly Pro Leu
    130                 135                 140

Glu Leu Gly Asp Tyr Leu Ala Ile Gly Ala Ile Phe Ser Ala Thr Asp
145                 150                 155                 160

Ser Val Cys Thr Leu Gln Val Leu Asn Gln Asp Glu Ala Pro Leu Leu
                165                 170                 175

Tyr Ser Leu Val Phe Gly Glu Gly Val Val Asn Asp Ala Thr Ser Val
            180                 185                 190

Val Leu Phe Asn Ala Ile Gln Asn Ile Asp Ile Asn His Phe Asp Val
        195                 200                 205

Phe Gly Leu Leu Gln Phe Ile Gly Lys Phe Leu Tyr Leu Phe Phe Thr
    210                 215                 220

Ser Thr Val Leu Gly Val Ala Ala Gly Leu Leu Ser Ala Tyr Ile Ile
225                 230                 235                 240

Lys Lys Leu Cys Phe Ala Arg His Ser Thr Asp Arg Glu Val Ala Ile
                245                 250                 255

Met Ile Leu Met Ala Tyr Leu Ser Cys Met Leu Ser Met Leu Leu Asp
            260                 265                 270

Leu Ser Gly Ile Leu Thr Val Phe Phe Cys Gly Ile Val Met Ser His
        275                 280                 285

Tyr Thr Trp His Asn Val Thr Glu Ser Ser Arg Val Thr Thr Lys His
    290                 295                 300

Thr Phe Ala Thr Leu Ser Phe Ile Ala Glu Ile Phe Leu Phe Leu Tyr
305                 310                 315                 320

Val Gly Met Asp Ala Leu Asp Ile Asp Lys Trp Lys Leu Ala Ser Ser
                325                 330                 335

Ser Pro Lys Lys Pro Ile Ala Leu Ser Ala Val Ile Leu Gly Leu Val
            340                 345                 350

Met Val Gly Arg Ala Ala Phe Val Phe Pro Leu Ser Phe Leu Ser Asn
        355                 360                 365
```

```
Leu Ser Lys Lys Glu Ser His Pro Lys Ile Ser Phe Asn Gln Gln Val
    370                 375                 380

Ile Ile Trp Trp Ala Gly Leu Met Arg Gly Ala Val Ser Ile Ala Leu
385                 390                 395                 400

Ala Tyr Asn Lys Phe Thr Thr Ser Gly His Thr Ala Val Arg Val Asn
                405                 410                 415

Ala Val Met Ile Thr Ser Thr Ile Ile Val Val Leu Phe Ser Thr Met
            420                 425                 430

Val Phe Gly Leu Leu Thr Lys Pro Leu Ile Asn Leu Leu Ile Pro Pro
        435                 440                 445

Arg Pro Gly Thr Ala Ala Asp Ile Ser Ser Gln Ser Phe Leu Asp Pro
    450                 455                 460

Leu Thr Ala Ser Leu Leu Gly Ser Asp Phe Asp Val Gly Gln Leu Thr
465                 470                 475                 480

Pro Gln Thr Asn Leu Gln Tyr Leu Leu Thr Met Pro Thr Arg Ser Ala
                485                 490                 495

His Arg Val Trp Arg Lys Phe Asp Asp Lys Phe Met Arg Pro Met Phe
            500                 505                 510

Gly Gly Arg Gly Phe Val Pro Phe Val Pro Gly Ser Pro Ile Glu Arg
        515                 520                 525

Ser Val His Gly Pro Gly Leu Leu Gly Thr Val Thr Glu Ala Glu Asp
    530                 535                 540

Arg Ser
545

<210> SEQ ID NO 28
<211> LENGTH: 540
<212> TYPE: PRT
<213> ORGANISM: Zea mays

<400> SEQUENCE: 28

Met Gly Leu Gly Val Val Ala Glu Leu Val Arg Leu Gly Val Leu Ser
1               5                   10                  15

Ser Thr Ser Asp His Ala Ser Val Val Ser Ile Asn Leu Phe Val Ala
            20                  25                  30

Leu Leu Cys Ala Cys Ile Val Leu Gly His Leu Leu Glu Glu Asn Arg
        35                  40                  45

Trp Val Asn Glu Ser Thr Ala Leu Ile Val Gly Leu Gly Thr Gly Thr
    50                  55                  60

Val Ile Leu Met Ile Ser Arg Gly Val Val Ile His Val Leu Val Phe
65                  70                  75                  80

Ser Glu Asp Leu Phe Phe Phe Tyr Leu Leu Pro Pro Ile Ile Phe Asn
                85                  90                  95

Ala Gly Phe Gln Val Lys Lys Lys Gln Phe Phe Arg Asn Phe Ile Thr
            100                 105                 110

Ile Thr Leu Phe Gly Ala Val Gly Thr Leu Ile Ser Phe Thr Val Ile
        115                 120                 125

Ser Leu Gly Ala Leu Gly Leu Ile Ser Arg Leu Asn Ile Gly Ala Leu
    130                 135                 140

Glu Leu Gly Asp Tyr Leu Ala Leu Gly Ala Ile Phe Ser Ala Thr Asp
145                 150                 155                 160

Ser Val Cys Thr Leu Gln Val Leu Ser Gln Asp Glu Thr Pro Phe Leu
                165                 170                 175

Tyr Ser Leu Val Phe Gly Glu Gly Val Val Asn Asp Ala Thr Ser Val
            180                 185                 190
```

```
Val Val Phe Asn Ala Leu Gln Asn Phe Asp Ile Thr His Ile Asp Ala
        195                 200                 205

Glu Val Val Phe His Leu Leu Gly Asn Phe Phe Tyr Leu Phe Leu Leu
    210                 215                 220

Ser Thr Val Leu Gly Val Ala Thr Gly Leu Ile Ser Ala Leu Val Ile
225                 230                 235                 240

Lys Lys Leu Tyr Phe Gly Arg His Ser Thr Asp Arg Glu Val Ala Leu
                245                 250                 255

Met Met Leu Met Ala Tyr Leu Ser Tyr Met Leu Ala Glu Leu Phe Ala
                260                 265                 270

Leu Ser Gly Ile Leu Thr Val Phe Phe Gly Cys Ile Val Met Ser His
            275                 280                 285

Tyr Thr Trp His Asn Val Thr Glu Ser Ser Arg Ile Thr Thr Lys His
            290                 295                 300

Ala Phe Ala Thr Leu Ser Phe Leu Ala Glu Thr Phe Leu Phe Leu Tyr
305                 310                 315                 320

Val Gly Met Asp Ala Leu Asp Ile Asp Lys Trp Arg Ser Val Ser Asp
                325                 330                 335

Thr Pro Gly Lys Ser Leu Ala Ile Ser Ser Ile Leu Met Gly Leu Val
                340                 345                 350

Met Val Gly Arg Ala Ala Phe Val Phe Pro Leu Ser Phe Leu Ser Asn
            355                 360                 365

Leu Ala Lys Lys Thr Glu His Glu Lys Ile Ser Trp Lys Gln Gln Val
            370                 375                 380

Val Ile Trp Trp Ala Gly Leu Met Arg Gly Ala Val Ser Met Ala Leu
385                 390                 395                 400

Ala Tyr Lys Lys Phe Thr Arg Ala Gly His Thr Gln Val Arg Gly Asn
                405                 410                 415

Ala Ile Met Ile Thr Ser Thr Ile Ile Val Val Leu Phe Ser Thr Met
                420                 425                 430

Val Phe Gly Leu Leu Thr Lys Pro Leu Ile Asn Leu Leu Ile Pro His
            435                 440                 445

Arg Asn Ala Thr Ser Met Leu Ser Asp Asp Ser Pro Lys Ser Leu
    450                 455                 460

His Ser Pro Leu Leu Thr Ser Gln Leu Gly Ser Asp Leu Glu Glu Pro
465                 470                 475                 480

Thr Asn Ile Pro Arg Pro Ser Ser Ile Arg Gly Glu Phe Leu Thr Met
                485                 490                 495

Thr Arg Thr Val His Arg Tyr Trp Arg Lys Phe Asp Asp Ala Phe Met
                500                 505                 510

Arg Pro Met Phe Gly Gly Arg Gly Phe Val Pro Phe Val Pro Gly Ser
            515                 520                 525

Pro Thr Glu Arg Asn Pro Pro Asp Leu Ser Lys Ala
    530                 535                 540

<210> SEQ ID NO 29
<211> LENGTH: 540
<212> TYPE: PRT
<213> ORGANISM: Zea mays

<400> SEQUENCE: 29

Met Gly Leu Gly Val Asp Ala Glu Thr Val Arg Leu Gly Val Leu Ser
1               5                   10                  15

Ser Thr Ser Asp His Ala Ser Val Val Ser Asn Asn Phe Phe Val Ala
                20                  25                  30
```

```
Leu Leu Cys Ala Cys Ile Val Leu Gly His Leu Leu Glu Glu Asn Arg
        35                  40                  45

Met Val Asn Glu Ser Ile Thr Ala Leu Leu Val Gly Leu Gly Thr Gly
    50                  55                  60

Thr Val Ile Leu Met Ile Ser Arg Gly Val Ser Ile His Val Leu Val
65                  70                  75                  80

Phe Ser Glu Asp Leu Phe Phe Ile Tyr Leu Leu Pro Pro Ile Ile Phe
                85                  90                  95

Asn Ala Gly Phe Gln Val Lys Lys Gln Phe Arg Asn Phe Ile
            100                 105                 110

Thr Ile Ile Leu Phe Gly Ala Ile Gly Thr Leu Ile Ser Phe Val Ile
            115                 120                 125

Ile Ser Leu Gly Ala Met Gly Leu Phe Lys Lys Leu Asp Val Gly Pro
        130                 135                 140

Leu Glu Leu Gly Asp Tyr Leu Ala Ile Gly Ala Ile Phe Ser Ala Thr
145                 150                 155                 160

Asp Ser Val Cys Thr Leu Gln Val Leu Asn Gln Asp Glu Thr Pro Leu
                165                 170                 175

Leu Tyr Ser Leu Val Phe Gly Glu Gly Val Val Asn Asp Ala Thr Ser
            180                 185                 190

Ile Val Val Phe Asn Ala Leu Gln Asn Phe Asp Ile Thr His Ile Asn
            195                 200                 205

Ala Glu Val Val Phe His Leu Leu Gly Asn Phe Leu Tyr Leu Phe Leu
    210                 215                 220

Leu Ser Thr Val Leu Gly Val Ala Thr Gly Leu Ile Ser Ala Leu Val
225                 230                 235                 240

Ile Lys Lys Ile Tyr Phe Gly Arg His Ser Thr Asp Arg Glu Val Ala
            245                 250                 255

Leu Met Met Leu Met Ala Tyr Leu Ser Tyr Met Leu Ala Glu Leu Phe
            260                 265                 270

Ala Leu Ser Gly Ile Leu Thr Val Phe Phe Gly Cys Ile Val Met Ser
        275                 280                 285

His Tyr Thr Trp His Asn Val Thr Glu Ser Ser Arg Ile Thr Thr Lys
        290                 295                 300

His Ala Phe Ala Thr Leu Ser Phe Leu Ala Glu Thr Phe Ile Phe Leu
305                 310                 315                 320

Tyr Val Gly Met Asp Ala Leu Asp Ile Glu Lys Trp Arg Ser Val Ser
                325                 330                 335

Asp Thr Pro Gly Lys Ser Ile Ala Ile Ser Ser Ile Leu Met Gly Leu
            340                 345                 350

Val Met Leu Gly Arg Ala Ala Phe Val Phe Pro Leu Ser Phe Leu Ser
        355                 360                 365

Asn Leu Ala Lys Lys Asn Glu His Glu Lys Ile Ser Trp Lys Gln Gln
    370                 375                 380

Val Val Ile Trp Trp Ser Gly Leu Met Arg Gly Ala Val Ser Met Ala
385                 390                 395                 400

Leu Ala Tyr Asn Lys Phe Thr Arg Ala Gly His Thr Glu Val Arg Gly
                405                 410                 415

Asn Glu Ile Met Ile Thr Ser Thr Ile Thr Val Val Leu Phe Ser Thr
            420                 425                 430

Val Val Phe Gly Leu Leu Thr Lys Pro Leu Ile Arg Leu Leu Met Pro
        435                 440                 445

His Arg His Leu Thr Met Leu Ser Asp Asp Ser Thr Pro Lys Ser Leu
450                 455                 460
```

```
His Ser Pro Leu Leu Thr Ser Gln Leu Gly Ser Ser Ile Glu Glu Pro
465                 470                 475                 480

Thr Gln Ile Pro Arg Pro Thr Asn Ile Arg Gly Glu Phe Thr Thr Met
            485                 490                 495

Thr Arg Thr Val His Arg Tyr Trp Arg Lys Phe Asp Asp Lys Phe Met
                500                 505                 510

Arg Pro Met Phe Gly Gly Arg Gly Phe Val Pro Phe Val Pro Gly Ser
            515                 520                 525

Pro Thr Glu Arg Asn Pro His Asp Leu Ser Lys Pro
            530                 535                 540

<210> SEQ ID NO 30
<211> LENGTH: 539
<212> TYPE: PRT
<213> ORGANISM: Zea mays

<400> SEQUENCE: 30

Met Ser Ile Gly Leu Thr Ala Glu Thr Val Thr Asn Lys Leu Ala Ser
1               5                   10                  15

Ala Glu His Pro Gln Val Val Pro Asn Ser Val Phe Ile Ala Leu Leu
            20                  25                  30

Cys Leu Cys Leu Val Ile Gly His Leu Leu Glu Glu Asn Arg Trp Val
        35                  40                  45

Asn Glu Ser Ile Thr Ala Ile Leu Val Gly Ala Ala Thr Gly Thr Val
50                  55                  60

Ile Leu Leu Ile Ser Lys Gly Lys Ser Ser His Ile Leu Val Phe Asp
65                  70                  75                  80

Glu Glu Leu Phe Phe Ile Tyr Leu Leu Pro Pro Ile Ile Phe Asn Ala
                85                  90                  95

Gly Phe Gln Val Lys Lys Lys Gln Phe Phe Arg Asn Phe Ile Thr Ile
            100                 105                 110

Ile Leu Phe Gly Ala Ile Gly Thr Leu Ile Ser Phe Val Ile Ile Ser
        115                 120                 125

Leu Gly Ala Met Gly Leu Phe Lys Lys Leu Asp Val Gly Pro Leu Glu
130                 135                 140

Leu Gly Asp Tyr Leu Ala Ile Gly Ala Ile Phe Ser Ala Thr Asp Ser
145                 150                 155                 160

Val Cys Thr Leu Gln Val Leu Asn Gln Asp Glu Thr Pro Leu Leu Tyr
                165                 170                 175

Ser Leu Val Phe Gly Glu Gly Val Val Asn Asp Ala Thr Ser Val Val
            180                 185                 190

Leu Phe Asn Ala Val Gln Lys Ile Asp Phe Glu His Leu Thr Gly Glu
        195                 200                 205

Val Ala Leu Gln Val Phe Gly Asn Phe Leu Tyr Leu Phe Ser Thr Ser
210                 215                 220

Thr Val Leu Gly Ile Ala Thr Gly Leu Ile Thr Ala Phe Val Leu Lys
225                 230                 235                 240

Thr Leu Tyr Phe Gly Arg His Ser Thr Thr Arg Glu Leu Ala Ile Met
                245                 250                 255

Val Leu Met Ala Tyr Leu Ser Phe Met Leu Ala Glu Leu Phe Ser Leu
            260                 265                 270

Ser Gly Ile Ile Thr Val Phe Phe Cys Gly Val Leu Met Ser His Val
        275                 280                 285

Thr Trp His Asn Val Thr Glu Ser Ser Arg Ile Thr Ser Arg His Val
290                 295                 300
```

```
Phe Ala Met Leu Ser Phe Ile Ala Glu Thr Phe Leu Phe Leu Tyr Val
305                 310                 315                 320

Gly Thr Asp Ala Leu Asp Phe Thr Lys Trp Lys Thr Ser Ser Leu Ser
                325                 330                 335

Phe Gly Lys Ser Leu Gly Val Ser Ser Val Leu Leu Gly Leu Val Leu
            340                 345                 350

Val Gly Arg Ala Ala Phe Val Phe Pro Leu Ser Phe Leu Ser Asn Leu
        355                 360                 365

Ser Lys Lys His Pro Gly Glu Lys Ile Thr Ile Arg Gln Gln Val Val
    370                 375                 380

Ile Trp Trp Ala Gly Leu Met Arg Gly Ala Val Ser Ile Ala Leu Ala
385                 390                 395                 400

Phe Asn Lys Phe Thr Arg Ala Gly His Thr Gln Val Arg Gly Asn Ala
                405                 410                 415

Ile Met Ile Thr Ser Thr Ile Ile Val Val Leu Phe Ser Thr Val Val
            420                 425                 430

Phe Gly Leu Leu Thr Lys Pro Leu Ile Asn Leu Ile Pro His Arg
        435                 440                 445

Asn Ala Thr Ser Met Leu Ser Asp Asp Ser Ser Pro Lys Ser Leu His
    450                 455                 460

Ser Pro Leu Leu Thr Ser Gln Leu Ile Ser Ser Ile Glu Pro Thr
465                 470                 475                 480

Gln Ile Pro Arg Pro Thr Asn Ile Arg Gly Glu Phe Met Thr Met Thr
                485                 490                 495

Arg Thr Val His Arg Tyr Trp Arg Lys Phe Asp Asp Lys Phe Met Arg
            500                 505                 510

Pro Met Phe Gly Gly Arg Gly Phe Val Pro Phe Val Pro Gly Ser Pro
        515                 520                 525

Thr Glu Arg Ser Ser Pro Asp Leu Ser Lys Ala
    530                 535

<210> SEQ ID NO 31
<211> LENGTH: 538
<212> TYPE: PRT
<213> ORGANISM: Zea mays

<400> SEQUENCE: 31

Met Gly Tyr Gln Val Val Ala Ala Gln Leu Lys Leu Ala Ser Ser Ala
1               5                   10                  15

Asp His Ala Ser Val Val Ile Ile Thr Leu Phe Val Ala Leu Leu Cys
            20                  25                  30

Ala Cys Ile Val Leu Gly His Leu Leu Glu Glu Asn Arg Trp Leu Asn
        35                  40                  45

Glu Ser Ile Thr Ala Leu Ile Ile Gly Leu Gly Thr Gly Val Val Ile
    50                  55                  60

Leu Leu Ile Ser Arg Gly Lys Asn Ser Arg Leu Leu Val Phe Ser Glu
65                  70                  75                  80

Asp Leu Phe Phe Ile Tyr Leu Leu Pro Pro Ile Phe Asn Ala Gly
                85                  90                  95

Phe Gln Val Lys Lys Lys Gln Phe Phe Arg Asn Phe Met Thr Ile Thr
            100                 105                 110

Leu Phe Gly Ala Val Gly Thr Met Ile Ser Phe Phe Thr Ile Ser Leu
        115                 120                 125

Gly Ala Ile Ala Thr Phe Ser Arg Met Ser Ile Gly Thr Leu Asp Val
    130                 135                 140
```

```
Gly Asp Phe Leu Ala Ile Gly Ala Ile Phe Ser Ala Thr Asp Ser Val
145                 150                 155                 160

Cys Thr Leu Gln Val Leu His Gln Asp Glu Thr Pro Phe Leu Tyr Ser
            165                 170                 175

Leu Val Phe Gly Glu Gly Val Val Asn Asp Ala Thr Ser Val Val Leu
        180                 185                 190

Phe Asn Ala Val Gln Lys Ile Gln Phe Thr His Ile Asn Ala Trp Thr
    195                 200                 205

Ala Leu Gln Leu Ile Gly Asn Phe Leu Tyr Leu Phe Ser Thr Ser Thr
210                 215                 220

Leu Leu Gly Ile Gly Thr Gly Leu Ile Thr Ala Phe Val Leu Lys Lys
225                 230                 235                 240

Leu Tyr Phe Gly Arg His Ser Thr Thr Arg Glu Leu Ala Ile Met Ile
                245                 250                 255

Leu Met Ala Tyr Leu Ser Tyr Met Leu Ala Glu Leu Phe Ser Leu Ser
            260                 265                 270

Gly Leu Leu Thr Val Phe Phe Cys Gly Val Leu Met Ser His Val Thr
        275                 280                 285

Trp His Asn Val Thr Glu Ser Ser Arg Thr Thr Ser Arg His Val Phe
    290                 295                 300

Ala Thr Leu Ser Phe Ile Ser Glu Thr Phe Ile Phe Leu Tyr Val Gly
305                 310                 315                 320

Met Asp Ala Leu Asp Phe Glu Lys Trp Lys Thr Ser Ser Leu Ser Phe
                325                 330                 335

Gly Gly Thr Leu Gly Val Ser Gly Val Leu Met Gly Leu Val Met Leu
            340                 345                 350

Gly Arg Ala Ala Phe Val Phe Pro Leu Ser Phe Leu Ser Asn Leu Ala
        355                 360                 365

Lys Lys His Gln Ser Glu Lys Ile Ser Phe Arg Met Gln Val Val Ile
    370                 375                 380

Trp Trp Ala Gly Leu Met Arg Gly Ala Val Ser Met Ala Leu Ala Leu
385                 390                 395                 400

Asn Lys Phe Thr Arg Ser Gly His Thr Gln Leu His Gly Asn Ala Ile
                405                 410                 415

Met Ile Thr Ser Thr Ile Thr Val Val Leu Phe Ser Thr Met Val Phe
            420                 425                 430

Gly Met Ile Thr Lys Pro Leu Ile Arg Leu Leu Leu Pro Ala Ser Gly
        435                 440                 445

His Pro Arg Glu Leu Ser Glu Pro Ser Ser Pro Lys Ser Phe His Ser
    450                 455                 460

Pro Leu Leu Thr Ser Gln Gln Gly Ser Asp Leu Glu Ser Thr Thr Asn
465                 470                 475                 480

Ile Val Arg Pro Ser Ser Leu Arg Gly Leu Leu Thr Lys Pro Thr His
                485                 490                 495

Thr Val His Tyr Tyr Trp Arg Lys Phe Asp Asp Ala Leu Met Arg Pro
            500                 505                 510

Val Phe Gly Gly Arg Gly Phe Val Pro Phe Val Pro Gly Ser Pro Thr
        515                 520                 525

Glu Arg Asn Pro Pro Asp Leu Ser Lys Ala
    530                 535

<210> SEQ ID NO 32
<211> LENGTH: 545
<212> TYPE: PRT
```

<213> ORGANISM: Zea mays

<400> SEQUENCE: 32

```
Met Ser Met Gly Tyr Gln Val Ala Ala Gln Leu Lys Val Ala Ser
1               5                   10                  15

Ser Ala Asp His Ala Ser Val Val Ile Thr Leu Phe Val Ala Leu
            20                  25                  30

Leu Cys Ala Cys Ile Val Leu Gly His Leu Leu Glu Glu Asn Arg Trp
        35                  40                  45

Leu Asn Glu Ser Ile Thr Ala Leu Ile Ile Gly Leu Cys Thr Gly Gly
    50                  55                  60

Val Ile Leu Met Thr Thr Lys Gly Lys Ser Ser His Val Leu Val Phe
65                  70                  75                  80

Ser Glu Asp Leu Phe Phe Ile Tyr Leu Leu Pro Pro Ile Ile Phe Ile
                85                  90                  95

Ala Gly Phe Gln Val Lys Lys Lys Gln Phe Phe Arg Asn Phe Met Thr
            100                 105                 110

Ile Thr Leu Phe Gly Ala Val Gly Thr Met Ile Ser Phe Phe Thr Ile
        115                 120                 125

Ser Leu Gly Ala Ile Ala Ile Phe Ser Arg Met Asn Ile Gly Thr Leu
    130                 135                 140

Asp Val Gly Asp Phe Leu Ala Ile Gly Ala Ile Phe Ser Ala Thr Asp
145                 150                 155                 160

Ser Val Cys Thr Leu Gln Val Leu His Gln Asp Glu Thr Pro Phe Leu
                165                 170                 175

Tyr Ser Leu Val Phe Gly Glu Gly Val Val Asn Asp Ala Thr Ser Val
            180                 185                 190

Val Leu Phe Asn Ala Val Gln Lys Ile Gln Ile Thr His Ile Asn Ala
        195                 200                 205

Glu Val Ala Leu Gln Val Phe Gly Asn Phe Leu Tyr Leu Phe Ser Thr
    210                 215                 220

Ser Thr Leu Leu Gly Ile Ala Thr Gly Leu Ile Thr Ser Phe Val Leu
225                 230                 235                 240

Lys Lys Leu Tyr Phe Ala Arg His Ser Thr Thr Arg Glu Leu Ala Ile
                245                 250                 255

Met Met Leu Met Ala Tyr Leu Ser Tyr Met Leu Ala Glu Leu Phe Ser
            260                 265                 270

Leu Ser Gly Ile Leu Thr Val Phe Phe Cys Gly Val Leu Met Ser His
        275                 280                 285

Val Thr Trp His Asn Val Thr Glu Ser Ser Arg Ile Thr Ser Arg His
    290                 295                 300

Val Phe Ala Met Leu Ser Phe Ile Ala Glu Thr Phe Ile Phe Leu Tyr
305                 310                 315                 320

Val Gly Thr Asp Ala Leu Asp Phe Asp Lys Trp Lys Thr Ser Ser Leu
                325                 330                 335

Ser Phe Gly Gly Thr Leu Gly Val Ser Ala Leu Ile Met Ala Leu Val
            340                 345                 350

Leu Leu Gly Arg Ala Ala Phe Val Phe Pro Leu Ser Val Leu Thr Asn
        355                 360                 365

Phe Ser Asn Lys His Glu Asn Glu Ser Ile Thr Phe Lys His Gln Val
    370                 375                 380

Ile Ile Trp Trp Ala Gly Leu Met Arg Gly Ala Val Ser Ile Ala Leu
385                 390                 395                 400

Ala Phe Lys Gln Phe Thr Tyr Ser Gly Val Thr Leu Asp Pro Val Asn
```

```
                        405                 410                 415
Ala Ala Met Val Thr Asn Thr Thr Ile Val Val Leu Phe Thr Thr Leu
            420                 425                 430

Val Phe Gly Leu Leu Thr Lys Pro Leu Ile Arg Leu Leu Met Pro His
            435                 440                 445

Arg His Leu Thr Met Leu Ser Asp Asp Ser Thr Pro Lys Ser Leu His
            450                 455                 460

Ser Pro Leu Leu Thr Ser Gln Leu Gly Ser Asp Leu Glu Glu Pro Thr
465                 470                 475                 480

Asn Ile Pro Arg Pro Ser Ser Ile Arg Gly Glu Phe Leu Thr Met Thr
                485                 490                 495

Arg Thr Val His Arg Tyr Trp Arg Lys Phe Asp Asp Ala Phe Met Arg
            500                 505                 510

Pro Met Phe Gly Gly Arg Gly Phe Val Pro Val Pro Gly Ser Pro
            515                 520                 525

Ile Glu Arg Ser Val Pro Gln Trp Ser Glu Ala His Asn Lys Glu
            530                 535                 540

Pro
545

<210> SEQ ID NO 33
<211> LENGTH: 541
<212> TYPE: PRT
<213> ORGANISM: Zea mays

<400> SEQUENCE: 33

Met Gly Leu Gly Val Val Ala Glu Leu Val Arg Leu Gly Val Leu Ser
1               5                   10                  15

Ser Thr Ser Asp His Ala Ser Val Val Ser Ile Asn Leu Phe Val Ala
            20                  25                  30

Leu Leu Cys Ala Cys Ile Val Leu Gly His Leu Leu Glu Glu Asn Arg
        35                  40                  45

Trp Val Asn Glu Ser Ile Thr Ala Leu Ile Ile Gly Leu Cys Thr Gly
    50                  55                  60

Val Val Ile Leu Leu Thr Thr Lys Gly Lys Ser Ser His Ile Leu Val
65                  70                  75                  80

Phe Ser Glu Asp Leu Phe Phe Ile Tyr Leu Leu Pro Pro Ile Ile Phe
                85                  90                  95

Asn Ala Gly Phe Gln Val Lys Lys Lys Gln Phe Phe Arg Asn Phe Met
            100                 105                 110

Thr Ile Thr Leu Phe Gly Ala Val Gly Thr Met Ile Ser Phe Phe Thr
        115                 120                 125

Ile Ser Leu Gly Ala Leu Gly Leu Ile Ser Arg Leu Asn Ile Gly Ala
    130                 135                 140

Leu Glu Leu Gly Asp Tyr Leu Ala Leu Gly Ala Ile Phe Ser Ala Thr
145                 150                 155                 160

Asp Ser Val Cys Thr Leu Gln Val Leu Ser Gln Asp Glu Thr Pro Phe
                165                 170                 175

Leu Tyr Ser Leu Val Phe Gly Glu Gly Val Val Asn Asp Ala Thr Ser
            180                 185                 190

Val Val Val Phe Asn Ala Leu Gln Asn Phe Asp Ile Thr His Ile Asp
        195                 200                 205

Ala Glu Val Val Phe His Leu Leu Gly Asn Phe Phe Tyr Leu Phe Leu
    210                 215                 220

Leu Ser Thr Val Leu Gly Val Ala Thr Gly Leu Ile Ser Ala Leu Val
```

```
            225                 230                 235                 240
Ile Lys Lys Leu Tyr Phe Gly Arg His Ser Thr Asp Arg Glu Val Ala
                245                 250                 255

Leu Met Met Leu Met Ala Tyr Leu Ser Tyr Met Leu Ala Glu Leu Phe
                260                 265                 270

Ala Leu Ser Gly Ile Leu Thr Val Phe Phe Gly Cys Ile Val Met Ser
                275                 280                 285

His Tyr Thr Trp His Asn Val Thr Glu Ser Ser Arg Ile Thr Thr Lys
                290                 295                 300

His Ala Phe Ala Thr Leu Ser Phe Leu Ala Glu Thr Phe Leu Phe Leu
305                 310                 315                 320

Tyr Val Gly Met Asp Ala Leu Asp Ile Asp Lys Trp Arg Ser Val Ser
                325                 330                 335

Asp Thr Pro Gly Lys Ser Leu Ala Ile Ser Ser Ile Leu Met Gly Leu
                340                 345                 350

Val Met Val Gly Arg Ala Ala Phe Val Phe Pro Leu Ser Phe Leu Ser
                355                 360                 365

Asn Leu Ala Lys Lys Thr Glu His Glu Lys Ile Ser Trp Lys Gln Gln
                370                 375                 380

Val Val Ile Trp Trp Ala Gly Leu Met Arg Gly Ala Val Ser Met Ala
385                 390                 395                 400

Leu Ala Tyr Lys Lys Phe Thr Arg Ala Gly His Thr Gln Val Arg Gly
                405                 410                 415

Asn Ala Ile Met Ile Thr Ser Thr Ile Val Val Leu Phe Ser Thr
                420                 425                 430

Met Val Phe Gly Leu Leu Thr Lys Pro Leu Ile Asn Leu Leu Ile Pro
                435                 440                 445

His Arg Asn Ala Thr Ser Met Leu Ser Asp Asp Ser Ser Pro Lys Ser
450                 455                 460

Leu His Ser Pro Leu Leu Thr Ser Gln Leu Gly Ser Asp Leu Glu Glu
465                 470                 475                 480

Pro Thr Asn Ile Pro Arg Pro Ser Ser Ile Arg Gly Glu Phe Leu Thr
                485                 490                 495

Met Thr Arg Thr Val His Arg Tyr Trp Arg Lys Phe Asp Asp Ala Phe
                500                 505                 510

Met Arg Pro Met Phe Gly Gly Arg Gly Phe Val Pro Phe Val Pro Gly
                515                 520                 525

Ser Pro Thr Glu Arg Asn Pro Pro Asp Leu Ser Lys Ala
                530                 535                 540

<210> SEQ ID NO 34
<211> LENGTH: 543
<212> TYPE: PRT
<213> ORGANISM: Gossypium hirsutum

<400> SEQUENCE: 34

Met Val Ala Pro Gln Leu Ala Ala Val Phe Thr Lys Leu Gln Thr Leu
  1               5                  10                  15

Ser Thr Ser Asp His Ala Ser Val Val Ser Met Asn Ile Phe Val Ala
                 20                  25                  30

Leu Leu Cys Ala Cys Ile Val Ile Gly His Leu Leu Glu Glu Asn Arg
             35                  40                  45

Trp Met Asn Glu Ser Ile Thr Ala Leu Ile Ile Gly Val Phe Thr Gly
         50                  55                  60

Val Ile Ile Leu Leu Thr Ser Gly Gly Lys Ser Ser His Leu Leu Val
```

```
            65                  70                  75                  80
Phe Ser Glu Asp Leu Phe Phe Ile Tyr Leu Leu Pro Pro Ile Ile Phe
                85                  90                  95

Asn Ala Gly Phe Gln Val Lys Lys Gln Phe Phe Arg Asn Phe Ile
            100                 105                 110

Thr Ile Met Leu Phe Gly Ala Val Gly Thr Leu Ile Ser Cys Thr Ile
            115                 120                 125

Ile Ser Leu Gly Val Ile Asn Phe Phe Lys Glu Met Asp Ile Gly Ser
        130                 135                 140

Leu Asp Ile Gly Asp Phe Leu Ala Ile Gly Ala Ile Phe Ala Ala Thr
145                 150                 155                 160

Asp Ser Val Cys Thr Leu Gln Val Leu Asn Gln Asp Glu Thr Pro Leu
                165                 170                 175

Leu Tyr Ser Leu Val Phe Gly Glu Gly Val Val Asn Asp Ala Thr Ser
            180                 185                 190

Val Val Leu Phe Asn Ala Ile Gln Ser Phe Asp Leu Val Asn Thr Ser
        195                 200                 205

Pro Arg Ile Leu Leu Glu Phe Ile Gly Ser Phe Leu Tyr Leu Phe Leu
    210                 215                 220

Ala Ser Thr Met Leu Gly Val Ile Val Gly Leu Val Ser Ala Tyr Ile
225                 230                 235                 240

Ile Lys Lys Leu Tyr Phe Gly Arg His Ser Thr Asp Arg Glu Phe Ala
                245                 250                 255

Leu Met Met Leu Met Ala Tyr Leu Ser Tyr Ile Met Ala Glu Leu Phe
            260                 265                 270

Tyr Leu Ser Gly Ile Leu Thr Val Phe Phe Cys Gly Ile Val Met Ser
        275                 280                 285

His Tyr Thr Trp His Asn Val Thr Glu Ser Ser Arg Val Thr Thr Lys
    290                 295                 300

His Ala Phe Ala Thr Leu Ser Phe Val Ala Glu Thr Phe Leu Phe Leu
305                 310                 315                 320

Tyr Val Gly Met Asp Ala Leu Asp Met Glu Lys Trp Arg Phe Val Ser
                325                 330                 335

Asp Ser Pro Gly Thr Ser Val Ala Val Ser Ala Val Leu Met Gly Leu
            340                 345                 350

Val Met Val Gly Arg Ala Ala Phe Val Phe Pro Leu Ser Phe Leu Ser
        355                 360                 365

Asn Leu Ala Lys Lys Ser Thr Ser Glu Lys Ile Ser Phe Arg Glu Gln
    370                 375                 380

Ile Ile Ile Trp Trp Ala Gly Leu Met Arg Gly Ala Val Ser Met Ala
385                 390                 395                 400

Leu Ala Tyr Asn Gln Phe Thr Arg Gly Gly His Thr Gln Leu Arg Gly
                405                 410                 415

Asn Ala Ile Met Ile Thr Ser Thr Ile Thr Ile Val Leu Phe Ser Thr
            420                 425                 430

Val Val Phe Gly Leu Met Thr Lys Pro Leu Ile Arg Phe Leu Leu Pro
        435                 440                 445

His Pro Lys Pro Thr Ala Ser Met Leu Ser Asp Gln Ser Thr Pro Lys
    450                 455                 460

Ser Met Glu Ala Pro Phe Leu Gly Ser Gly Gln Asp Ser Phe Asp Asp
465                 470                 475                 480

Ser Leu Ile Gly Val His Arg Pro Asn Ser Ile Arg Ala Leu Leu Thr
                485                 490                 495
```

-continued

Thr Pro Ala His Thr Val His Tyr Tyr Trp Arg Lys Phe Asp Asn Ala
            500                 505                 510

Phe Met Arg Pro Met Phe Gly Arg Gly Phe Val Pro Phe Val Pro
        515                 520                 525

Gly Ser Pro Thr Glu Arg Ser Glu Pro Asn Leu Pro Gln Trp Gln
        530                 535                 540

<210> SEQ ID NO 35
<211> LENGTH: 557
<212> TYPE: PRT
<213> ORGANISM: Suaeda maritima

<400> SEQUENCE: 35

Met Trp Ser Gln Leu Ser Ser Phe Phe Ala Ser Lys Met Asp Met Val
 1               5                  10                  15

Ser Thr Ser Asp His Ala Ser Val Val Ser Met Asn Leu Phe Val Ala
            20                  25                  30

Leu Leu Cys Gly Cys Ile Val Ile Gly His Leu Glu Glu Asn Arg
        35                  40                  45

Trp Met Asn Glu Ser Ile Thr Ala Leu Leu Ile Gly Leu Ser Thr Gly
 50                  55                  60

Ile Ile Ile Leu Leu Ile Ser Gly Gly Lys Ser Ser His Leu Leu Val
65                  70                  75                  80

Phe Ser Glu Asp Leu Phe Phe Ile Tyr Leu Leu Pro Pro Ile Ile Phe
                85                  90                  95

Asn Ala Gly Phe Gln Val Lys Lys Lys Gln Phe Phe Arg Asn Phe Ile
            100                 105                 110

Thr Ile Ile Leu Phe Gly Ala Val Gly Thr Leu Val Ser Phe Ile Ile
        115                 120                 125

Ile Ser Leu Gly Ser Ile Ala Ile Phe Gln Lys Met Asp Ile Gly Ser
        130                 135                 140

Leu Glu Leu Gly Asp Leu Leu Ala Ile Gly Ala Ile Phe Ala Ala Thr
145                 150                 155                 160

Asp Ser Val Cys Thr Leu Gln Val Leu Asn Gln Asp Glu Thr Pro Leu
                165                 170                 175

Leu Tyr Ser Leu Val Phe Gly Glu Gly Val Val Asn Asp Ala Thr Ser
            180                 185                 190

Val Val Leu Phe Asn Ala Ile Gln Asn Phe Asp Leu Thr His Ile Asp
        195                 200                 205

His Arg Ile Ala Tyr Arg Ile Ala Phe Gln Phe Gly Gly Asn Phe Leu
    210                 215                 220

Tyr Leu Phe Phe Ala Ser Thr Leu Leu Gly Ala Val Thr Gly Leu Leu
225                 230                 235                 240

Ser Ala Tyr Val Ile Lys Lys Leu Tyr Phe Gly Arg His Ser Thr Asp
                245                 250                 255

Arg Glu Val Ala Leu Met Met Leu Met Ala Tyr Leu Ser Tyr Met Leu
            260                 265                 270

Ala Glu Leu Phe Tyr Leu Ser Gly Ile Leu Thr Val Phe Phe Cys Gly
        275                 280                 285

Ile Val Met Ser His Tyr Thr Trp His Asn Val Thr Glu Ser Ser Arg
    290                 295                 300

Val Thr Thr Lys His Ala Phe Ala Thr Leu Ser Phe Val Ala Glu Ile
305                 310                 315                 320

Phe Ile Phe Leu Tyr Val Gly Met Asp Ala Leu Asp Ile Glu Lys Trp
                325                 330                 335

```
Arg Phe Val Ser Asp Ser Pro Gly Thr Ser Val Ala Val Ser Ser Ile
            340                 345                 350

Leu Leu Gly Leu Leu Met Val Gly Arg Ala Leu Leu Phe Ser Leu Val
            355                 360                 365

Phe Leu Met Asn Leu Ser Lys Lys Ser Asn Ser Glu Lys Val Thr Phe
370                 375                 380

Asn Gln Gln Ile Val Ile Trp Trp Ala Gly Leu Met Arg Gly Ala Val
385                 390                 395                 400

Ser Val Ala Leu Ala Tyr Asn Gln Phe Ser Arg Ser Gly His Thr Gln
            405                 410                 415

Leu Arg Gly Asn Ala Ile Met Ile Thr Ser Thr Ile Thr Val Val Leu
            420                 425                 430

Phe Ser Thr Met Val Phe Gly Leu Leu Thr Lys Pro Leu Ile Leu Phe
            435                 440                 445

Met Leu Pro Gln Pro Lys His Phe Thr Ser Ala Ser Thr Val Ser Asp
            450                 455                 460

Leu Gly Ser Pro Lys Ser Phe Ser Leu Pro Leu Leu Glu Asp Arg Gln
465                 470                 475                 480

Asp Ser Glu Ala Asp Leu Gly Asn Asp Asp Glu Glu Ala Tyr Pro Arg
            485                 490                 495

Gly Thr Ile Ala Arg Pro Thr Ser Leu Arg Met Leu Leu Asn Ala Pro
            500                 505                 510

Thr His Thr Val His His Tyr Trp Arg Arg Phe Asp Asp Tyr Phe Met
            515                 520                 525

Arg Pro Val Phe Gly Gly Arg Gly Phe Val Pro Phe Val Pro Gly Ser
            530                 535                 540

Pro Thr Glu Gln Ser Thr Thr Asn Leu Ser Gln Arg Thr
545                 550                 555

<210> SEQ ID NO 36
<211> LENGTH: 538
<212> TYPE: PRT
<213> ORGANISM: Hordeum vulgare

<400> SEQUENCE: 36

Met Ala Phe Glu Val Val Ala Ala Gln Leu Ala Arg Leu Ser Asp Ala
1               5                   10                  15

Leu Ala Thr Ser Asp His Ala Ser Val Val Ser Ile Asn Leu Phe Val
            20                  25                  30

Ala Leu Leu Cys Ala Cys Ile Val Leu Gly His Leu Leu Glu Glu Asn
            35                  40                  45

Arg Trp Leu Asn Glu Ser Ile Thr Ala Leu Ile Ile Gly Leu Cys Thr
50                  55                  60

Gly Val Val Ile Leu Met Thr Thr Lys Gly Lys Ser Ser His Val Leu
65                  70                  75                  80

Val Phe Ser Glu Asp Leu Phe Phe Ile Tyr Leu Leu Pro Pro Ile Ile
            85                  90                  95

Phe Asn Ala Gly Phe Gln Val Lys Lys Lys Gln Phe Phe Arg Asn Phe
            100                 105                 110

Met Thr Ile Thr Leu Phe Gly Ala Val Gly Thr Met Ile Ser Phe Phe
            115                 120                 125

Thr Ile Ser Leu Ala Ala Ile Ala Phe Ser Lys Met Asn Ile Gly
            130                 135                 140

Thr Leu Asp Val Ser Asp Phe Leu Ala Ile Gly Ala Ile Phe Ser Ala
145                 150                 155                 160
```

```
Thr Asp Ser Val Cys Thr Leu Gln Val Leu Asn Gln Asp Glu Thr Pro
            165                 170                 175

Phe Leu Tyr Ser Leu Val Phe Gly Glu Gly Val Val Asn Asp Ala Thr
        180                 185                 190

Ser Val Val Leu Phe Asn Ala Leu Gln Asn Phe Asp Pro Asn Gln Ile
    195                 200                 205

Asp Ala Ile Val Ile Leu Lys Phe Leu Gly Asn Phe Cys Tyr Leu Phe
210                 215                 220

Val Ser Ser Thr Phe Leu Gly Val Phe Ser Gly Leu Leu Ser Ala Tyr
225                 230                 235                 240

Ile Ile Lys Lys Leu Tyr Ile Gly Arg His Ser Thr Arg Glu Val
            245                 250                 255

Ala Leu Met Met Leu Met Ala Tyr Leu Ser Tyr Met Leu Ala Glu Leu
            260                 265                 270

Leu Asp Leu Ser Gly Ile Leu Thr Val Phe Phe Cys Gly Ile Val Met
        275                 280                 285

Ser His Tyr Thr Trp His Asn Val Thr Glu Ser Ser Arg Val Thr Thr
        290                 295                 300

Lys His Ala Phe Ala Thr Leu Ser Phe Ile Ala Glu Thr Phe Leu Phe
305                 310                 315                 320

Leu Tyr Val Gly Met Asp Ala Leu Asp Ile Glu Lys Trp Lys Phe Ala
                325                 330                 335

Ser Asp Ser Pro Gly Lys Ser Ile Gly Ile Ser Ser Ile Leu Leu Gly
            340                 345                 350

Leu Val Leu Val Gly Arg Ala Ala Phe Val Phe Pro Leu Ser Phe Leu
        355                 360                 365

Ser Asn Leu Thr Lys Lys Thr Glu Leu Glu Lys Ile Ser Trp Arg Gln
370                 375                 380

Gln Ile Val Ile Trp Trp Ala Gly Leu Met Arg Gly Ala Val Ser Ile
385                 390                 395                 400

Ala Leu Ala Tyr Asn Lys Phe Thr Arg Ser Gly His Thr Gln Leu His
                405                 410                 415

Gly Asn Ala Ile Met Ile Thr Ser Thr Ile Thr Val Val Leu Phe Ser
            420                 425                 430

Thr Met Leu Phe Gly Ile Leu Thr Lys Pro Leu Ile Arg Phe Leu Leu
        435                 440                 445

Pro Ala Ser Ser Asn Gly Asp Pro Ser Glu Pro Ser Ser Pro Lys Ser
    450                 455                 460

Leu His Ser Pro Leu Leu Thr Ser Met Leu Gly Ser Asp Met Glu Ala
465                 470                 475                 480

Pro Leu Pro Ile Val Arg Pro Ser Ser Leu Arg Met Leu Ile Thr Lys
                485                 490                 495

Pro Thr His Thr Ile His Tyr Tyr Trp Arg Lys Phe Asp Asp Ala Leu
            500                 505                 510

Met Arg Pro Met Phe Gly Gly Arg Gly Phe Val Pro Tyr Ser Pro Gly
        515                 520                 525

Ser Pro Thr Asp Pro Asn Val Ile Val Ala
    530                 535
```

<210> SEQ ID NO 37
<211> LENGTH: 540
<212> TYPE: PRT
<213> ORGANISM: Hordeum brevisubulatum

<400> SEQUENCE: 37

-continued

```
Met Gly Trp Gly Leu Gly Asp Pro Pro Ala Asp Tyr Gly Ser Ile Met
 1               5                  10                  15

Ala Val Gly Leu Phe Val Ala Leu Met Cys Ile Cys Ile Ile Val Gly
                20                  25                  30

His Leu Leu Glu Glu Asn Arg Trp Met Asn Glu Ser Thr Thr Ala Leu
            35                  40                  45

Leu Leu Gly Leu Gly Ala Gly Thr Val Ile Leu Phe Ala Ser Ser Gly
        50                  55                  60

Lys Asn Ser Arg Leu Met Val Phe Ser Glu Asp Leu Phe Phe Ile Tyr
 65                  70                  75                  80

Leu Leu Pro Pro Ile Ile Phe Asn Ala Gly Phe Gln Val Lys Lys Lys
                85                  90                  95

Gln Phe Phe Arg Asn Phe Met Thr Ile Thr Leu Phe Ala Val Val Gly
                100                 105                 110

Thr Leu Ile Ser Phe Ser Ile Ile Ser Leu Gly Ala Met Gly Leu Ile
            115                 120                 125

Ser Arg Leu Asn Ile Gly Ala Leu Glu Leu Gly Asp Tyr Leu Ala Leu
    130                 135                 140

Gly Ala Ile Phe Ser Ala Thr Asp Ser Val Cys Thr Leu Gln Val Leu
145                 150                 155                 160

Ser Gln Asp Glu Thr Pro Phe Leu Tyr Ser Leu Val Phe Gly Glu Gly
                165                 170                 175

Val Val Asn Asp Ala Thr Ser Val Val Leu Phe Asn Ala Ile Gln Asn
                180                 185                 190

Phe Asp Leu Gly Asn Phe Ser Ser Leu Lys Phe Leu Gln Phe Ile Gly
        195                 200                 205

Asn Phe Leu Tyr Leu Phe Gly Ala Ser Thr Phe Leu Gly Val Ala Ser
    210                 215                 220

Gly Leu Leu Ser Ala Tyr Val Ile Lys Lys Leu Tyr Phe Gly Arg His
225                 230                 235                 240

Ser Thr Asp Arg Glu Val Ala Ile Met Met Leu Met Ala Tyr Leu Ser
                245                 250                 255

Tyr Met Leu Ala Glu Leu Leu Asp Leu Ser Gly Ile Leu Thr Val Phe
                260                 265                 270

Phe Cys Gly Ile Val Met Ser His Tyr Thr Trp His Asn Val Thr Glu
            275                 280                 285

Ser Ser Arg Val Thr Thr Lys His Ala Phe Ala Thr Leu Ser Phe Ile
    290                 295                 300

Ser Glu Thr Phe Leu Phe Leu Tyr Val Gly Met Asp Ala Leu Asp Ile
305                 310                 315                 320

Glu Lys Trp Lys Ile Val Ser Glu Thr Tyr Ser Pro Met Lys Ser Ile
                325                 330                 335

Thr Leu Ser Ser Ile Ile Leu Ala Leu Val Leu Val Ala Arg Ala Ala
            340                 345                 350

Phe Val Phe Pro Leu Ser Tyr Leu Ser Asn Leu Thr Lys Lys Thr Ala
        355                 360                 365

Gly Glu Lys Ile Ser Ile Arg Gln Gln Val Ile Trp Trp Ala Gly
    370                 375                 380

Leu Met Arg Gly Ala Val Ser Ile Ala Leu Ala Tyr Asn Lys Phe Ala
385                 390                 395                 400

Lys Ser Gly His Thr Gln Leu Pro Ser Asn Ala Ile Met Ile Thr Ser
                405                 410                 415

Thr Ile Ile Ile Val Leu Phe Ser Thr Ile Val Phe Gly Leu Leu Thr
            420                 425                 430
```

```
Lys Pro Leu Ile Arg Leu Leu Ile Pro Ala Arg His Leu Thr Arg Glu
            435                 440                 445

Val Ser Ala Leu Ser Glu Pro Ser Pro Lys Ser Phe Leu Glu Gln
450                 455                 460

Leu Thr Val Asn Gly Pro Glu Thr Asp Val Glu Asn Gly Val Ser Ile
465                 470                 475                 480

Arg Arg Pro Thr Ser Leu Arg Met Leu Ala Ser Pro Thr Arg Ser
                485                 490                 495

Val His His Tyr Trp Arg Lys Phe Asp Asn Ala Phe Met Arg Pro Val
                500                 505                 510

Phe Gly Gly Arg Gly Phe Val Pro Phe Val Pro Gly Ser Pro Thr Glu
                515                 520                 525

Ser Ser Val Pro Leu Leu Ala His Gly Ser Glu Asn
                530                 535                 540

<210> SEQ ID NO 38
<211> LENGTH: 546
<212> TYPE: PRT
<213> ORGANISM: Hordeum vulgare

<400> SEQUENCE: 38

Met Gly Pro Asp Leu Gly Ala Leu Ala Leu Arg Tyr Thr Gly Leu Ala
  1               5                  10                  15

Val Ser Asp His Asp Ser Ile Val Ala Ile Asn Ile Phe Ile Ala Leu
             20                  25                  30

Leu Cys Gly Cys Ile Val Phe Gly His Leu Leu Glu Gly Asn Arg Trp
         35                  40                  45

Val Asn Glu Ser Thr Thr Ala Ile Val Leu Gly Leu Ile Thr Gly Gly
 50                  55                  60

Val Ile Leu Leu Cys Thr Lys Gly Val Asn Ser Arg Ile Leu Ile Phe
 65                  70                  75                  80

Ser Glu Asp Ile Phe Phe Ile Tyr Leu Leu Pro Pro Ile Ile Phe Asn
                 85                  90                  95

Ala Gly Phe Gln Val Lys Lys Lys Gln Phe Phe Arg Asn Phe Ala Thr
            100                 105                 110

Ile Ile Leu Phe Gly Ala Val Gly Thr Leu Ile Ser Phe Val Ile Ile
        115                 120                 125

Thr Leu Gly Ala Met Gly Leu Phe Arg Lys Leu Asp Val Gly Pro Leu
130                 135                 140

Glu Leu Gly Asp Tyr Leu Ala Ile Gly Ala Ile Phe Ser Ala Thr Asp
145                 150                 155                 160

Ser Val Cys Thr Leu Gln Val Leu Asn Gln Asp Gln Ala Pro Leu Leu
                165                 170                 175

Tyr Ser Leu Val Phe Gly Glu Gly Val Val Asn Asp Ala Thr Ser Val
            180                 185                 190

Val Leu Phe Asn Ala Ile Gln Asn Ile Asp Leu Asn His Phe Asp Val
        195                 200                 205

Leu Val Leu Leu Gln Leu Ile Gly Lys Phe Leu Tyr Leu Phe Leu Thr
    210                 215                 220

Ser Thr Val Leu Gly Val Ala Ala Gly Leu Leu Ser Ala Tyr Ile Ile
225                 230                 235                 240

Lys Lys Leu Cys Phe Ala Arg His Ser Thr Asp Arg Glu Val Ala Ile
                245                 250                 255

Met Ile Leu Met Ala Tyr Leu Ser Tyr Met Leu Ser Met Leu Leu Asp
            260                 265                 270
```

```
Leu Ser Gly Ile Leu Thr Val Phe Phe Cys Gly Ile Val Met Ser His
            275                 280                 285
Tyr Thr Arg His Asn Val Thr Glu Ser Ser Arg Val Thr Thr Lys His
        290                 295                 300
Thr Phe Ala Thr Leu Ser Phe Ile Ala Glu Ile Phe Leu Phe Leu Tyr
305                 310                 315                 320
Val Gly Met Asp Ala Leu Asp Ile Asp Lys Trp Lys Leu Ala Ser Ser
                325                 330                 335
Ser Pro Lys Lys Pro Ile Ala Leu Ser Ala Val Ile Leu Gly Leu Val
            340                 345                 350
Met Val Gly Arg Ala Ala Phe Val Phe Pro Leu Ser Tyr Leu Ser Asn
            355                 360                 365
Leu Ser Lys Lys Glu Ser His Pro Lys Ile Ser Phe Asn Gln Gln Val
            370                 375                 380
Ile Ile Trp Trp Ala Gly Leu Met Arg Gly Ala Val Ser Ile Ala Leu
385                 390                 395                 400
Ala Tyr Asn Lys Tyr Thr Thr Ser Gly His Thr Ala Val Arg Val Asn
                405                 410                 415
Ala Val Met Ile Thr Ser Thr Ile Ile Val Val Leu Phe Ser Thr Met
            420                 425                 430
Val Phe Gly Leu Leu Thr Lys Pro Leu Ile Asn Leu Leu Val Pro Pro
            435                 440                 445
Arg Pro Gly Thr Ala Ala Asp Ile Ser Ser Gln Ser Phe Leu Asp Pro
    450                 455                 460
Leu Thr Ala Ser Leu Leu Gly Ser Asp Phe Asp Val Gly Gln Leu Thr
465                 470                 475                 480
Pro Gln Thr Asn Leu Gln Tyr Leu Leu Thr Met Pro Ser Arg Ser Val
                485                 490                 495
His Arg Val Trp Arg Lys Phe Asp Asp Lys Phe Met Arg Pro Met Phe
            500                 505                 510
Gly Gly Arg Gly Phe Val Pro Phe Val Pro Gly Ser Pro Ile Glu Arg
            515                 520                 525
Ser Val His Gly Pro Gly Leu Leu Gly Thr Val Thr Glu Ala Glu Asn
            530                 535                 540
Arg Ser
545
```